(12) United States Patent
DeFonzo et al.

(10) Patent No.: US 8,500,674 B2
(45) Date of Patent: Aug. 6, 2013

(54) DIALYSIS CATHETER

(75) Inventors: Stephan A. DeFonzo, Wayne, PA (US); John D. Leedle, Philadelphia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 412 days.

(21) Appl. No.: 12/497,574

(22) Filed: Jul. 3, 2009

(65) Prior Publication Data

US 2009/0312687 A1     Dec. 17, 2009

Related U.S. Application Data

(63) Continuation of application No. 12/079,716, filed on Mar. 28, 2008, now Pat. No. 8,323,228, and a continuation-in-part of application No. 11/487,750, filed on Jul. 17, 2006, now Pat. No. 7,566,316, which is a continuation of application No. 10/279,468, filed on Oct. 24, 2002, now Pat. No. 7,077,829, which is a continuation-in-part of application No. 10/025,506, filed on Dec. 19, 2001, now Pat. No. 6,814,718.

(60) Provisional application No. 60/923,101, filed on Apr. 12, 2007, provisional application No. 60/260,592, filed on Jan. 9, 2001.

(51) Int. Cl.
*A61M 25/00* (2006.01)
*A61M 25/14* (2006.01)
*A61M 37/00* (2006.01)

(52) U.S. Cl.
USPC ............... 604/6.16; 604/27; 604/28; 604/43; 604/93.01; 604/264

(58) Field of Classification Search
USPC .................. 604/6.01, 4.01, 6.16, 27, 48, 264, 604/523; 623/1.1, 66.1; 248/74.1, 75, 200, 248/694; 40/326, 642.02, 662, 671, 672, 40/673, 674, 607.13; 24/542, 545, 568, 557, 24/597
See application file for complete search history.

(56) References Cited

U.S. PATENT DOCUMENTS

| | | | |
|---|---|---|---|
| 1,248,492 A | 12/1917 | Hill | |
| 2,024,982 A | 12/1935 | Scott | |
| 2,460,473 A | 2/1949 | Smith | |
| 3,336,927 A | 8/1967 | Klebanoff | |
| 3,411,534 A | 11/1968 | Rose | |
| 3,680,562 A | 8/1972 | Wittes et al. | |
| 3,815,608 A * | 6/1974 | Spinosa et al. | 604/105 |
| 3,833,003 A | 9/1974 | Tarricco | |
| 3,929,126 A * | 12/1975 | Corsaut | 604/43 |
| 3,938,530 A | 2/1976 | Santomieri | |

(Continued)

FOREIGN PATENT DOCUMENTS

| | | |
|---|---|---|
| DE | 2590645 | 5/1987 |
| EP | 0301854 | 2/1989 |

(Continued)

*Primary Examiner* — Adam Marcetich
(74) *Attorney, Agent, or Firm* — Neil D. Gershon

(57) ABSTRACT

A medical catheter comprising a first return lumen, a plurality of withdrawal lumens, a first clamping member and a plurality of intake extension tubes. Each intake extension tube communicates with an intake lumen of the catheter to provide fluid communication with the respective intake lumens. The intake extension tubes are positioned in a stacked arrangement, and the clamping member has a plurality of posts to receive the stacked tubes to limit lateral movement thereof.

21 Claims, 46 Drawing Sheets

U.S. PATENT DOCUMENTS

| | | | |
|---|---|---|---|
| 4,129,129 A * | 12/1978 | Amrine | 600/16 |
| 4,134,402 A | 1/1979 | Mahurkar | |
| 4,178,936 A | 12/1979 | Newcomb | |
| 4,180,068 A | 12/1979 | Jacobsen et al. | |
| 4,270,535 A | 6/1981 | Bogue et al. | |
| 4,299,228 A | 11/1981 | Peters | |
| D270,282 S | 8/1983 | Gross | |
| 4,398,910 A | 8/1983 | Blake et al. | |
| 4,403,983 A | 9/1983 | Edelman et al. | |
| 4,406,656 A | 9/1983 | Hattler et al. | |
| 4,431,426 A | 2/1984 | Groshong et al. | |
| 4,432,752 A | 2/1984 | Marlon | |
| 4,439,179 A | 3/1984 | Lueders et al. | |
| 4,451,252 A | 5/1984 | Martin | |
| 4,453,928 A | 6/1984 | Steiger | |
| D275,519 S | 9/1984 | Ismail | |
| 4,479,792 A | 10/1984 | Lazarus et al. | |
| 4,490,136 A | 12/1984 | Ekbladh et al. | |
| 4,493,696 A | 1/1985 | Uldall | |
| 4,511,163 A | 4/1985 | Harris et al. | |
| 4,543,087 A | 9/1985 | Sommercorn et al. | |
| 4,545,373 A | 10/1985 | Christoudias | |
| 4,568,329 A | 2/1986 | Mahurkar | |
| 4,574,806 A | 3/1986 | McCarthy | |
| 4,581,012 A | 4/1986 | Brown et al. | |
| 4,583,968 A | 4/1986 | Mahurkar | |
| 4,610,670 A | 9/1986 | Spencer | |
| 4,619,643 A | 10/1986 | Bai | |
| 4,623,327 A | 11/1986 | Mahurkar | |
| 4,639,252 A | 1/1987 | Kelly et al. | |
| 4,643,711 A | 2/1987 | Bates | |
| 4,668,221 A | 5/1987 | Luther | |
| 4,670,009 A | 6/1987 | Bullock | |
| 4,682,978 A | 7/1987 | Martin | |
| 4,717,379 A | 1/1988 | Ekholmer | |
| 4,738,667 A | 4/1988 | Galloway | |
| 4,753,640 A | 6/1988 | Nichols et al. | |
| 4,762,120 A | 8/1988 | Hussein | |
| 4,769,016 A | 9/1988 | Labianca | |
| 4,776,841 A | 10/1988 | Catalano | |
| 4,808,155 A | 2/1989 | Mahurkar | |
| 4,808,163 A | 2/1989 | Laub | |
| 4,832,687 A | 5/1989 | Smith | |
| 4,838,881 A | 6/1989 | Bennett | |
| 4,842,582 A | 6/1989 | Mahurkar | |
| 4,846,804 A | 7/1989 | Davis et al. | |
| 4,894,057 A | 1/1990 | Howes | |
| 4,895,561 A | 1/1990 | Mahurkar | |
| 4,902,276 A | 2/1990 | Zakko | |
| 4,904,238 A | 2/1990 | Williams | |
| 4,927,418 A | 5/1990 | Dake et al. | |
| 4,950,259 A | 8/1990 | Geary et al. | |
| 4,961,809 A | 10/1990 | Martin | |
| 4,968,307 A | 11/1990 | Dake et al. | |
| 4,976,684 A | 12/1990 | Broadnax, Jr. | |
| 4,994,027 A | 2/1991 | Farrell | |
| 4,995,865 A | 2/1991 | Gahara et al. | |
| 5,009,636 A | 4/1991 | Wortley et al. | |
| 5,021,044 A | 6/1991 | Sharkawy | |
| D318,123 S | 7/1991 | Yokoyama et al. | |
| 5,041,084 A * | 8/1991 | DeVries et al. | 604/43 |
| 5,053,004 A | 10/1991 | Markel et al. | |
| 5,053,023 A | 10/1991 | Martin | |
| 5,057,073 A | 10/1991 | Martin | |
| 5,057,075 A | 10/1991 | Moncrief et al. | |
| 5,059,170 A | 10/1991 | Cameron | |
| 5,078,699 A | 1/1992 | Haber et al. | |
| 5,092,848 A | 3/1992 | deCiutiis | |
| 5,098,413 A | 3/1992 | Trudell et al. | |
| 5,122,125 A | 6/1992 | Deuss | |
| 5,135,599 A | 8/1992 | Martin et al. | |
| 5,139,486 A | 8/1992 | Moss | |
| 5,156,592 A | 10/1992 | Martin et al. | |
| 5,167,623 A | 12/1992 | Cianci et al. | |
| 5,171,216 A | 12/1992 | Dasse et al. | |
| 5,195,962 A | 3/1993 | Martin et al. | |
| 5,207,648 A | 5/1993 | Gross | |
| 5,207,650 A | 5/1993 | Martin | |
| 5,209,723 A | 5/1993 | Twardowski et al. | |
| 5,209,742 A | 5/1993 | Venema et al. | |
| 5,215,527 A | 6/1993 | Beck et al. | |
| 5,221,255 A | 6/1993 | Mahurkar et al. | |
| 5,221,256 A | 6/1993 | Mahurkar | |
| 5,234,438 A | 8/1993 | Semrad | |
| 5,246,430 A | 9/1993 | MacFarlane | |
| 5,250,038 A | 10/1993 | Melker et al. | |
| 5,273,527 A | 12/1993 | Schatz et al. | |
| 5,279,596 A | 1/1994 | Castaneda et al. | |
| 5,324,274 A | 6/1994 | Martin | |
| 5,334,139 A | 8/1994 | Jeppsson | |
| 5,338,293 A | 8/1994 | Jeppsson et al. | |
| 5,346,471 A | 9/1994 | Raulerson | |
| 5,348,536 A | 9/1994 | Young et al. | |
| 5,350,358 A | 9/1994 | Martin | |
| 5,360,397 A | 11/1994 | Pinchuk | |
| 5,364,344 A | 11/1994 | Beattie et al. | |
| 5,374,245 A | 12/1994 | Mahurkar | |
| 5,378,230 A | 1/1995 | Mahurkar | |
| 5,380,276 A | 1/1995 | Miller et al. | |
| 5,380,290 A | 1/1995 | Makower et al. | |
| 5,382,238 A | 1/1995 | Abrahamson et al. | |
| 5,395,316 A | 3/1995 | Martin | |
| 5,403,291 A | 4/1995 | Abrahamson | |
| 5,405,320 A | 4/1995 | Twardowski et al. | |
| 5,405,341 A | 4/1995 | Martin | |
| 5,431,661 A | 7/1995 | Koch | |
| 5,451,206 A | 9/1995 | Young | |
| 5,468,159 A | 11/1995 | Brodsky et al. | |
| 5,472,417 A | 12/1995 | Martin et al. | |
| 5,480,380 A | 1/1996 | Martin | |
| 5,486,159 A | 1/1996 | Mahurkar | |
| 5,489,278 A | 2/1996 | Abrahamson | |
| 5,509,897 A | 4/1996 | Twardowski et al. | |
| 5,509,900 A | 4/1996 | Kirkman | |
| 5,542,925 A | 8/1996 | Orth | |
| 5,556,390 A | 9/1996 | Hicks | |
| 5,569,182 A | 10/1996 | Twardowski et al. | |
| 5,571,093 A | 11/1996 | Cruz et al. | |
| 5,662,606 A | 9/1997 | Cimino et al. | |
| 5,693,030 A | 12/1997 | Lee et al. | |
| 5,702,365 A | 12/1997 | King | |
| 5,707,362 A | 1/1998 | Yoon | |
| 5,713,849 A | 2/1998 | Bosma et al. | |
| 5,718,678 A | 2/1998 | Fleming, III | |
| 5,752,939 A | 5/1998 | Makoto | |
| 5,792,123 A | 8/1998 | Ensminger | |
| 5,797,869 A | 8/1998 | Leblanc et al. | |
| 5,807,311 A | 9/1998 | Palestrant | |
| 5,807,317 A | 9/1998 | Krech, Jr. | |
| 5,807,329 A | 9/1998 | Gelman | |
| 5,810,789 A | 9/1998 | Powers et al. | |
| 5,830,196 A | 11/1998 | Hicks | |
| 5,882,347 A | 3/1999 | Mouris-Laan et al. | |
| 5,911,715 A | 6/1999 | Berg et al. | |
| 5,913,848 A | 6/1999 | Luther et al. | |
| 5,916,208 A | 6/1999 | Luther et al. | |
| 5,919,160 A | 7/1999 | Sanfilippo | |
| 5,944,732 A | 8/1999 | Raulerson et al. | |
| 5,947,953 A | 9/1999 | Ash et al. | |
| 5,957,893 A | 9/1999 | Luther et al. | |
| 5,961,486 A | 10/1999 | Twardowski et al. | |
| 5,976,103 A | 11/1999 | Martin | |
| 5,976,120 A | 11/1999 | Chow et al. | |
| 5,984,908 A | 11/1999 | Davis et al. | |
| 5,989,206 A | 11/1999 | Prosl et al. | |
| 5,989,213 A | 11/1999 | Maginot | |
| 6,001,079 A | 12/1999 | Pourchez | |
| 6,010,480 A | 1/2000 | Abele et al. | |
| 6,036,654 A | 3/2000 | Quinn | |
| 6,059,771 A | 5/2000 | Balbierz et al. | |
| 6,106,540 A | 8/2000 | White et al. | |
| 6,110,185 A * | 8/2000 | Barra et al. | 606/148 |
| 6,120,494 A | 9/2000 | Jonkman | |
| 6,126,631 A | 10/2000 | Loggie | |
| 6,132,405 A | 10/2000 | Nilsson et al. | |
| 6,146,354 A | 11/2000 | Beil | |
| 6,146,373 A | 11/2000 | Cragg et al. | |

| | | |
|---|---|---|
| 6,152,909 A | 11/2000 | Bagaoisan et al. |
| 6,156,016 A | 12/2000 | Maginot |
| 6,180,059 B1 | 1/2001 | Divino, Jr. et al. |
| 6,190,349 B1 | 2/2001 | Ash et al. |
| 6,190,371 B1 | 2/2001 | Maginot et al. |
| 6,193,685 B1 | 2/2001 | Goodin |
| 6,196,996 B1 | 3/2001 | Teirstein |
| 6,206,849 B1 | 3/2001 | Martin et al. |
| 6,210,365 B1 | 4/2001 | Afzal |
| 6,210,370 B1 | 4/2001 | Chi-Sing et al. |
| 6,223,070 B1 | 4/2001 | Chait |
| 6,264,627 B1 | 7/2001 | Liska et al. |
| 6,270,490 B1 | 8/2001 | Hahnen |
| 6,273,879 B1 | 8/2001 | Keith et al. |
| 6,280,423 B1 | 8/2001 | Davey et al. |
| 6,293,927 B1 | 9/2001 | McGuckin, Jr. |
| 6,293,958 B1 | 9/2001 | Berry et al. |
| 6,296,631 B2 | 10/2001 | Chow |
| 6,328,730 B1 | 12/2001 | Harkrider, Jr. |
| 6,346,093 B1 | 2/2002 | Allman et al. |
| 6,350,252 B2 | 2/2002 | Ray et al. |
| 6,358,229 B1 | 3/2002 | Tihon |
| 6,361,529 B1 | 3/2002 | Goodin et al. |
| 6,394,141 B2 | 5/2002 | Wages et al. |
| 6,454,997 B1 | 9/2002 | Divino, Jr. et al. |
| 6,595,966 B2 | 7/2003 | Davey et al. |
| 6,638,242 B2 | 10/2003 | Wilson et al. |
| 6,692,466 B1 | 2/2004 | Chow et al. |
| 6,749,574 B2 | 6/2004 | O'Keefe |
| 6,758,836 B2 | 7/2004 | Zawacki |
| 6,758,857 B2 | 7/2004 | Cioanta et al. |
| 6,780,175 B1 * | 8/2004 | Sachdeva et al. ............. 604/531 |
| 6,786,884 B1 | 9/2004 | DeCant, Jr. et al. |
| 6,814,718 B2 | 11/2004 | McGuckin et al. |
| 6,821,265 B1 | 11/2004 | Bertolero et al. |
| 6,823,617 B2 | 11/2004 | Schweikert |
| 6,827,710 B1 | 12/2004 | Mooney et al. |
| 6,890,321 B2 | 5/2005 | Luther et al. |
| 6,921,396 B1 | 7/2005 | Wilson et al. |
| 6,942,635 B2 | 9/2005 | Rosenblatt et al. |
| 6,969,095 B2 | 11/2005 | Rittenhouse |
| 6,969,381 B2 | 11/2005 | Voorhees |
| 6,974,434 B2 | 12/2005 | Roberts et al. |
| 6,994,700 B2 | 2/2006 | Elkins et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,060,060 B1 | 6/2006 | Simpson et al. |
| 7,077,829 B2 | 7/2006 | McGuckin, Jr. et al. |
| 7,128,734 B1 | 10/2006 | Wilson et al. |
| 7,229,429 B2 | 6/2007 | Martin et al. |
| 7,300,430 B2 | 11/2007 | Wilson et al. |
| 7,322,953 B2 | 1/2008 | Redinger |
| 2002/0055714 A1 | 5/2002 | Rothschild |
| 2002/0087145 A1 | 7/2002 | Ehwald et al. |
| 2003/0023198 A1 | 1/2003 | Twardowski |
| 2003/0066218 A1 | 4/2003 | Schweikert |
| 2003/0088213 A1 | 5/2003 | Schweikert |
| 2003/0093027 A1 | 5/2003 | McGuckin et al. |
| 2003/0153898 A1 | 8/2003 | Schon et al. |
| 2003/0204179 A1 | 10/2003 | Davey et al. |
| 2003/0225365 A1 | 12/2003 | Greff et al. |
| 2004/0064086 A1 | 4/2004 | Gottlieb et al. |
| 2004/0193103 A1 | 9/2004 | Kumar |
| 2004/0249337 A1 | 12/2004 | DiFiore |
| 2005/0187535 A1 | 8/2005 | Wilson et al. |
| 2006/0004325 A1 | 1/2006 | Hamatake et al. |
| 2006/0047268 A1 | 3/2006 | Stephens |
| 2006/0135949 A1 | 6/2006 | Rome et al. |
| 2006/0206048 A1 | 9/2006 | Loggie |
| 2006/0270962 A1 | 11/2006 | McGuckin et al. |
| 2007/0149919 A1 | 6/2007 | Perkins et al. |
| 2008/0312578 A1 | 12/2008 | DeFonzo et al. |
| 2010/0145285 A1 | 6/2010 | Bosel |

FOREIGN PATENT DOCUMENTS

| | | |
|---|---|---|
| EP | 0691139 | 1/1996 |
| EP | 0799627 | 10/1997 |
| EP | 0995461 | 4/2000 |
| EP | 1905476 | 4/2008 |
| ER | 0440992 | 8/1991 |
| WO | 9737699 | 10/1997 |
| WO | 9824501 | 6/1998 |
| WO | 0074760 | 12/2000 |
| WO | 0176677 | 10/2001 |
| WO | 2004036102 | 4/2004 |

\* cited by examiner

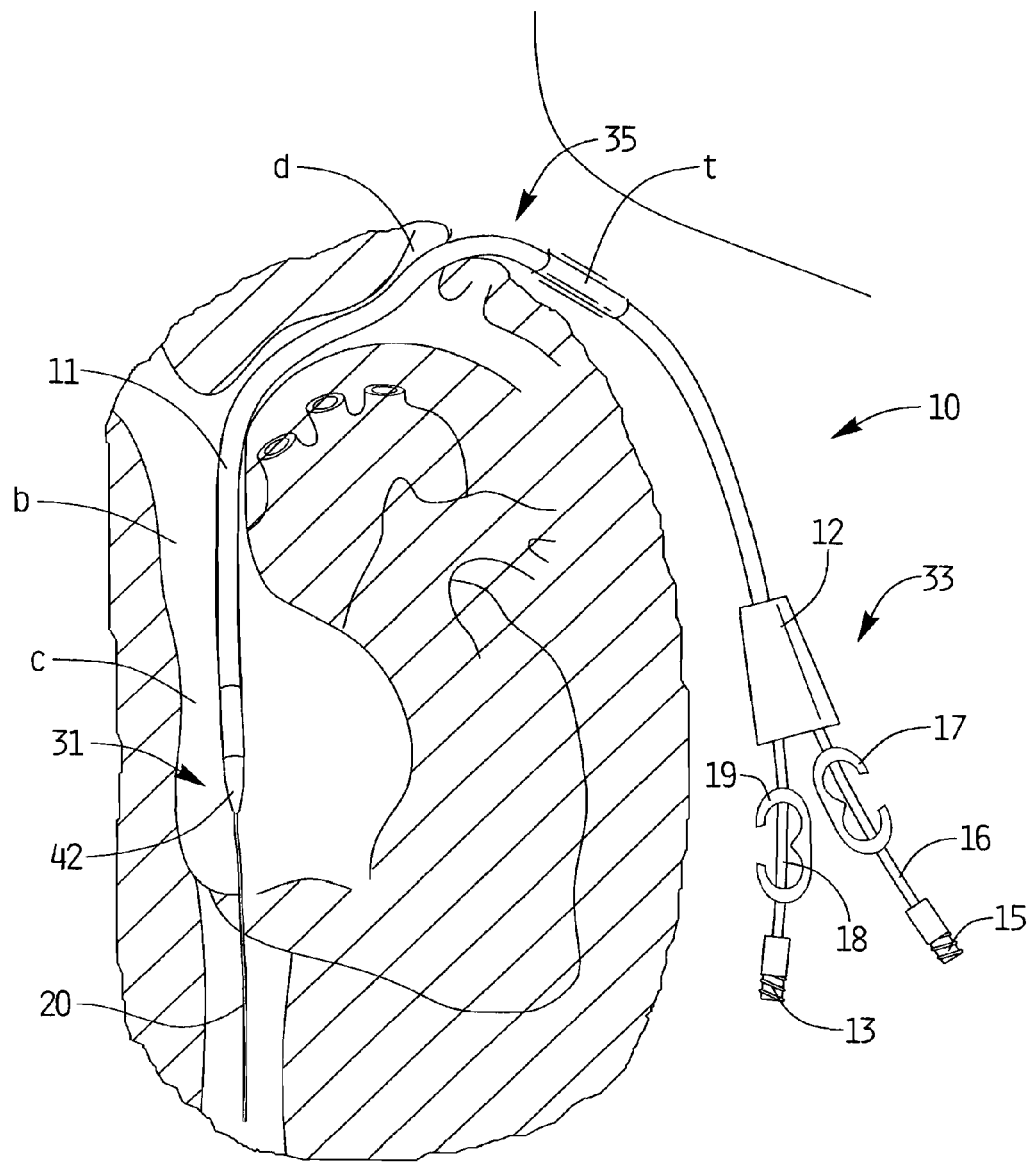
FIG_2

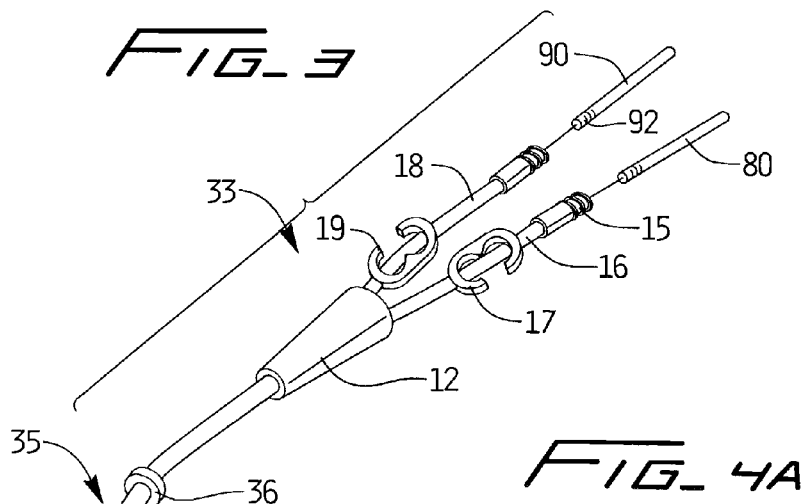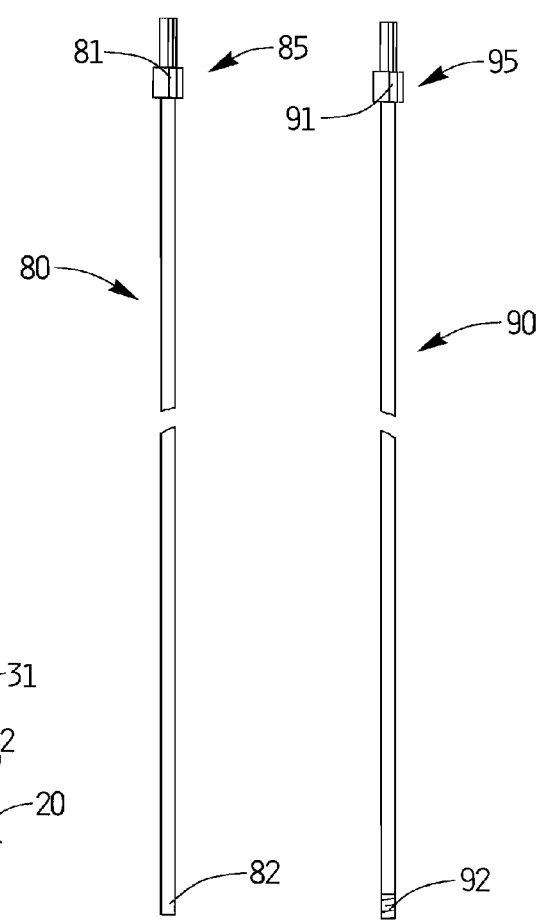

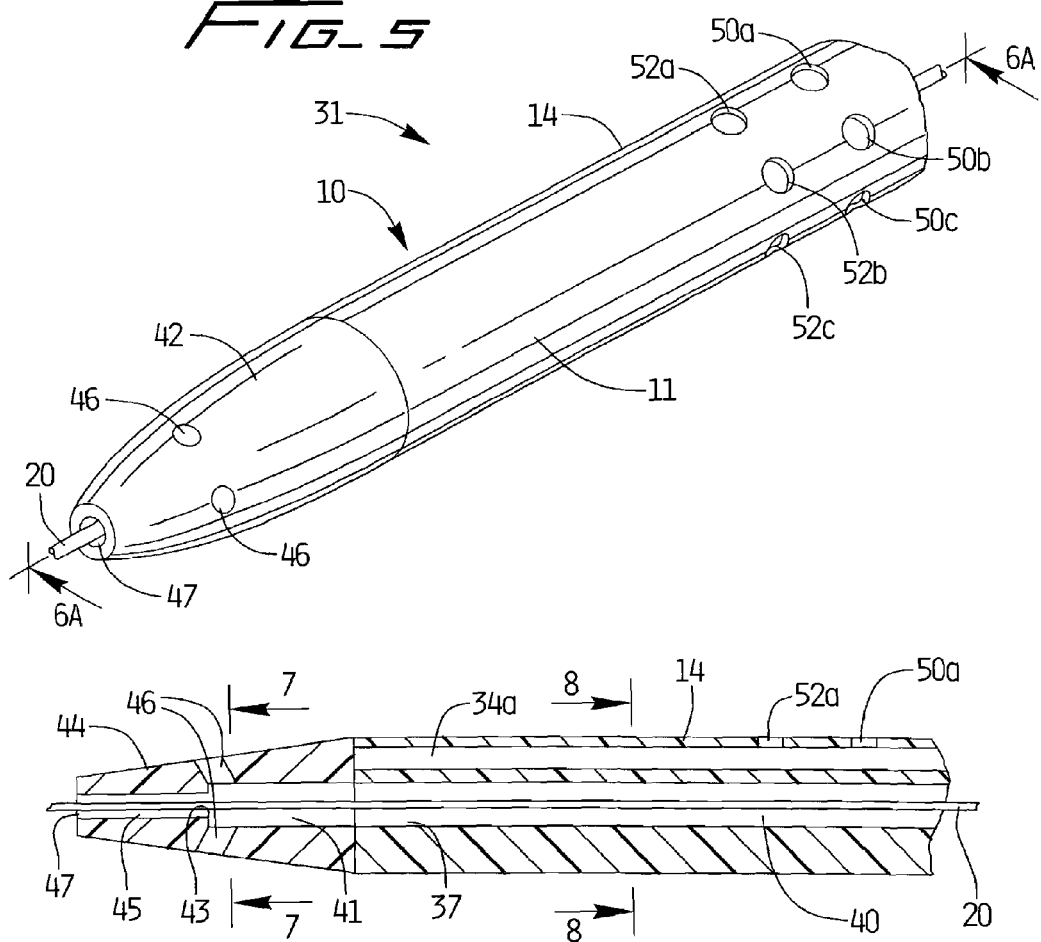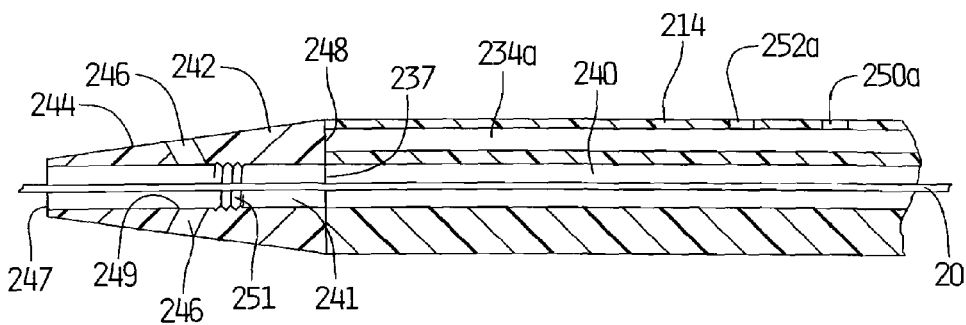

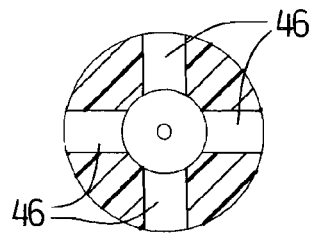
FIG_7
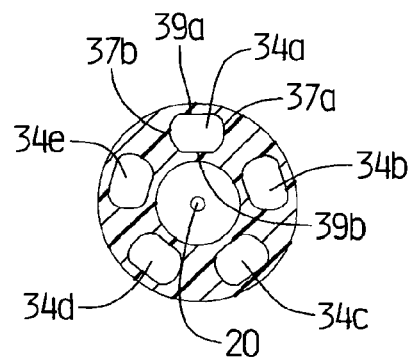
FIG_8
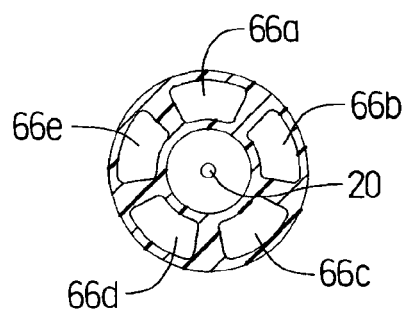
FIG_9A
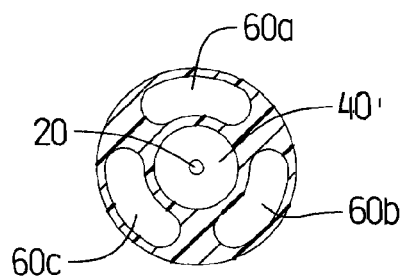
FIG_9B
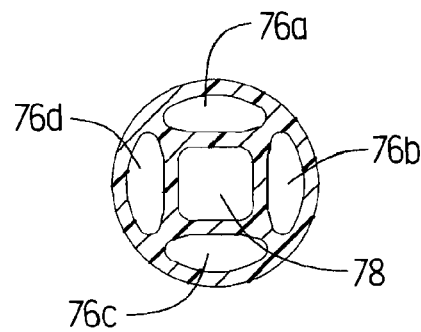
FIG_9C
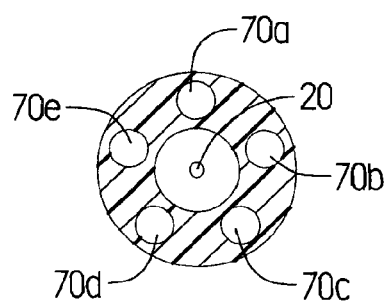
FIG_10

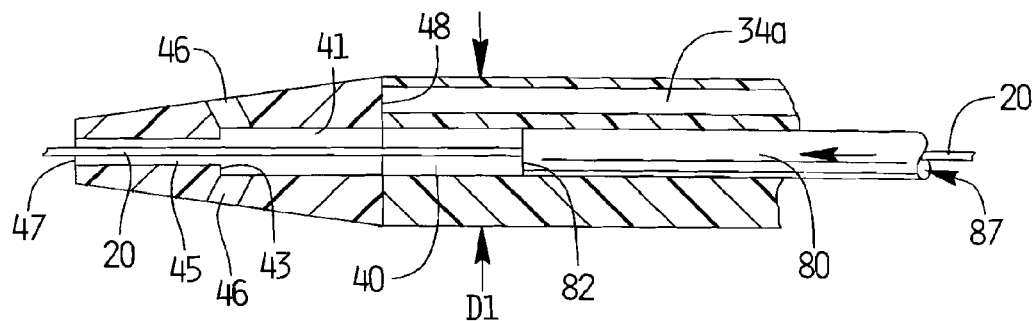
FIG_11
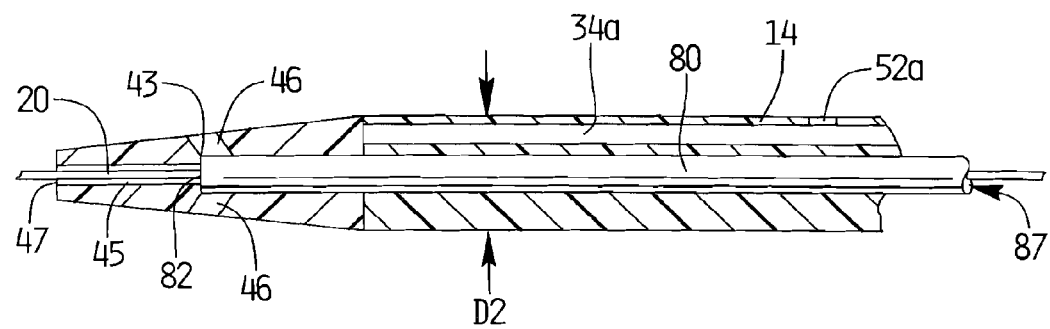
FIG_12

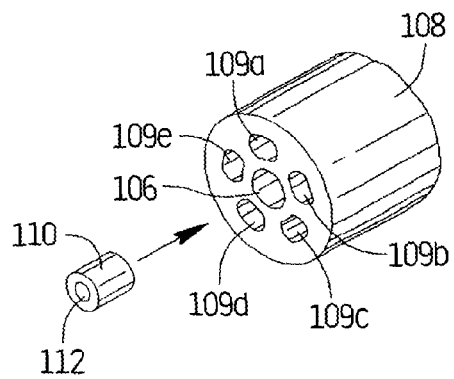 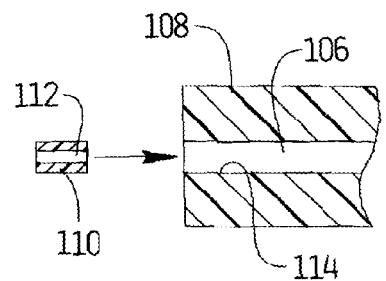
FIG_13A    FIG_13B
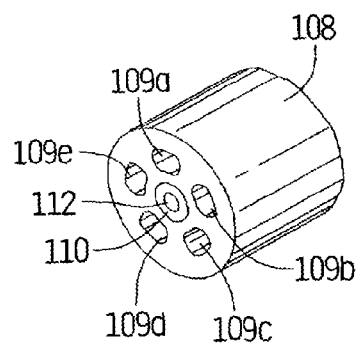 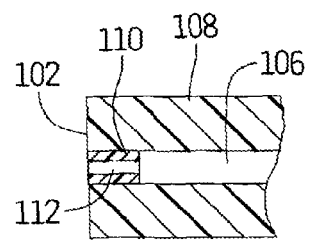
FIG_14A    FIG_14B
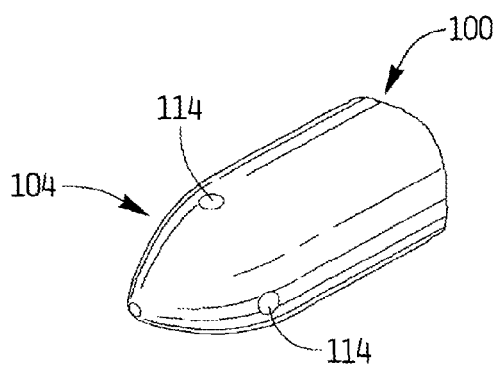 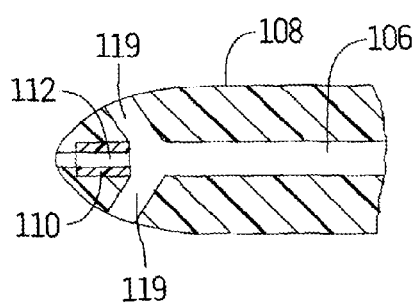
FIG_15A    FIG_15B

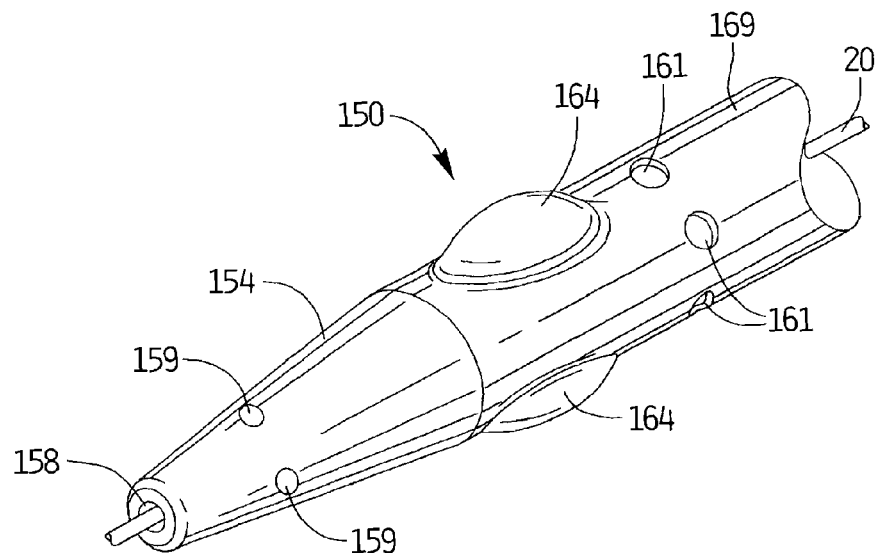
FIG_16A
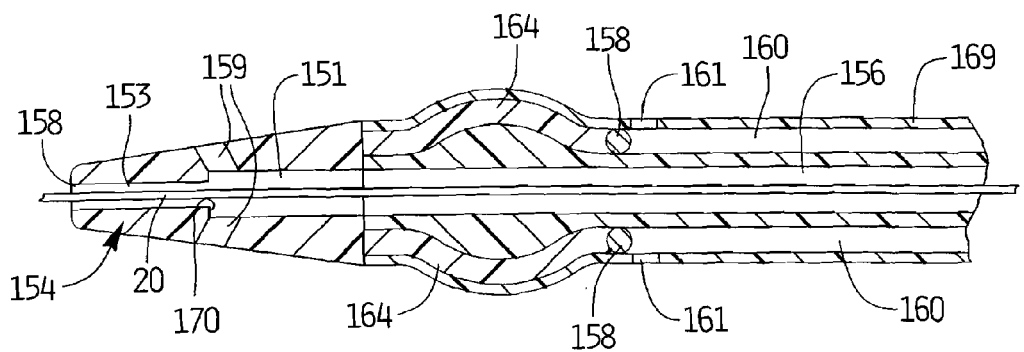
FIG_16B
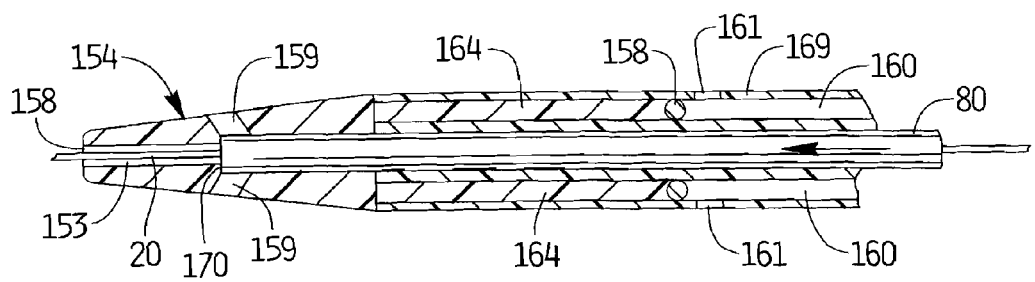
FIG_16C

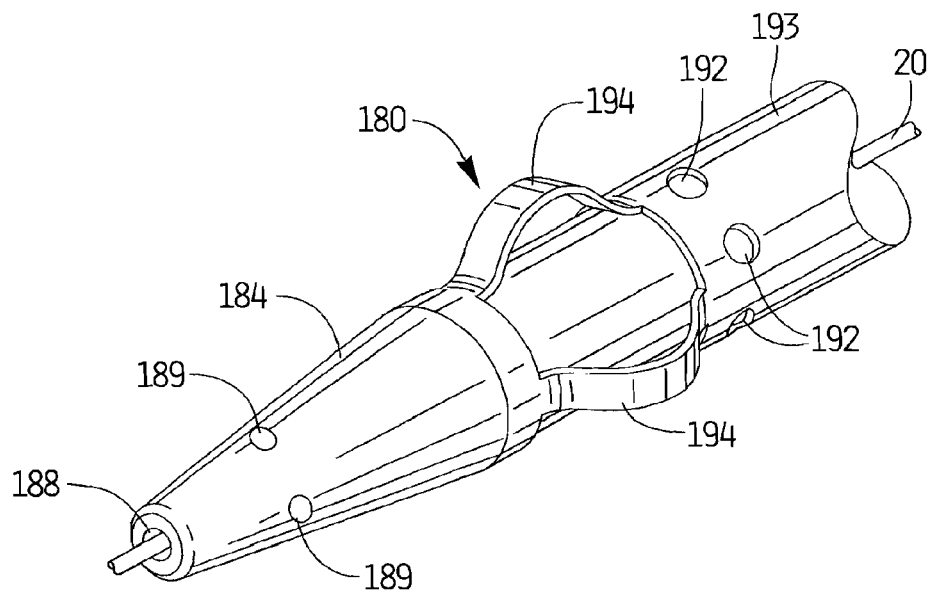
FIG_17A
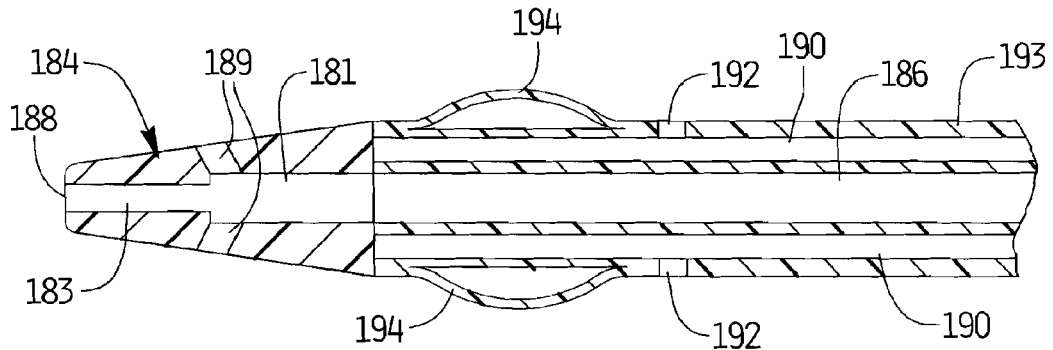
FIG_17B
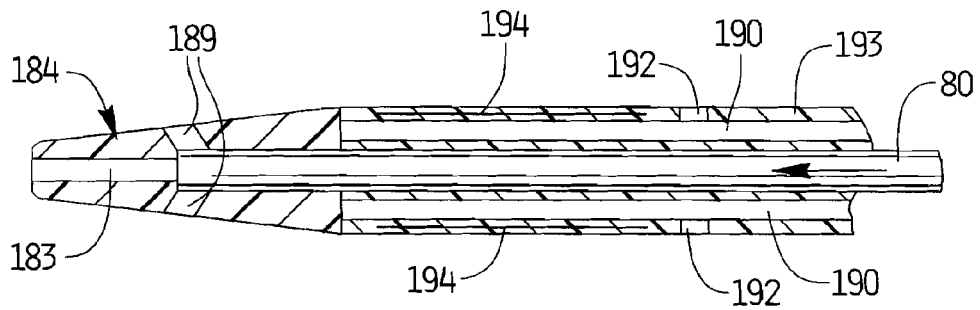
FIG_17C

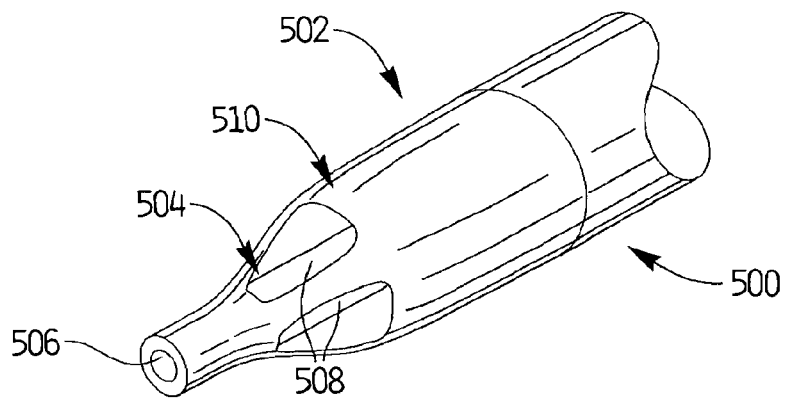
FIG_18
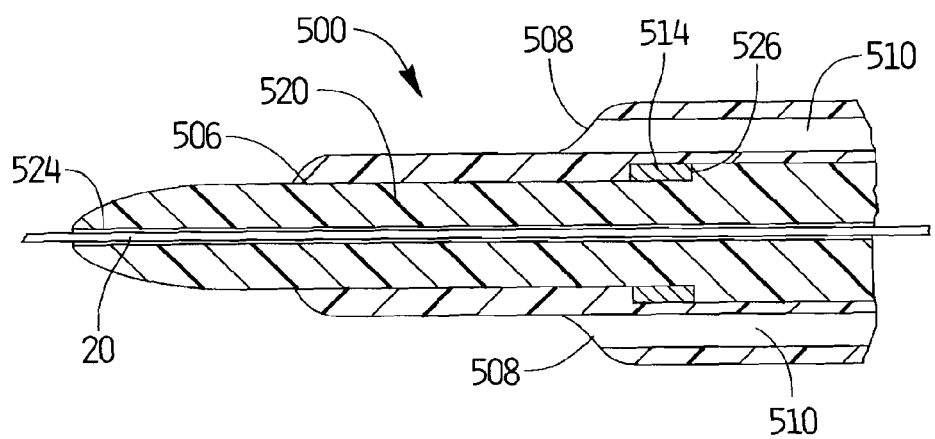
FIG_19
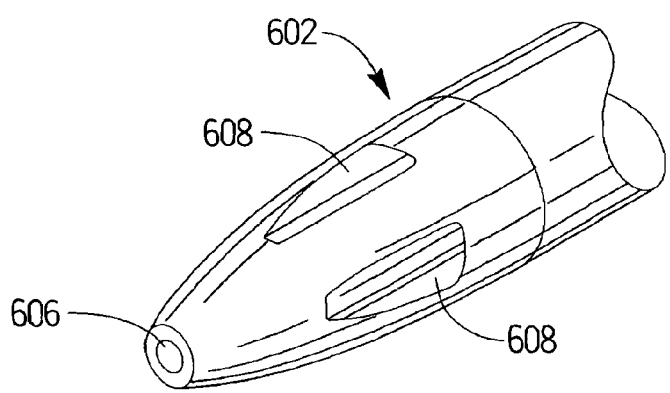
FIG_20

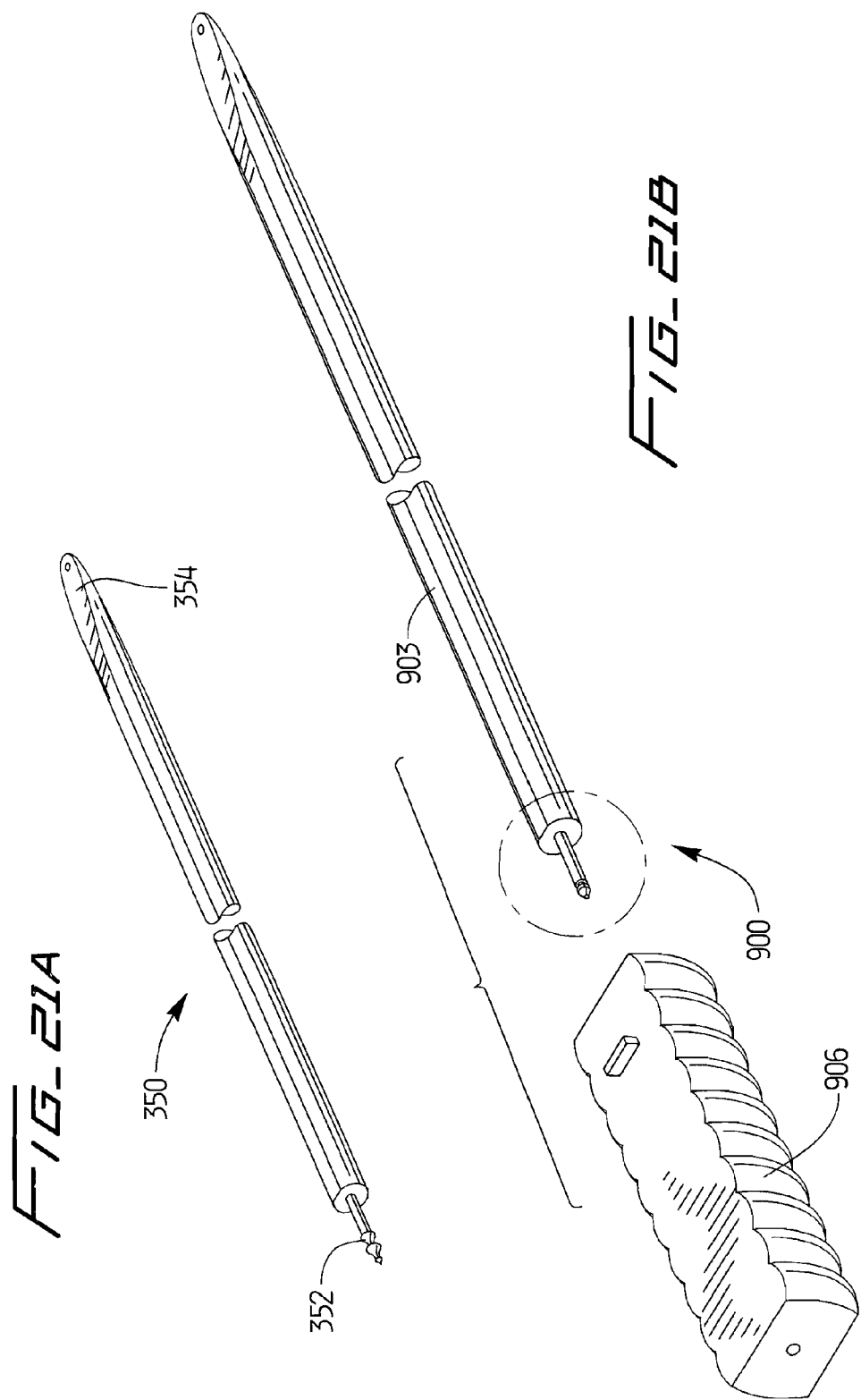

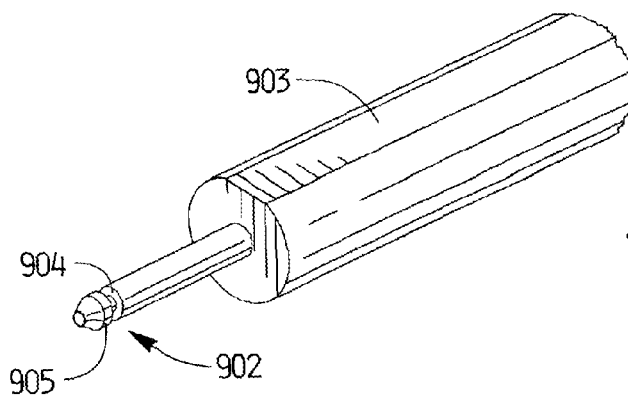
FIG_21C
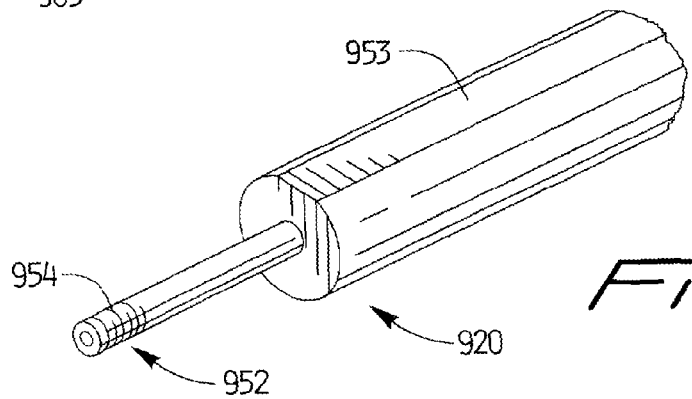
FIG_21D
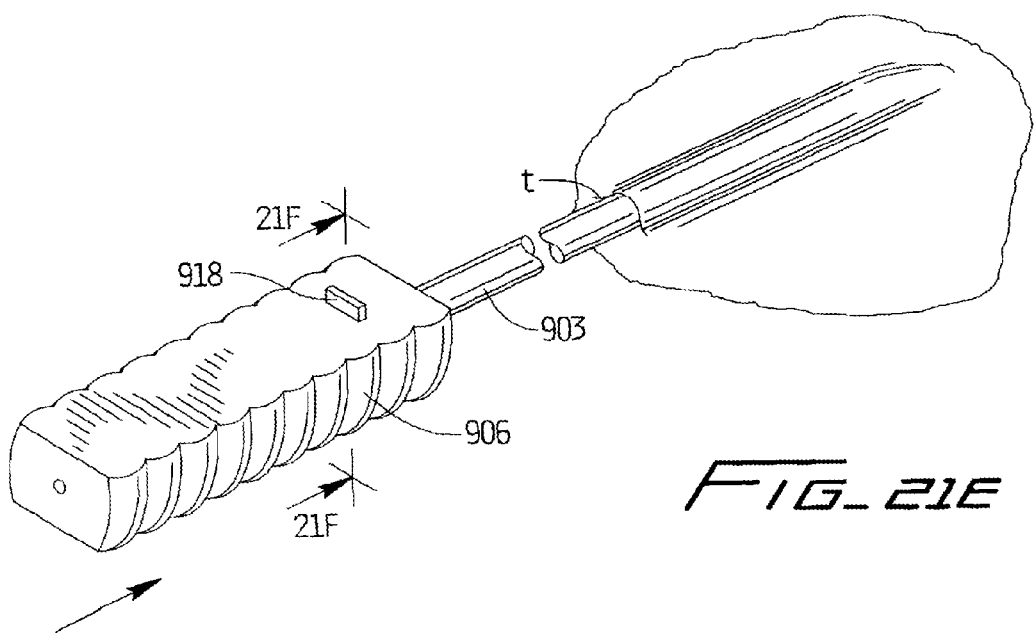
FIG_21E

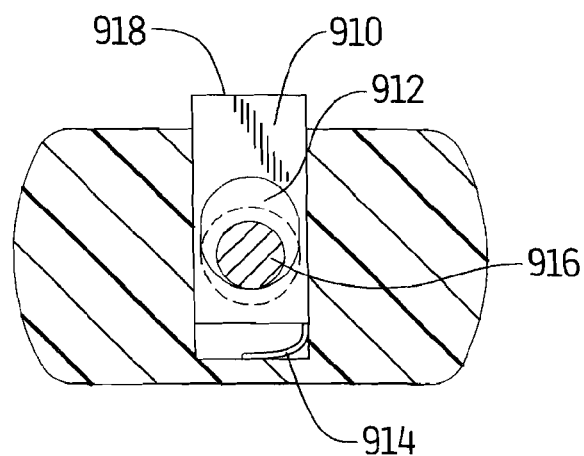
FIG_21F
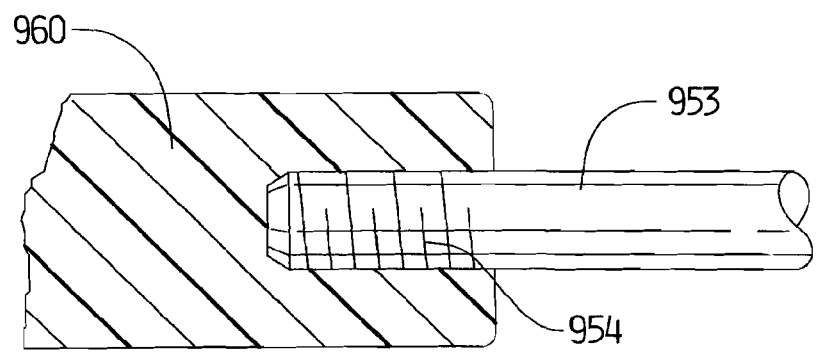
FIG_21G
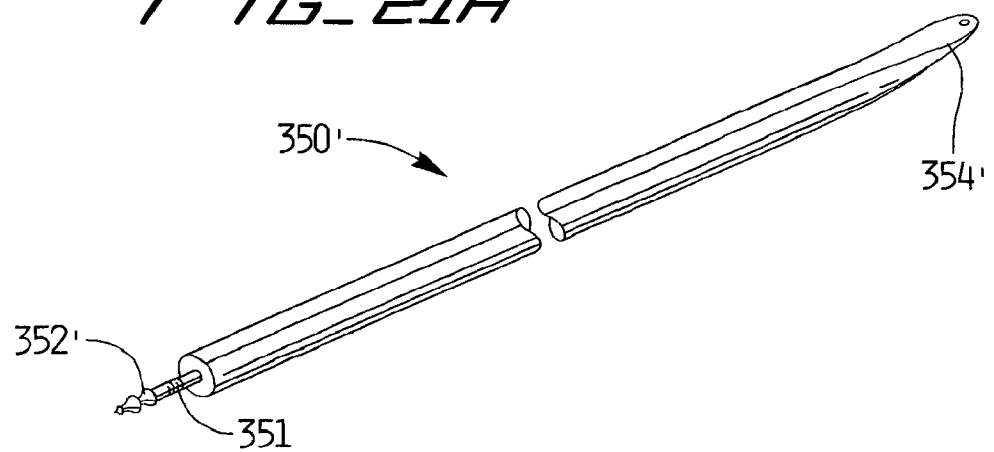
FIG_21H

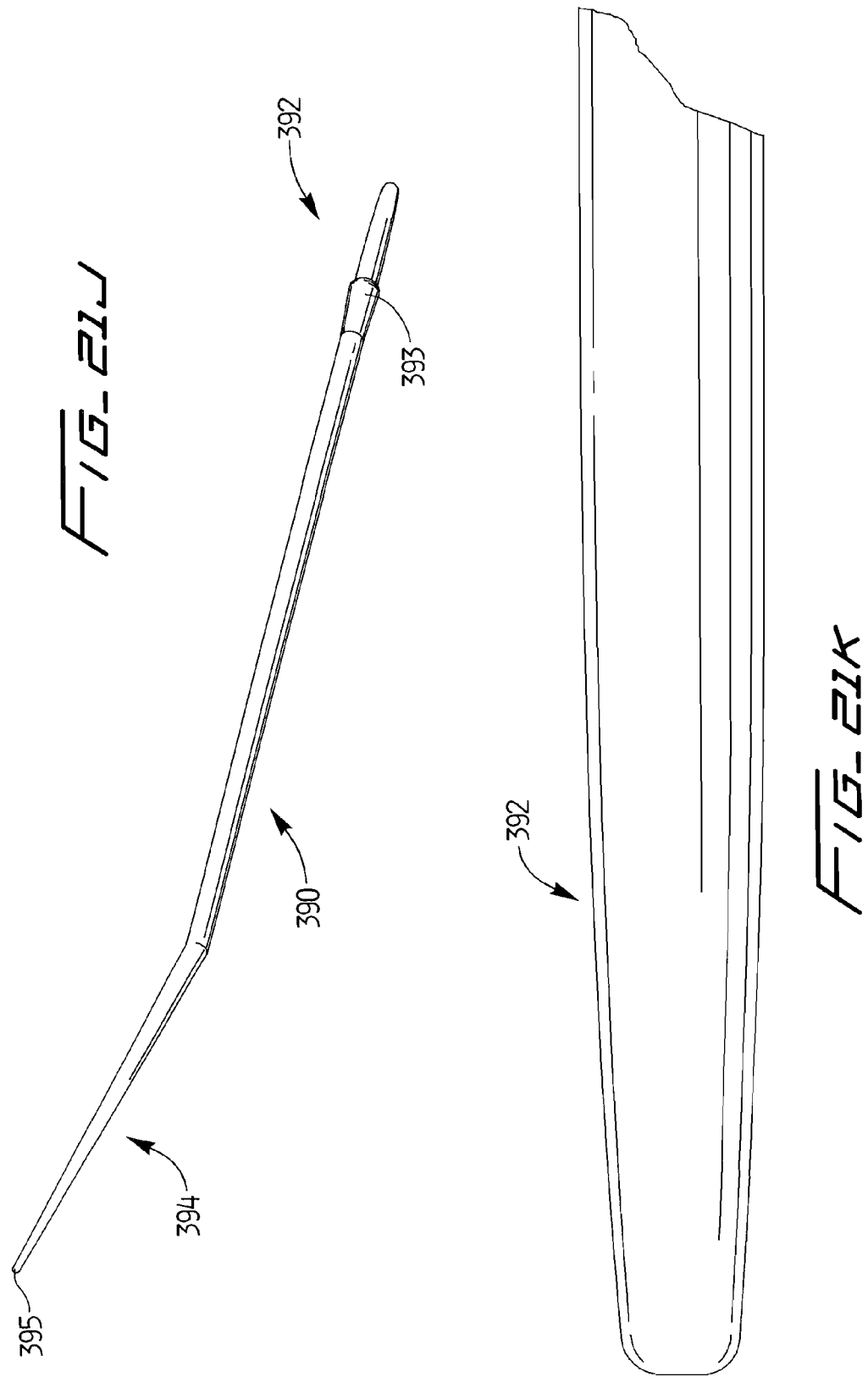

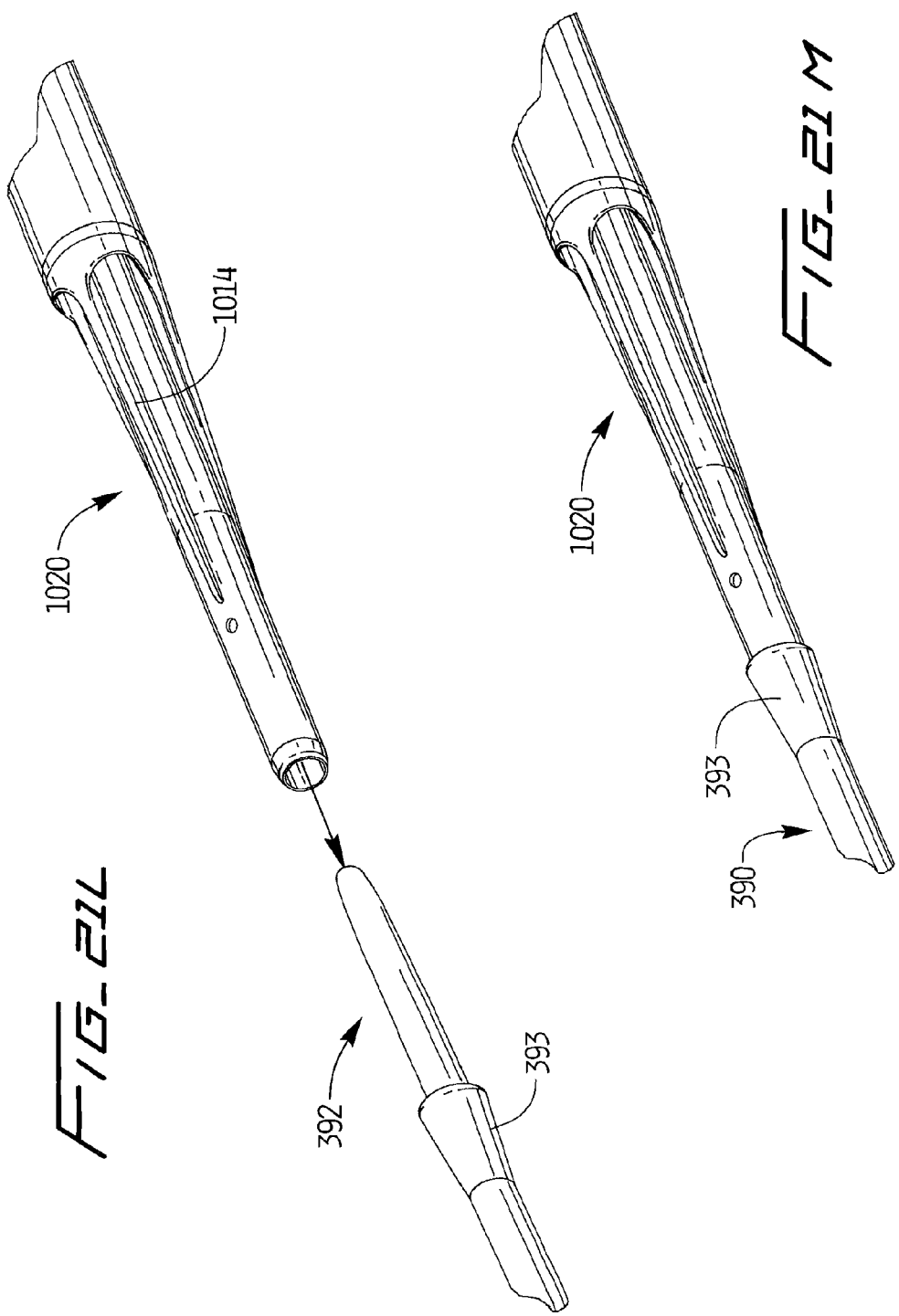

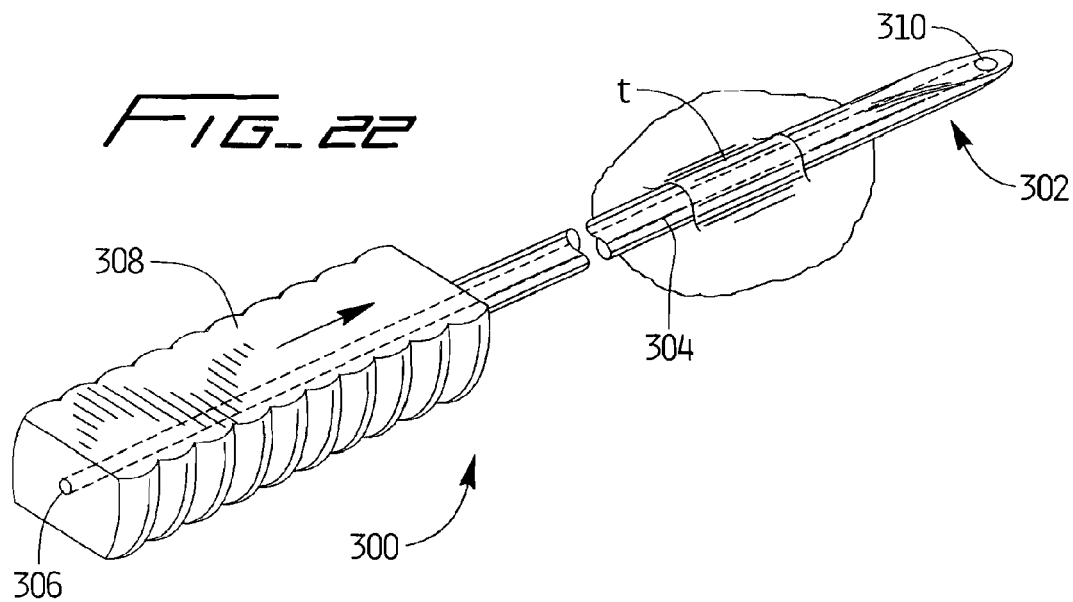
FIG_22
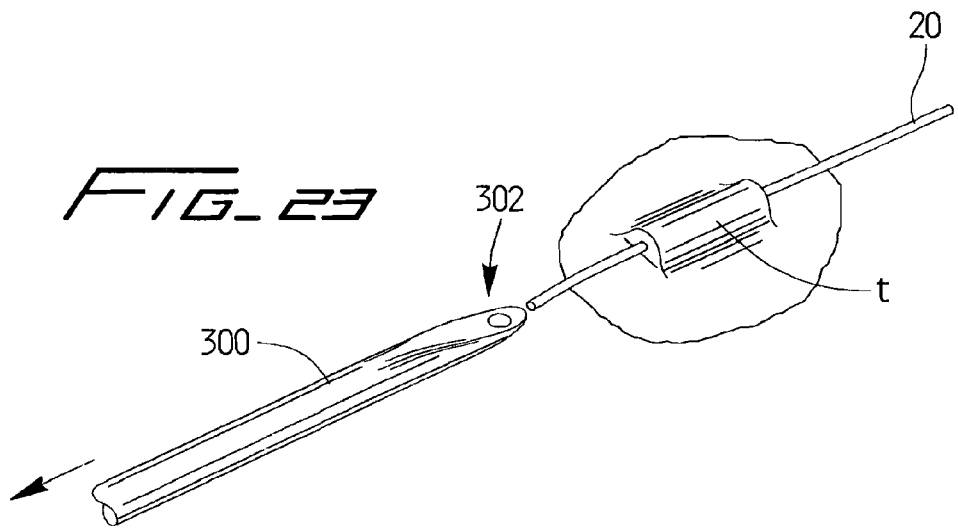
FIG_23

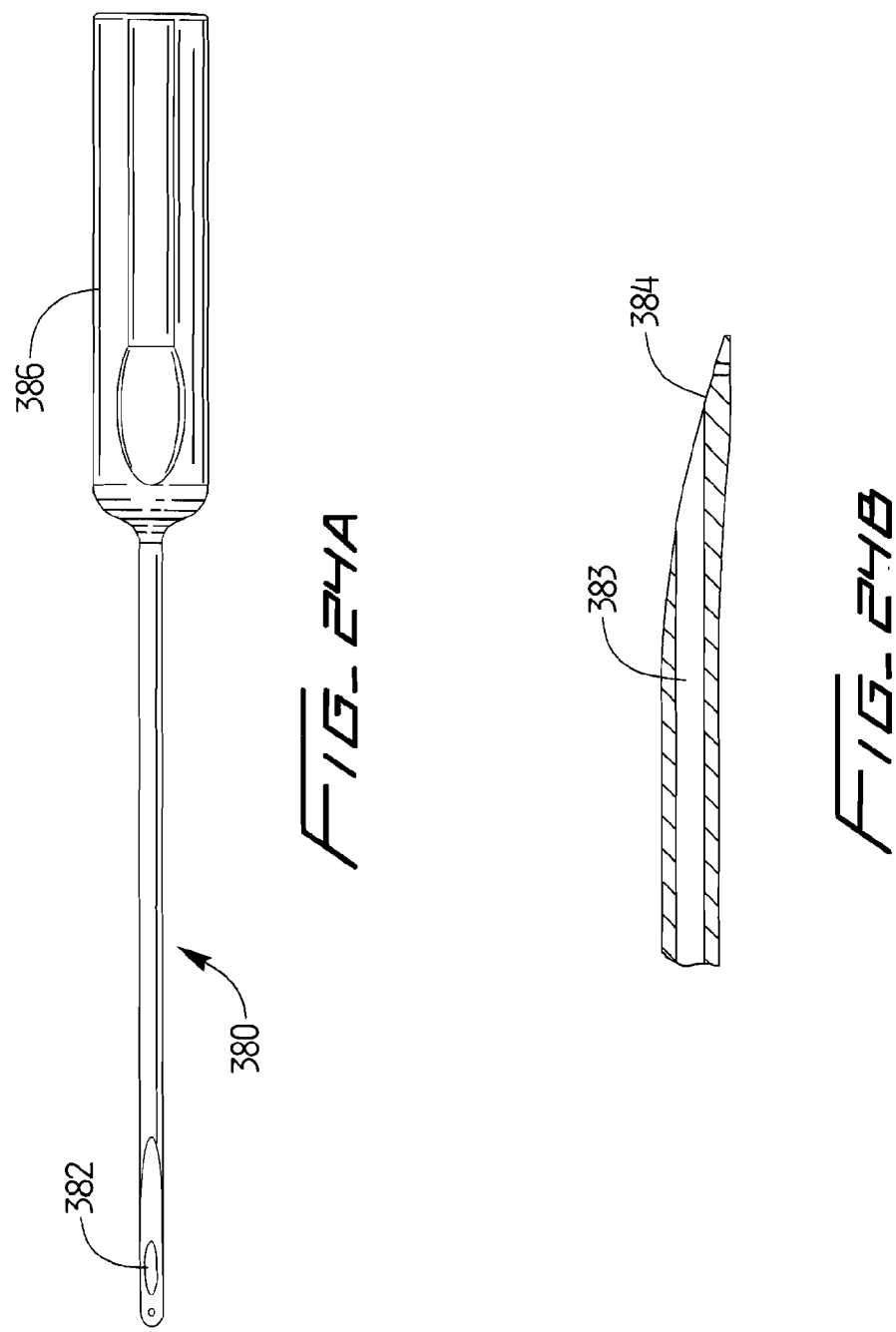

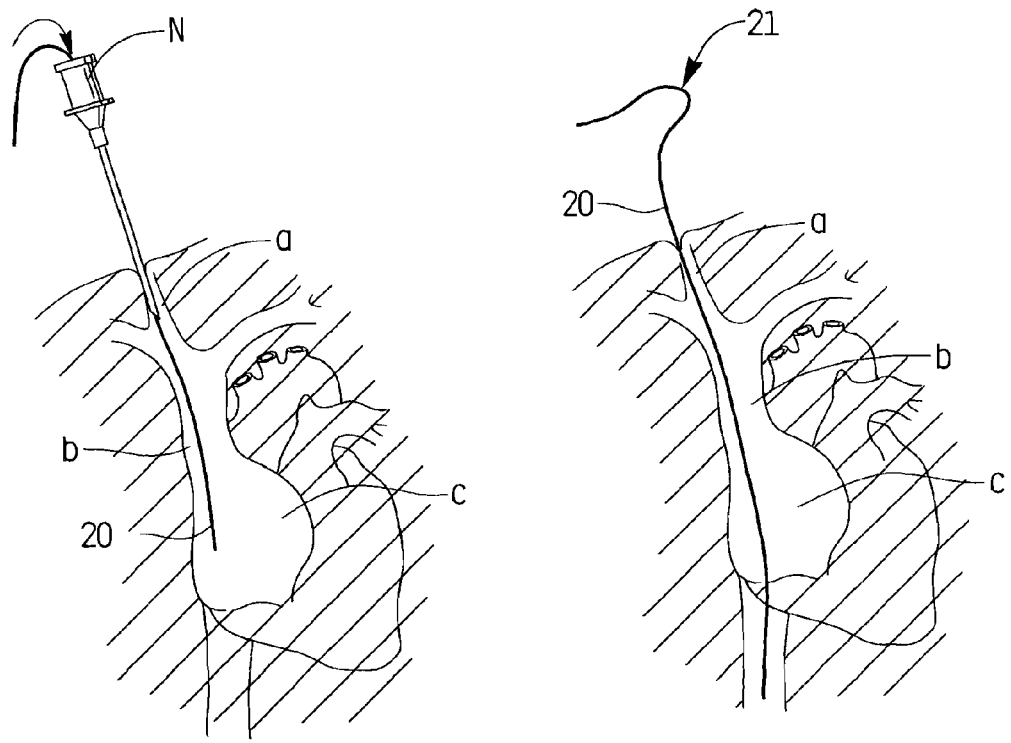
FIG_25   FIG_26
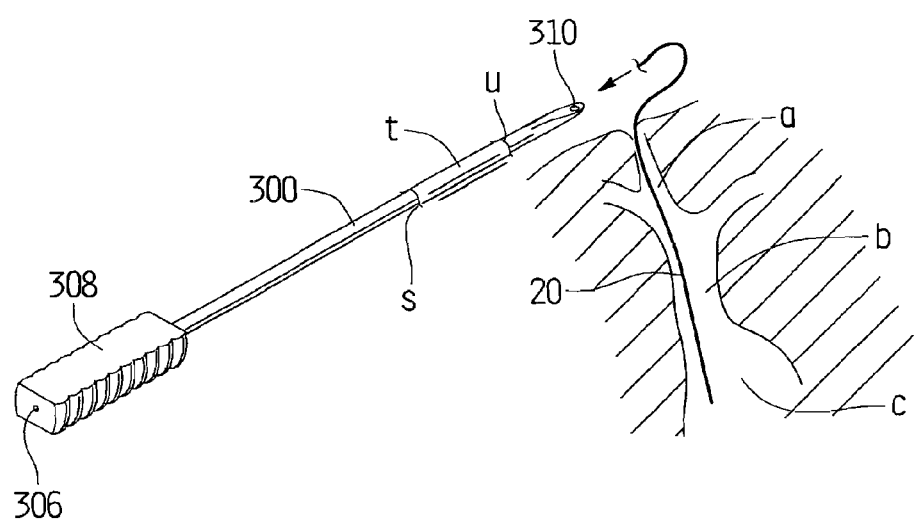
FIG_27

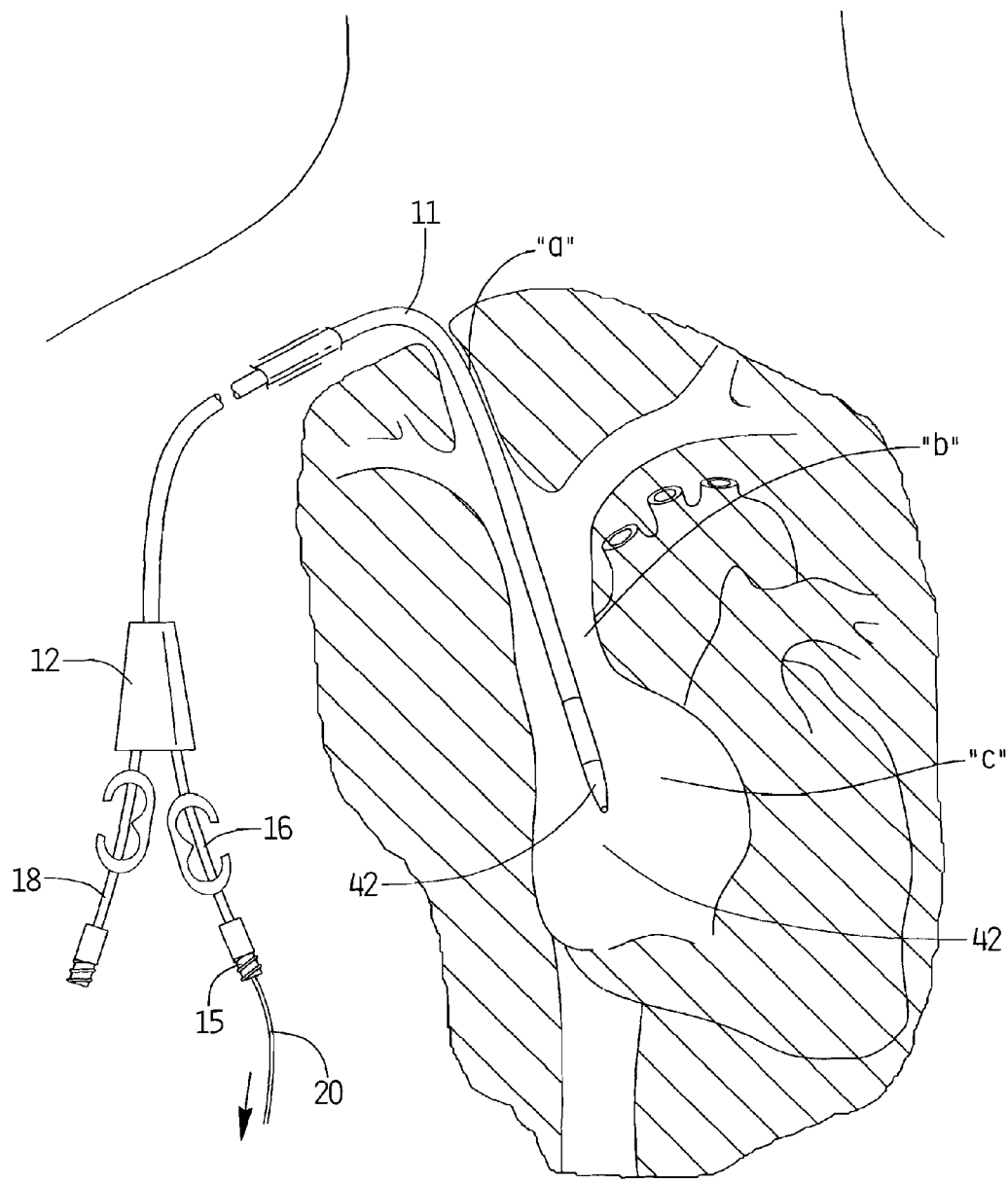
FIG_28C

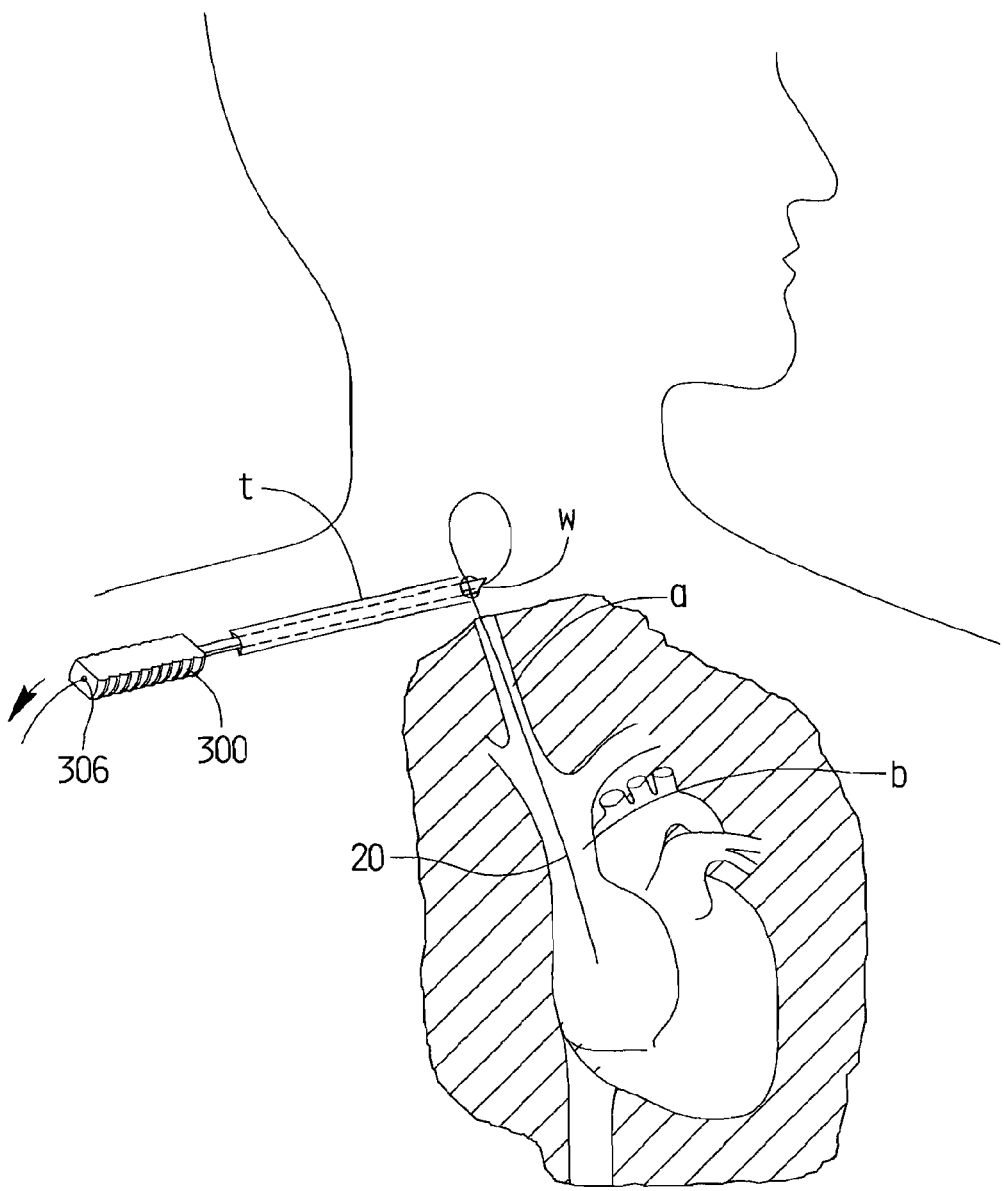
FIG_29A

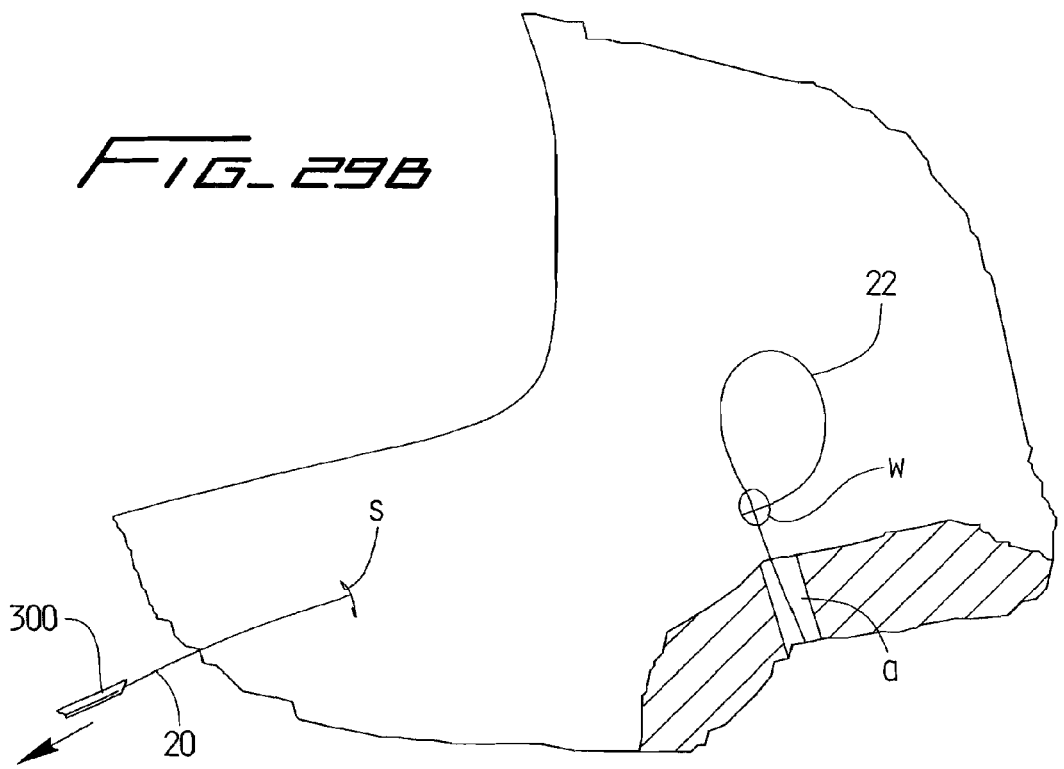
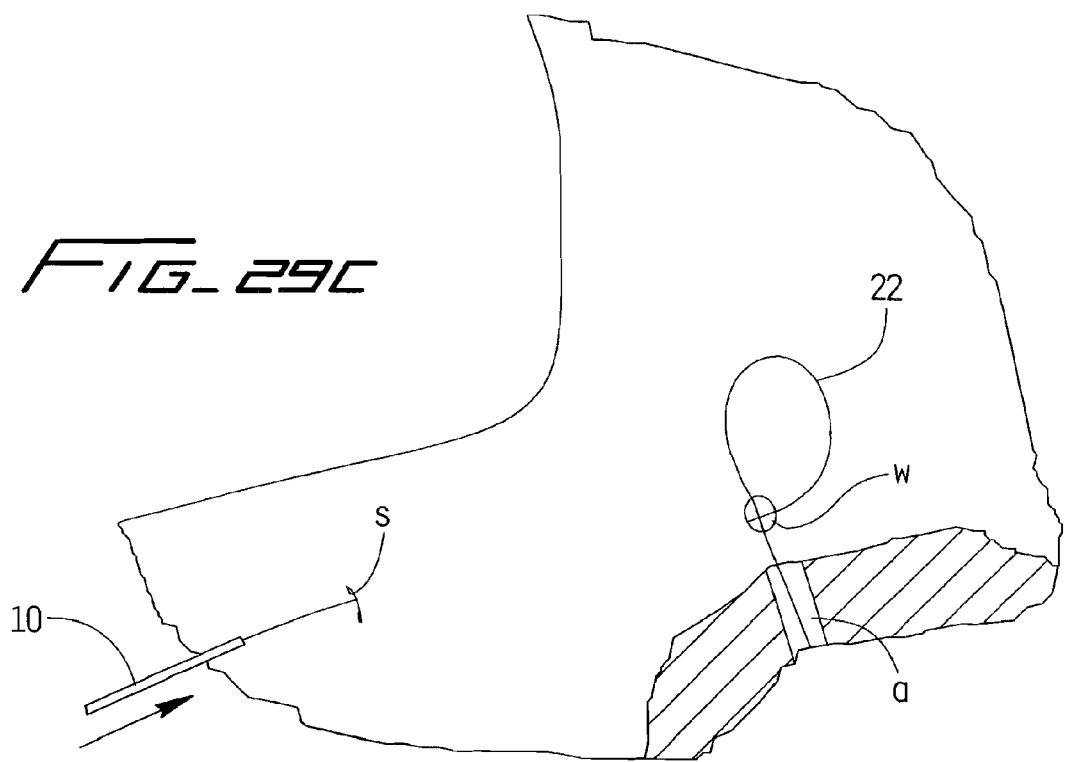

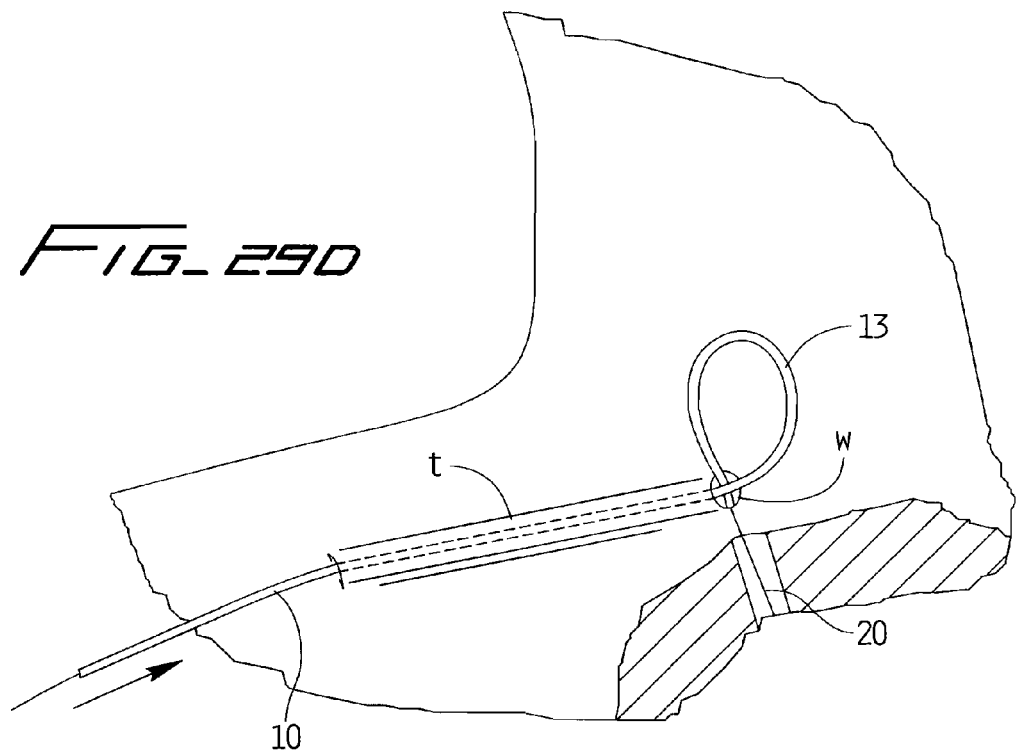
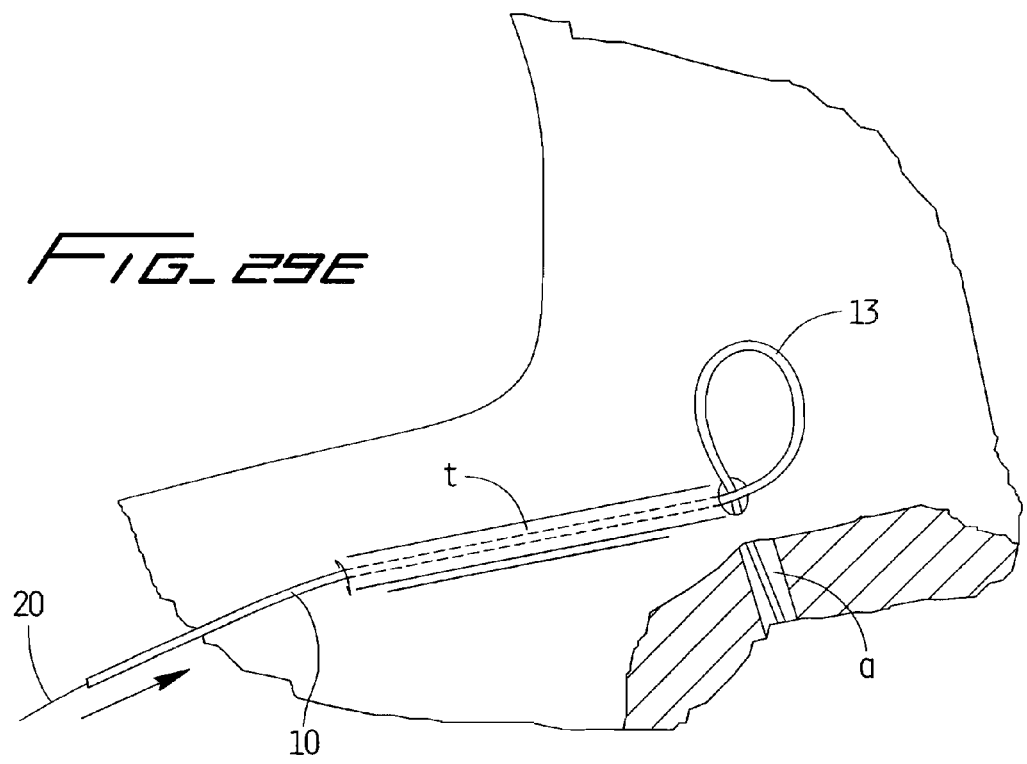

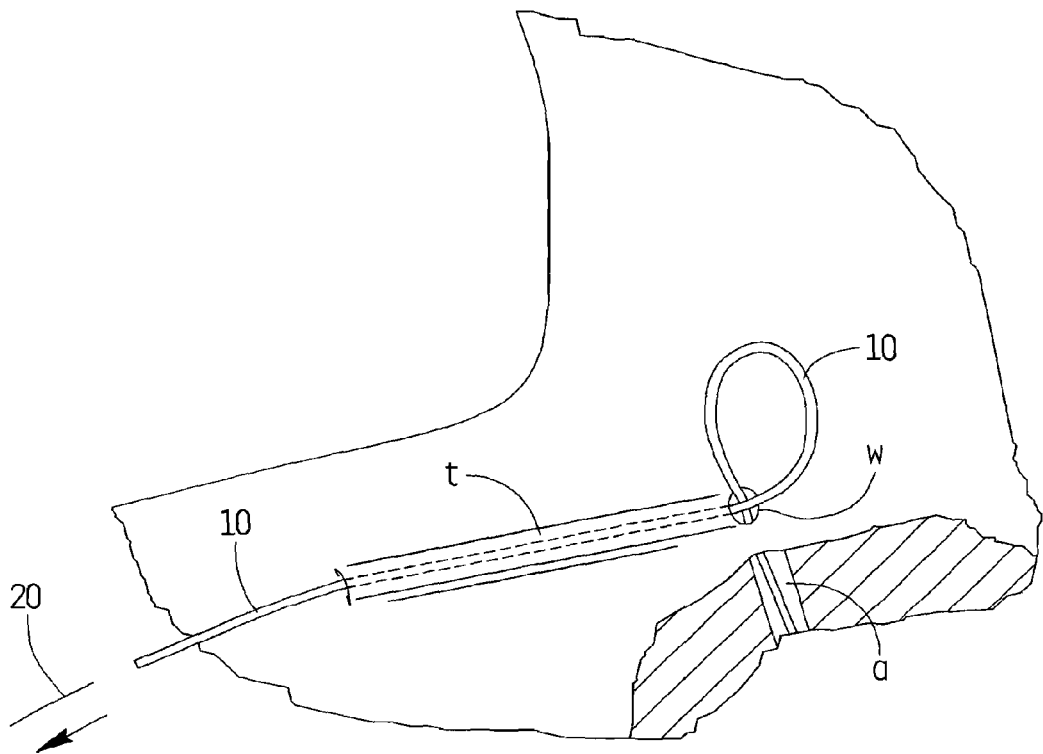

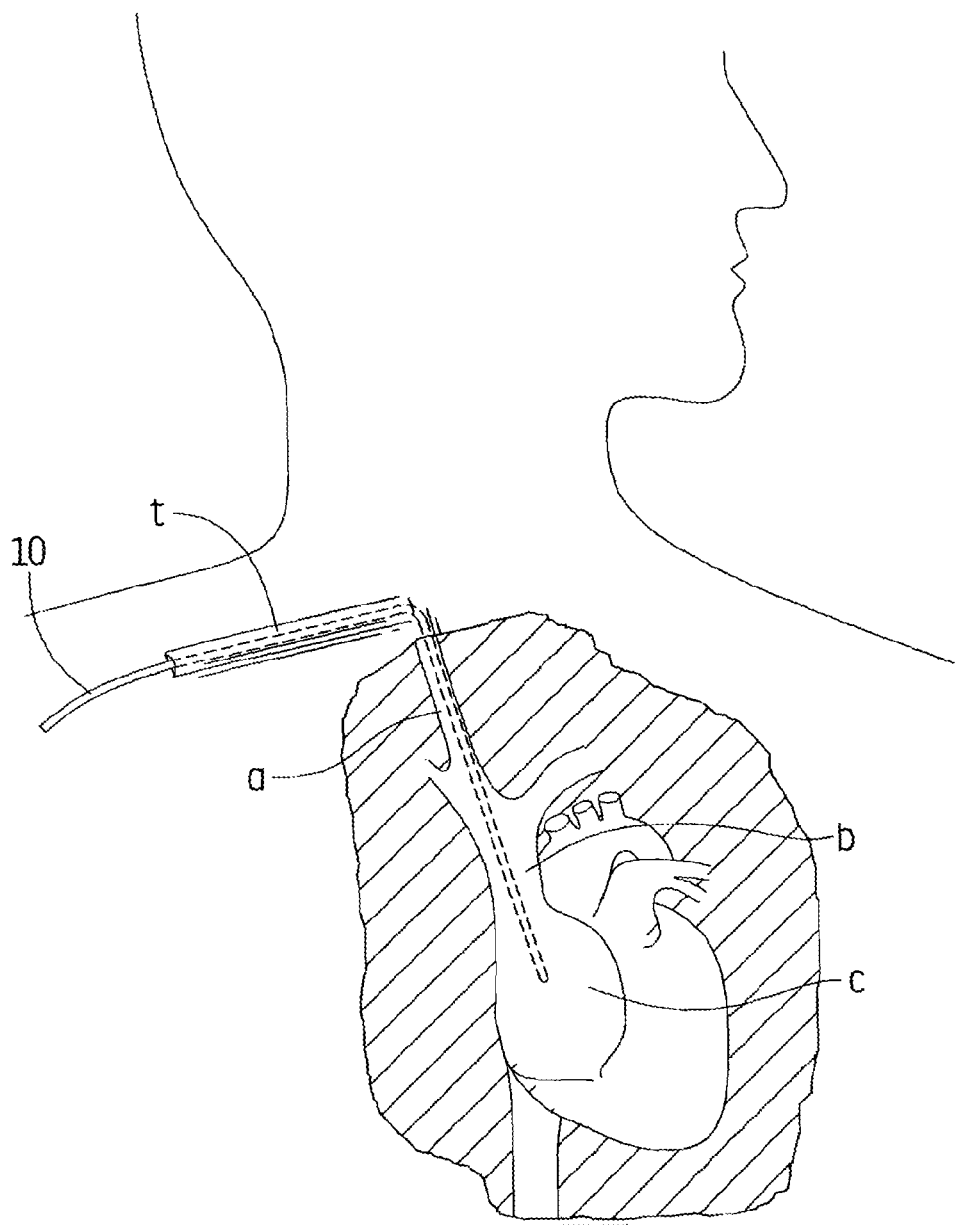

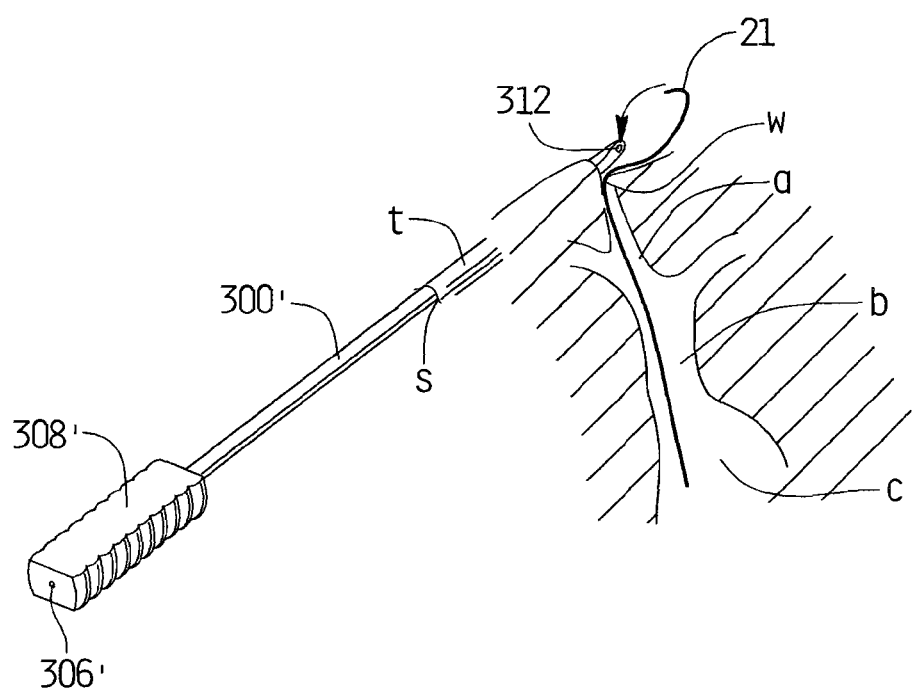
FIG_30

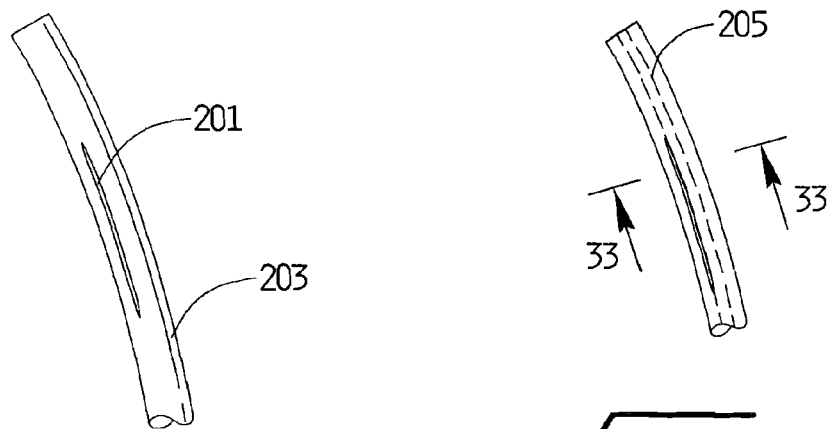
FIG_31
FIG_32
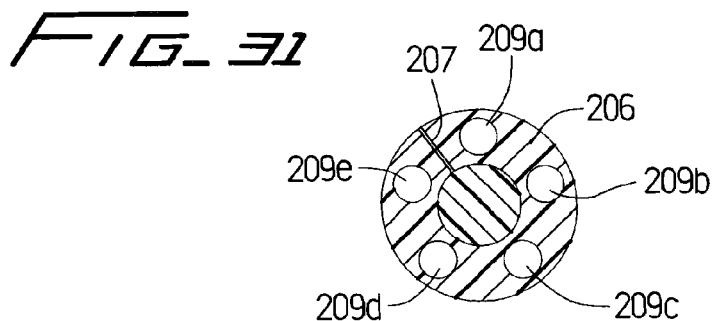
FIG_33
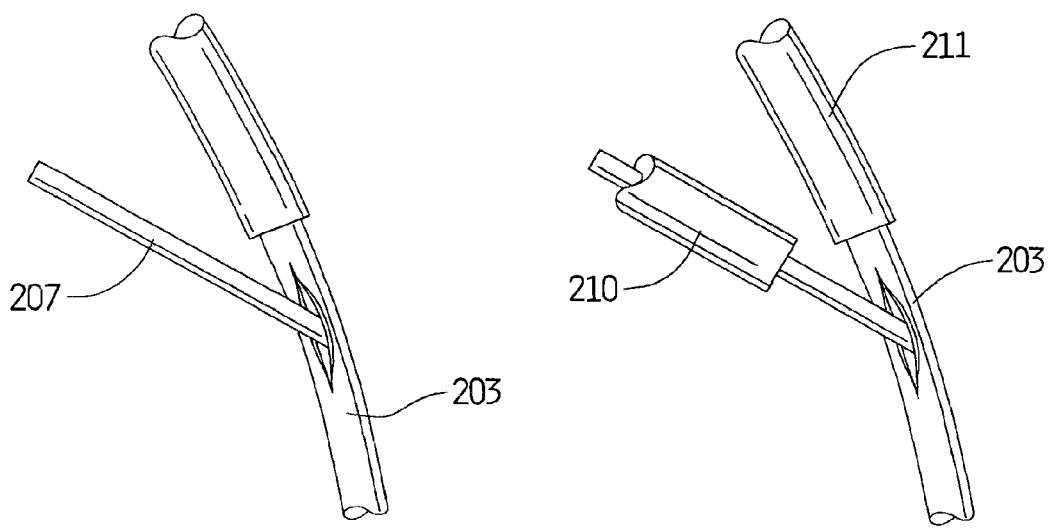
FIG_34
FIG_35

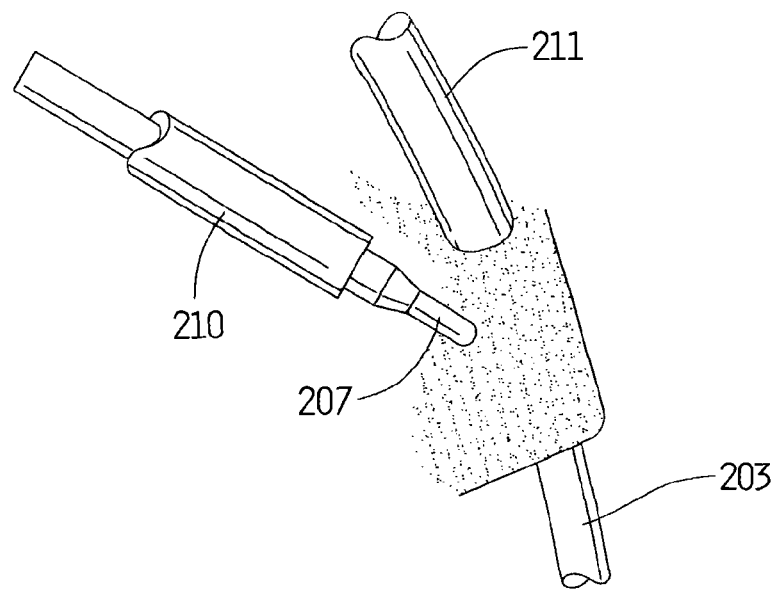
FIG_36
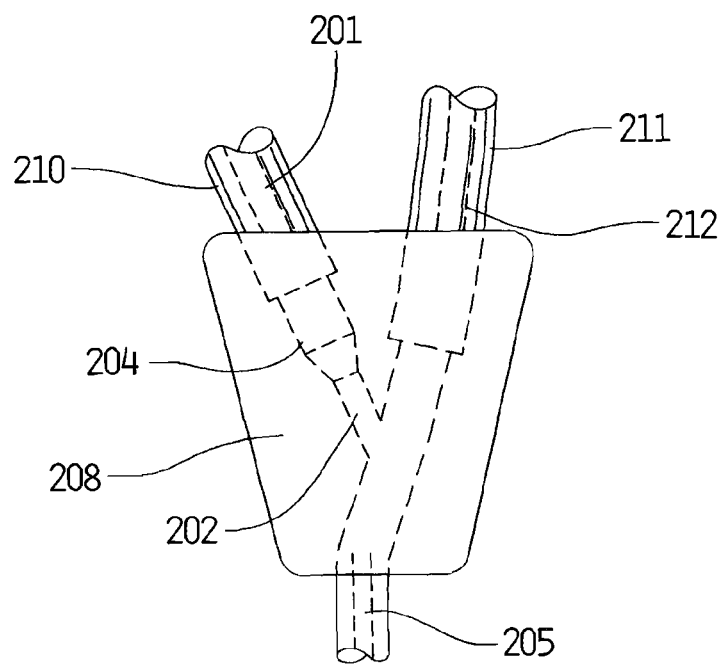
FIG_37

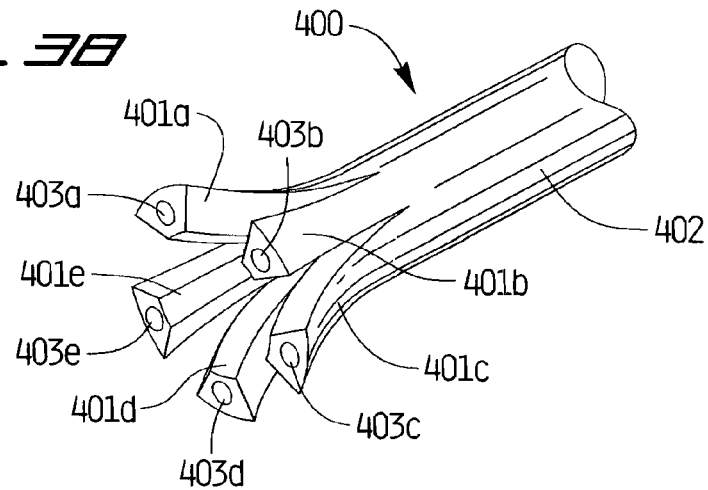
FIG_38
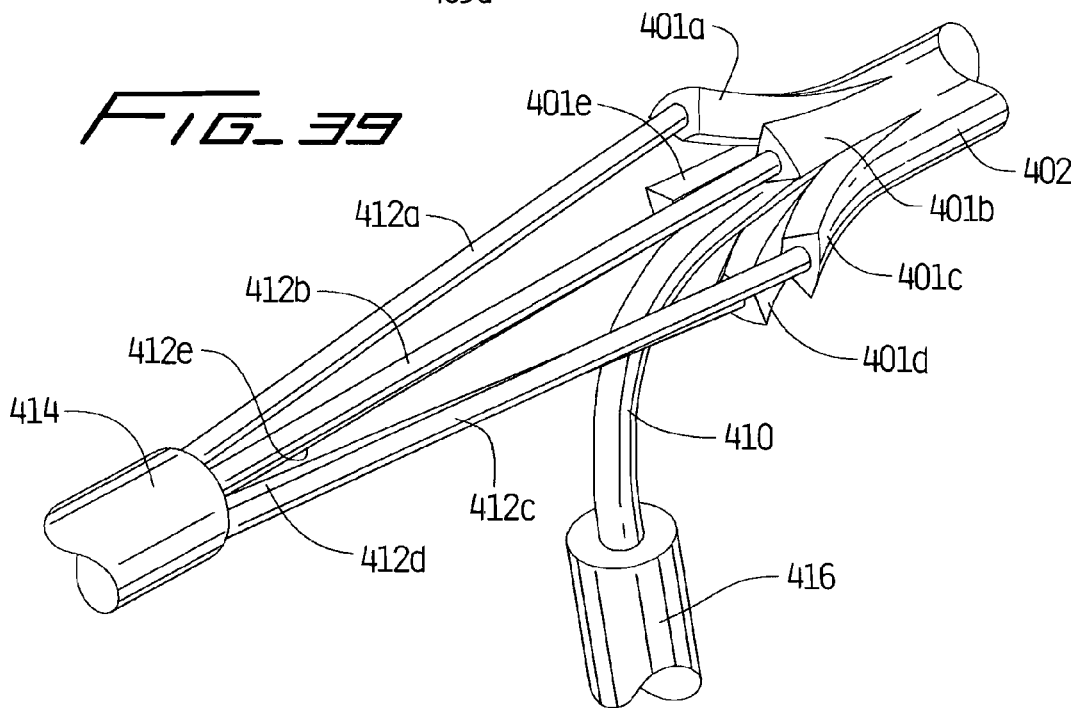
FIG_39
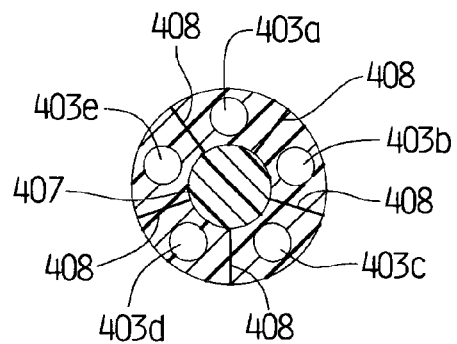
FIG_40

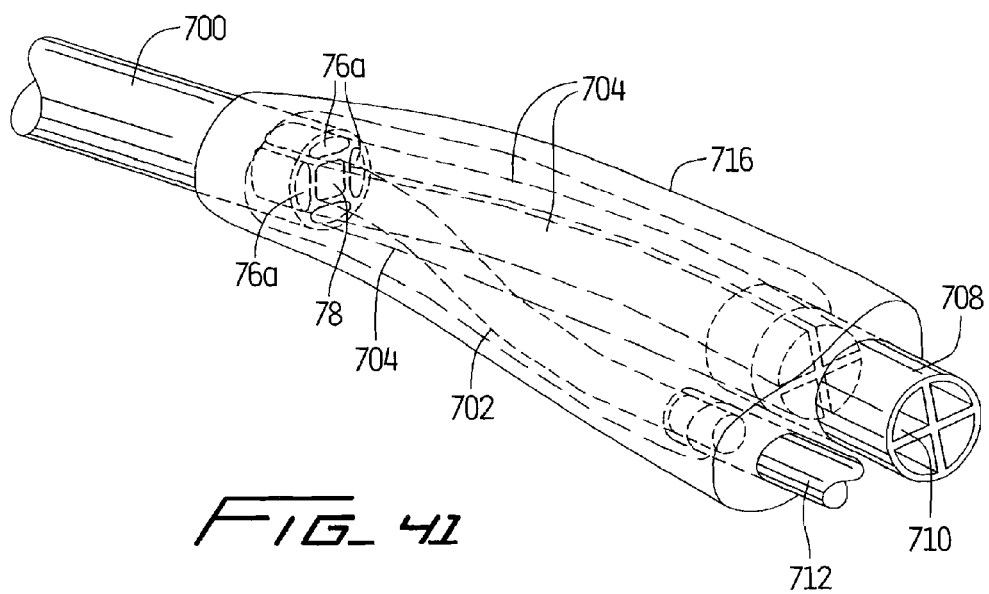
FIG_41
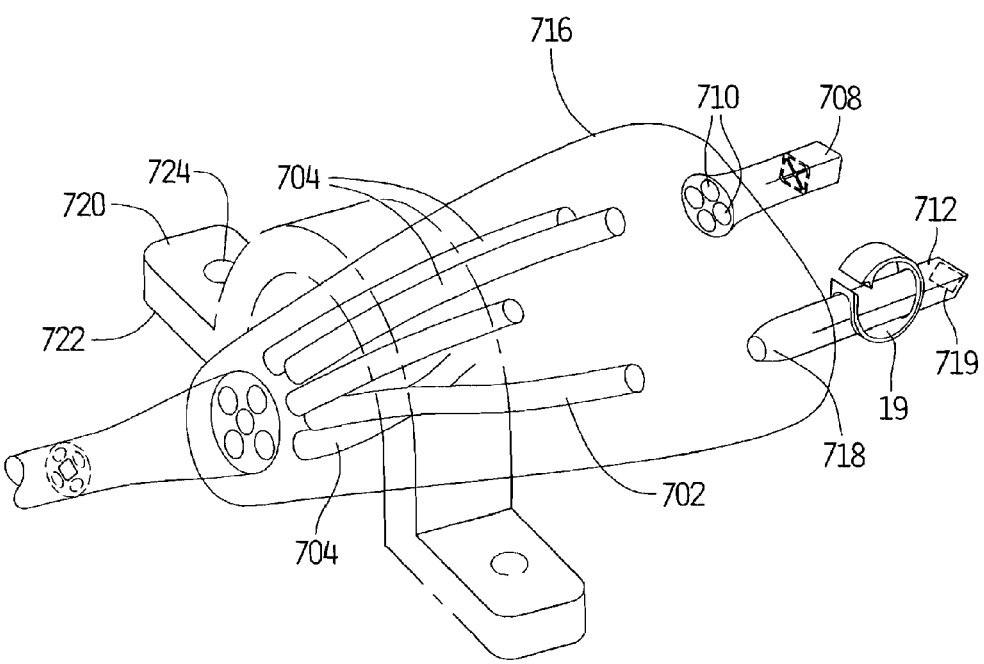
FIG_42

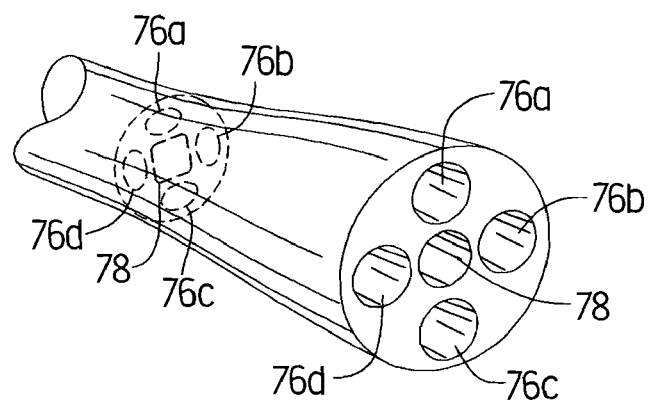
FIG_43
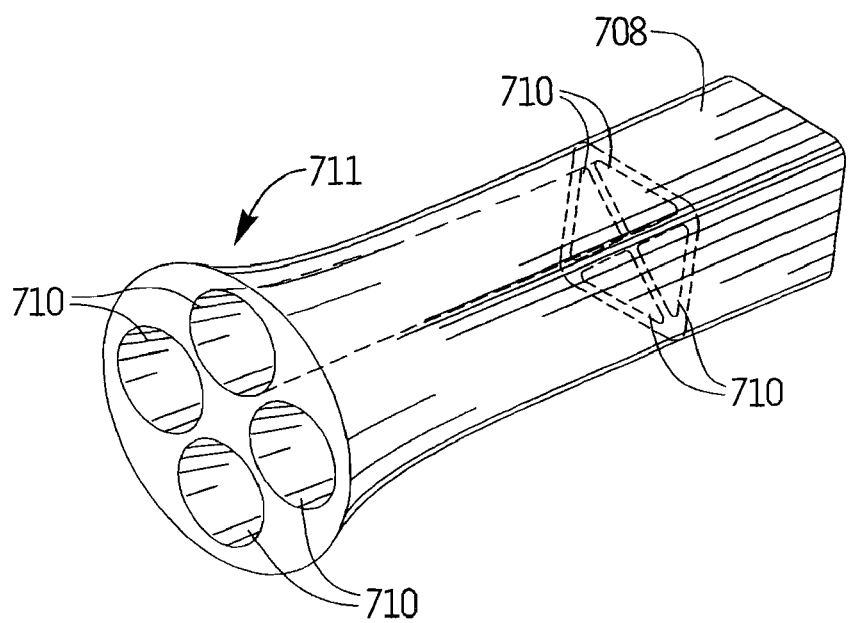
FIG_44

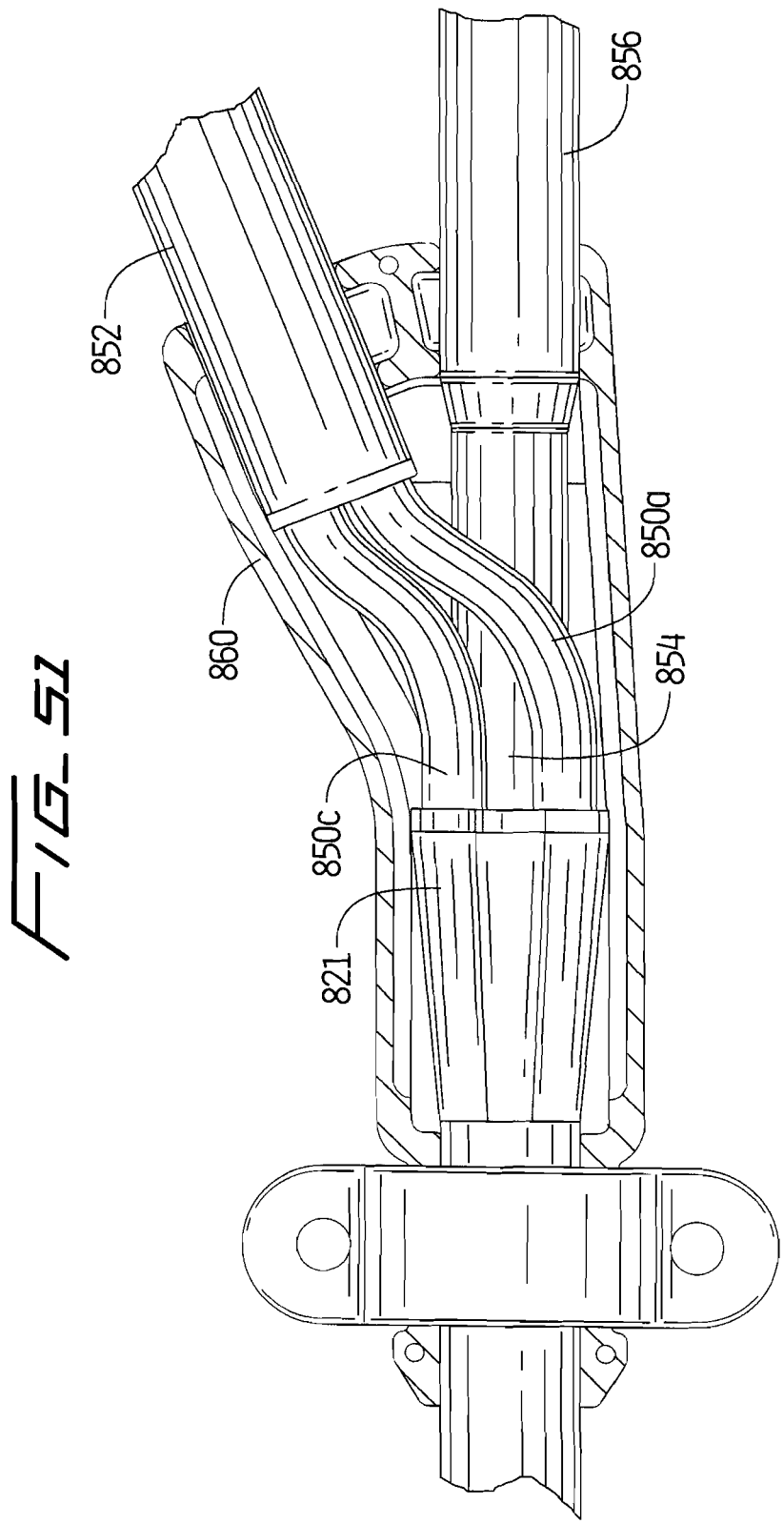

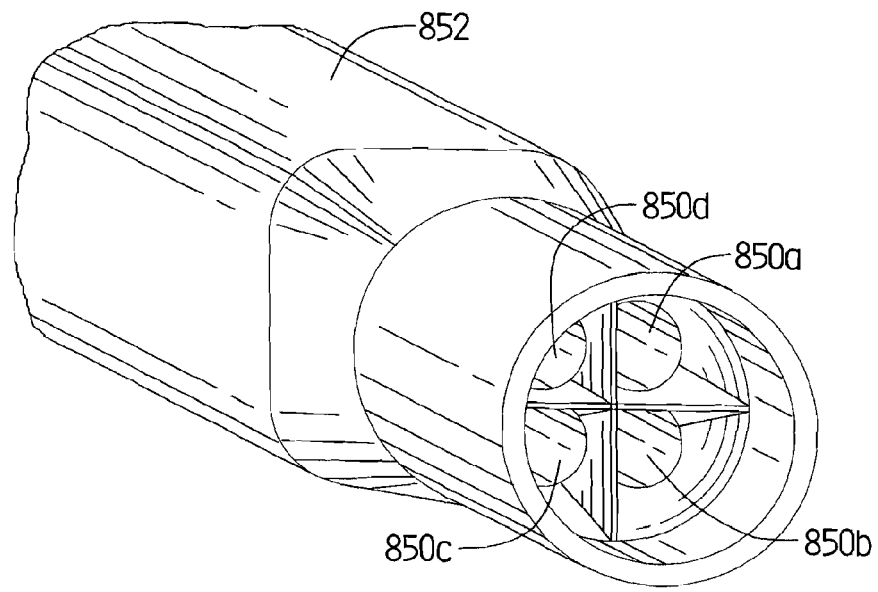
FIG_52
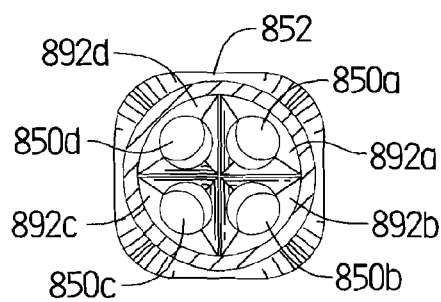
FIG_53
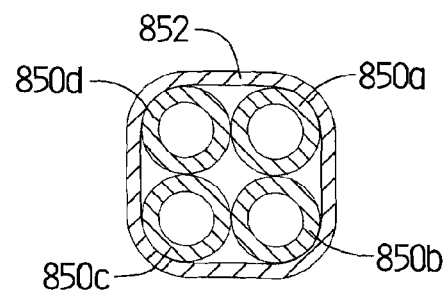
FIG_54

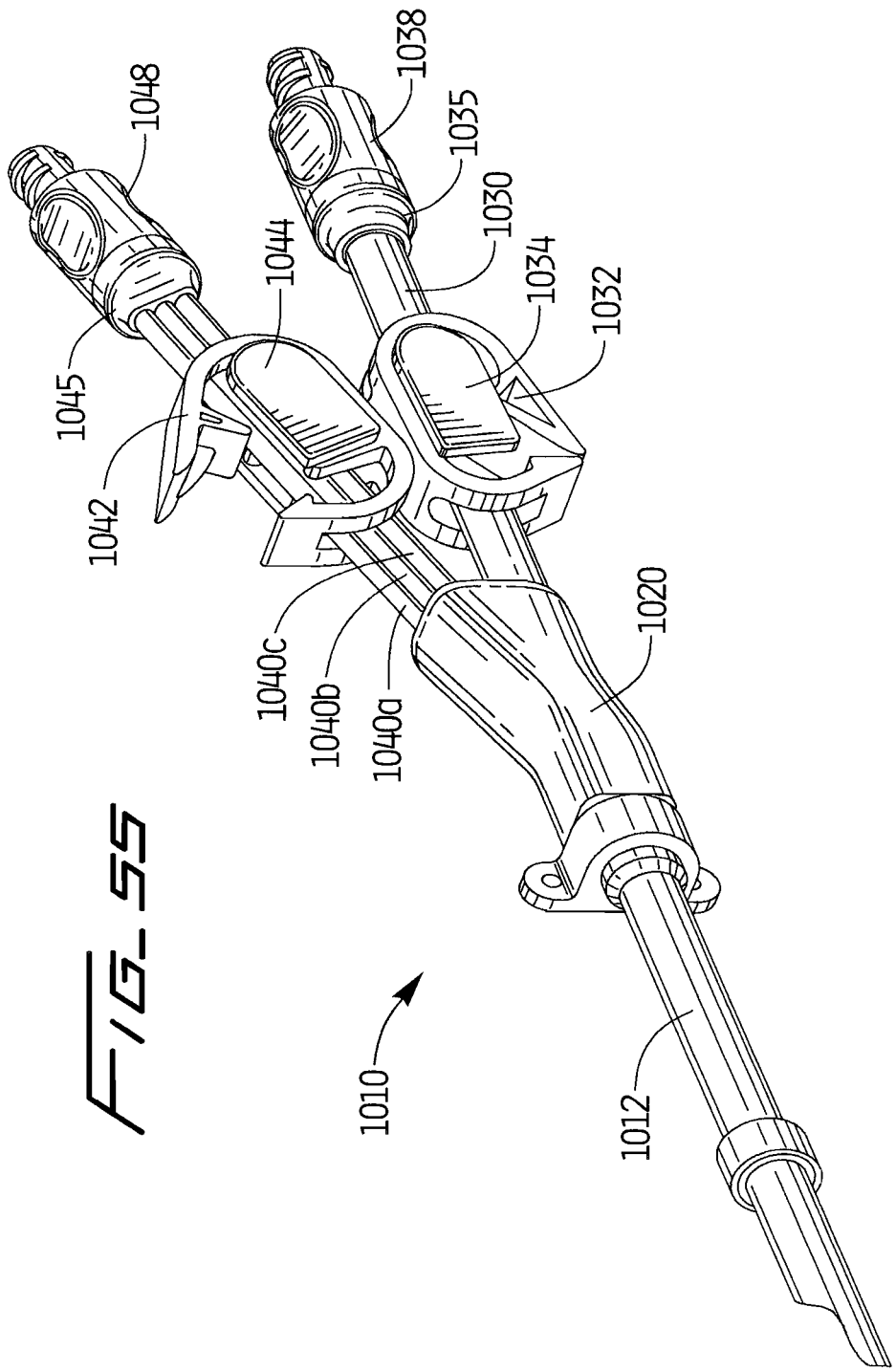

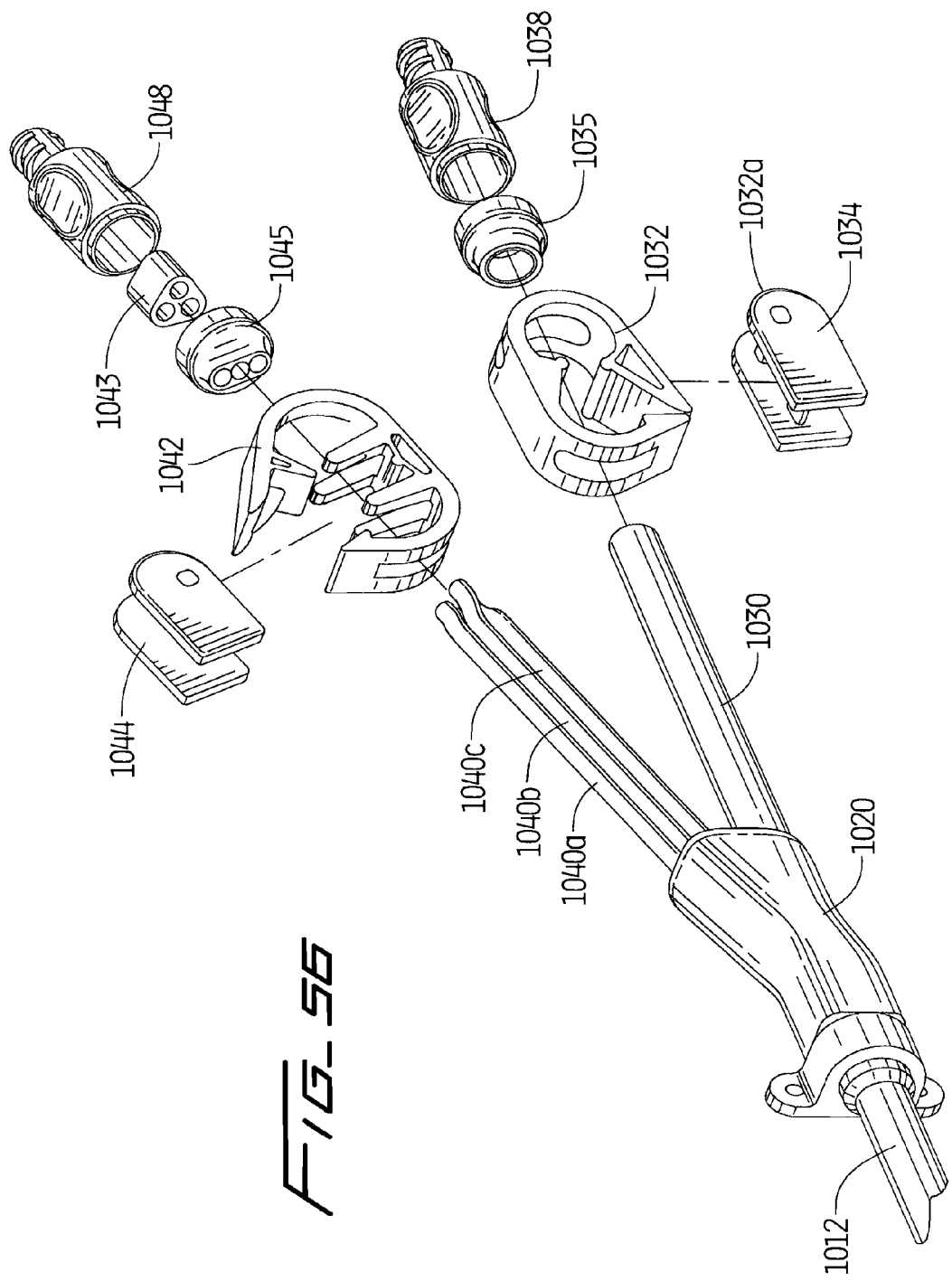

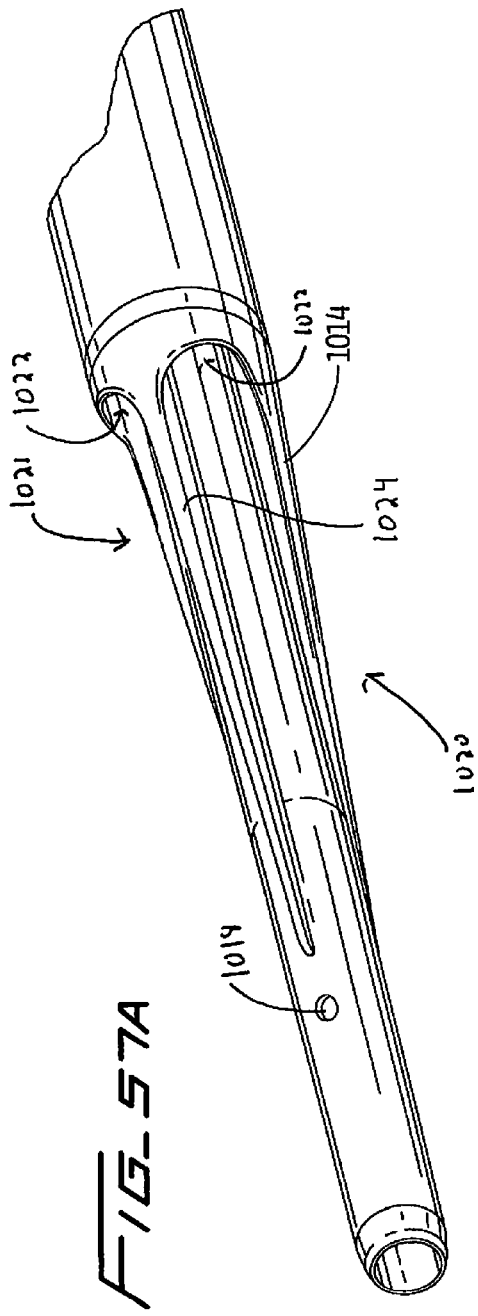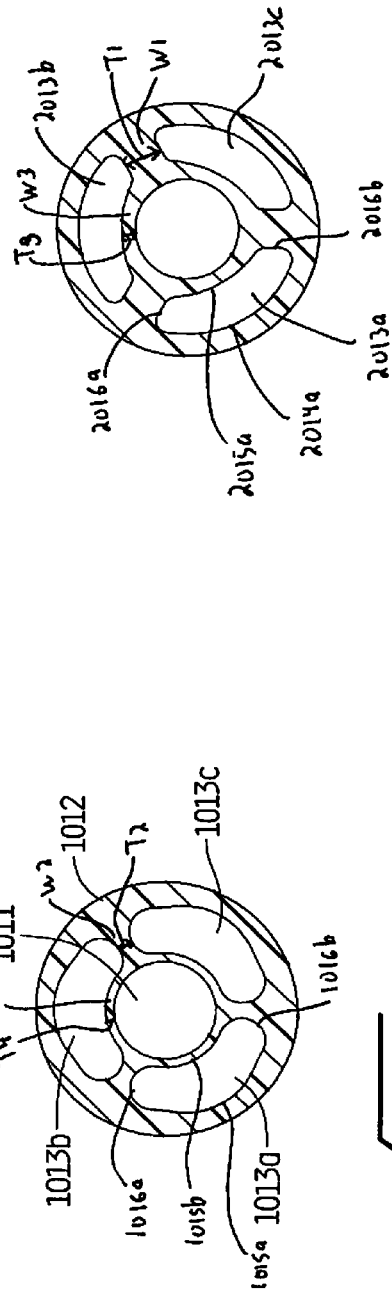

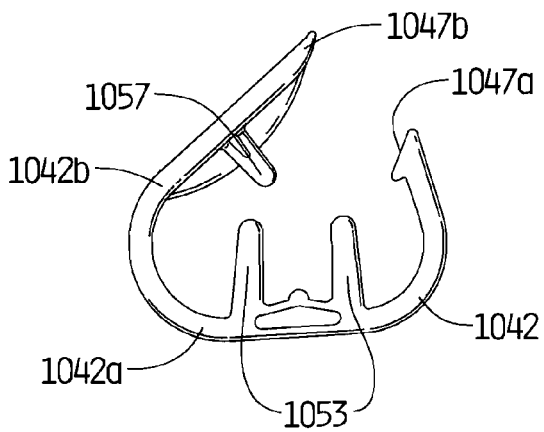
FIG_58A
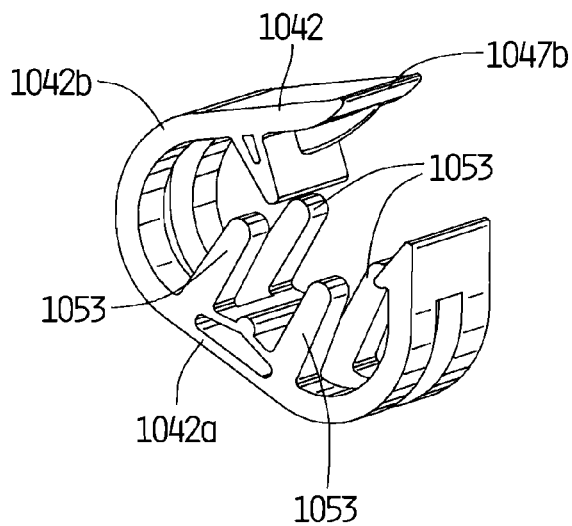
FIG_58B
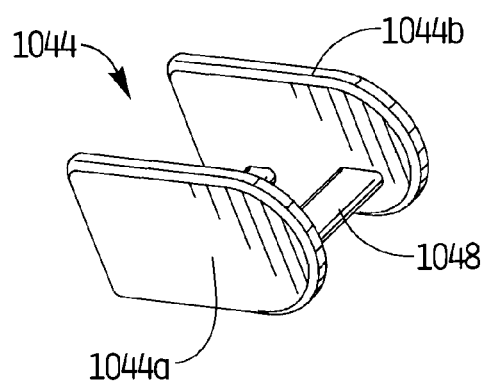
FIG_59A
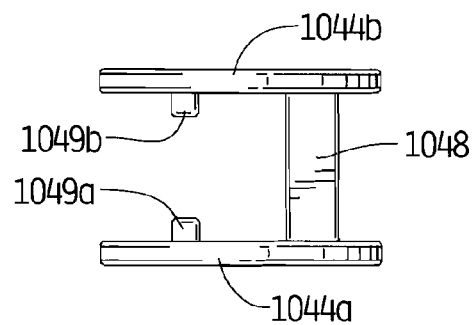
FIG_59B

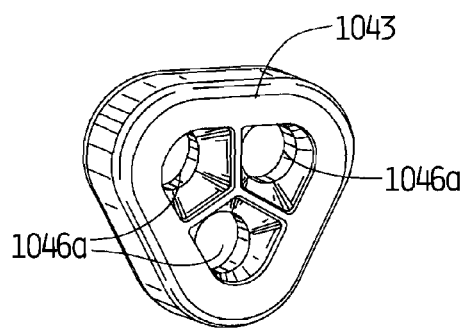
FIG_60
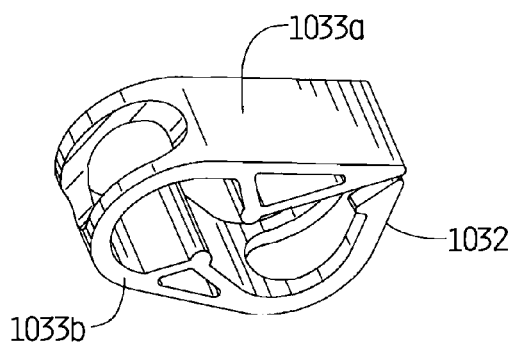
FIG_61A
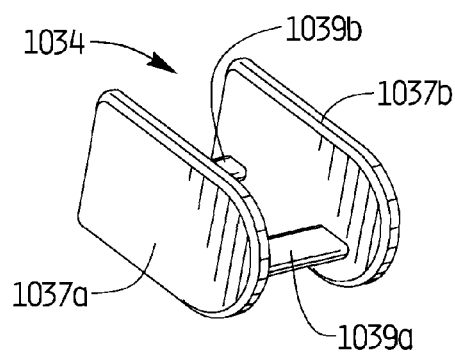
FIG_62A
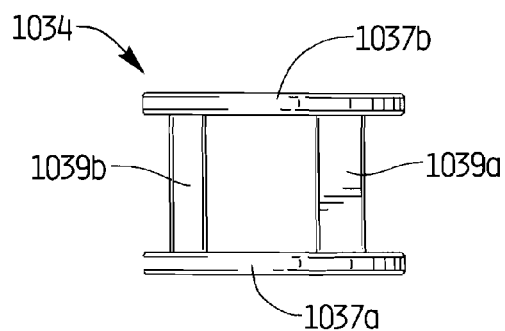
FIG_62B

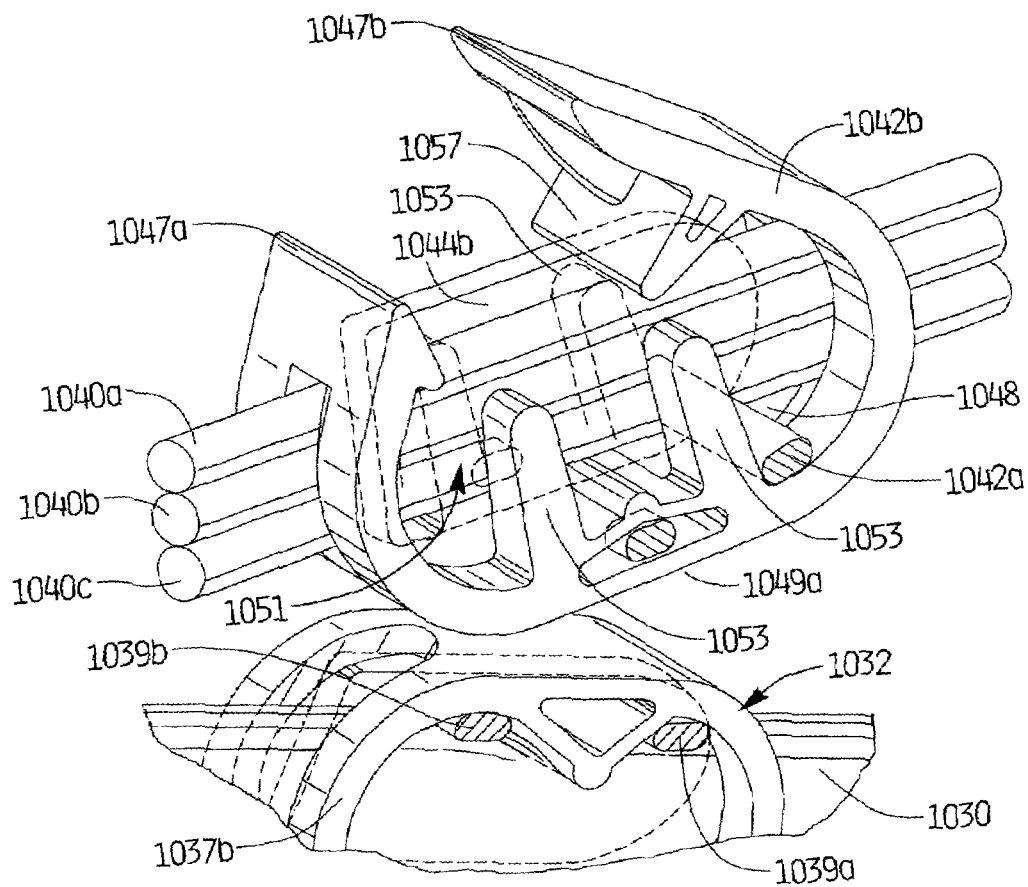
FIG_63

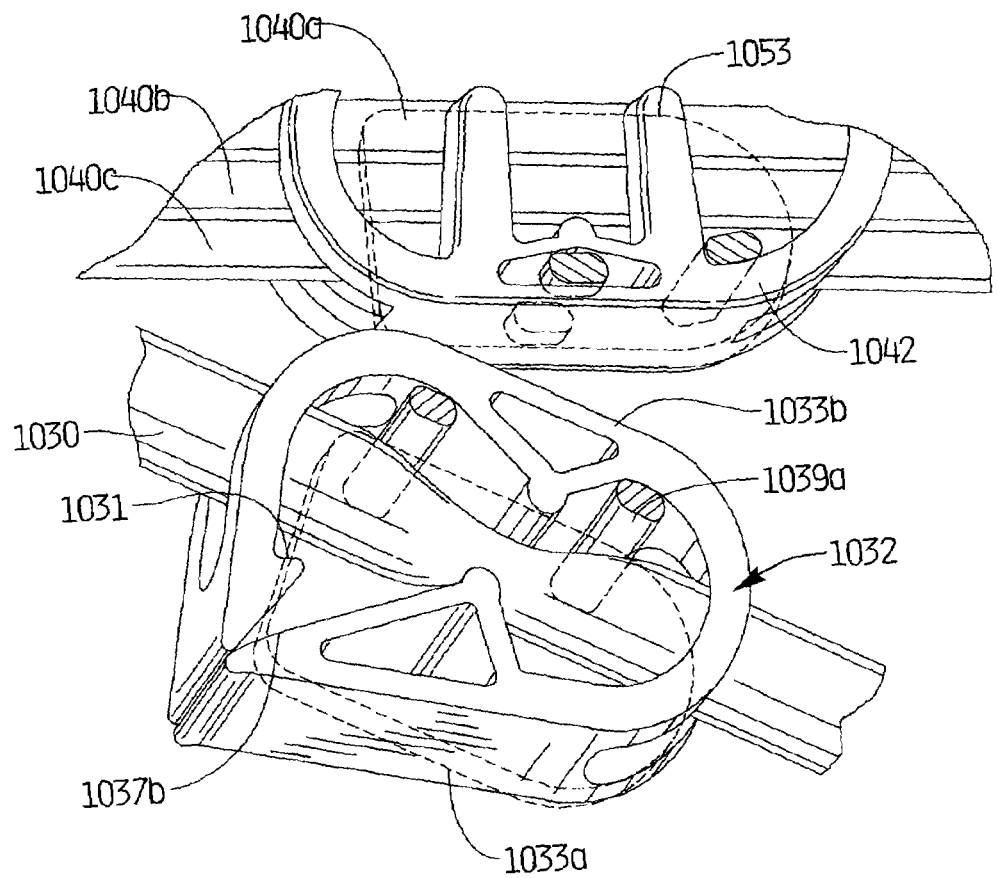
FIG_64

DIALYSIS CATHETER

This application is a continuation of U.S. patent application Ser. No. 12/079,716, filed Mar. 28, 2008 which claims priority from provisional application Ser. No. 60/923,101, filed Apr. 12, 2007 and is a continuation-in-part of U.S. patent application Ser. No. 11/487,750, filed Jul. 17, 2006 which is a continuation of application Ser. No. 10/279,468, filed Oct. 24, 2002, now U.S. Pat. No. 7,077,829, which is a continuation in part of application Ser. No. 10/025,506, filed Dec. 19, 2001, now U.S. Pat. No. 6,814,718, which claims priority from provisional patent application Ser. No. 60/260,592, filed Jan. 9, 2001. The entire contents of each of these applications are incorporated herein by reference.

BACKGROUND

1. Technical Field

This application relates to a catheter and more particularly to a multi-lumen catheter which facilitates hemodialysis.

2. Background of Related Art

Hemodialysis is a well known method of providing renal (kidney) function by circulating blood. The kidneys are organs which function to extract water and urea, mineral salts, toxins, and other waste products from the blood with filtering units called nephrons. From the nephrons the collected waste is sent to the bladder for excretion. For patients having one or both defective kidneys, the hemodialysis procedure is life saving because it provides a machine to simulate the function of the kidneys.

In the hemodialysis procedure, blood is withdrawn from the patient's body through a catheter or tube and transported to a dialysis machine, also commonly referred to as a kidney machine. The catheter is typically inserted through the jugular vein and maneuvered into position through the superior vena cava into the right atrium to provide high blood flow. In the dialysis machine, toxins and other waste products diffuse through a semi-permeable membrane into a dialysis fluid closely matching the chemical composition of the blood. The filtered blood, i.e. with the waste products removed, is then returned to the patient's body. In some instances, the catheter may be left in place for several years. As can be appreciated, proper access to the patient's blood and transport of the blood to and from the dialysis machine for this extended period of time is critical to hemodialysis.

One example of a dialysis catheter currently being marketed is the MedComp Ash Split catheter. This catheter has two lumens, one for arterial flow and the other for venous flow, which are each D-shaped in cross-sectional configuration. The catheter is bifurcated at its distal end to separate the lumens and the catheter is manually split to the desired length for selected separation before insertion into the target area. Another well-known catheter is a Med Comp catheter which has the venous flow lumen terminating proximally, i.e. axially recessed, from the arterial flow lumen. Each of these lumens is also D-shaped in cross-sectional configuration.

These Medcomp dialysis catheters require numerous steps for insertion. The multiple insertion steps can be summarized as follows:

1. an introducer needle is inserted through a first incision site (first opening) to properly locate (access) the vessel, e.g. the right internal jugular vein;
2. a guide wire is inserted through the needle into the internal jugular vein and down through the superior vena cava into the inferior vena cava;
3. the introducer needle is withdrawn leaving the guidewire in place;
4. a tear away (peel away) sheath and dilator are inserted over the guidewire and through the first incision site to provide an access port for the dialysis catheter into the jugular vein, superior vena cava and right atrium;
5. a second incision is made in the chest wall to create a second opening;
6. a trocar is attached to the distal end of the dialysis catheter;
7. the trocar and dialysis catheter are pushed through the second incision and advanced to bluntly dissect the subcutaneous tissue to exit the first incision (opening) which was created by the introducer needle, thereby creating a subcutaneous tissue tunnel between the first and second openings;
8. the trocar is detached from the dialysis catheter leaving the catheter in place extending from the second opening, through the tissue tunnel and out the first opening;
9. the dilator and guidewire are removed, leaving the tear away sheath in place in the first incision which has been expanded by the dilator;
10. the dialysis catheter, which is protruding from the first incision, is inserted through the tear away sheath and advanced so its distal portion is positioned in the right atrium;
11. the sheath is separated, i.e. split, by pulling the tabs apart, and then pulled upwardly away from the dialysis catheter and removed from the body, leaving the catheter in place; and
12. the second incision is closed and the dialysis catheter, which is connected through tubes to the dialysis machine, is left in place an extended period of time to provide blood circulation to and from the dialysis machine.

(Alternatively, in the foregoing method, the trocar can be forced through a third incision exiting adjacent the first incision, and then the catheter inserted through second and third incisions and through the introducer sheath positioned in the first incision.)

This multiple step process of inserting the Medcomp dialysis catheter is time consuming and complicates the surgical procedure. These multiple steps add to the cost of the procedure, not only because of the additional surgeon's time but because additional components, such as the tear-away sheath, are required which increases the overall cost of the catheter system. Also, removal of the dilator increases the tendency of the sheath to kink causing difficulties in catheter insertion.

The use of the tear away sheath is also potentially problematic. The tear-away sheath has lines of weakness to separate it as it is pulled apart by the pull tabs to enable removal of the sheath. However, the sheath can potentially cause damage to the vessel wall as it is being pulled apart and can cause infection. Moreover, pulling the sheath laterally can enlarge the incision, thereby increasing the difficulty of closing the incision at the end of the procedure. Also, since the sheath is pulled in the proximal direction for removal, it could pull the catheter proximally as well, thereby pulling it away from the desired site, and requiring repositioning. The edges of the tear away can also lacerate the surgeon's glove and finger. Over dilation by the sheath can cause blood leakage.

An additional potential risk with utilizing tear away sheaths is that air embolism can occur. During the time the surgeon withdraws the dilator from the sheath and inserts the catheter, a passageway through the sheath to the vessel is open. If the patient inhales during this catheter exchange, an air bubble can enter the vascular system and obstruct the vessel, potentially causing stroke or even death.

It would therefore be advantageous if a dialysis catheter insertion method could be provided which reduces some of the foregoing procedural steps, thereby decreasing the complexity of the procedure and decreasing the hospital and surgeon costs. It would also be advantageous if such dialysis catheter insertion method could be provided which would be less traumatic and avoid the foregoing problems associated with the use of a tear-away sheath, such as increased risk of air embolism, trauma to the vessel wall, incision enlargement and dislodgement of the catheter.

Another area of dialysis catheter insertion, which needs improvement, is guiding the catheter to the target site. Dialysis catheters are composed of flexible tubing to minimize damage to the vessel wall during insertion and use. This flexibility, however, oftentimes results in kinking of the catheter since the catheter must navigate curves to reach the target vessel. This kinking can adversely affect blood flow. Also, the catheter needs to have some degree of stiffness to enable directing the catheter around the curves of the vessels. The stiffness, however provides its own risks since if the catheter is not properly directed, the catheter can inadvertently be forced against the vessel wall, thereby puncturing or damaging the vessel. Several different approaches have been discussed in the prior art to increase stiffness of catheters such as providing a distal tip of stiffer material to guide the catheter as in U.S. Pat. No. 5,957,893, using materials of different durometers in various portions of the catheter (U.S. Pat. No. 5,348,536), placing an additional concentration of material in the tip as in U.S. Pat. No. 4,583,968, or providing reinforcing strips, obturators or tubes within the catheter body to increase the rigidity (e.g. U.S. Pat. Nos. 4,619,643, 4,950,259 5,221, 255, 5,221,256, and 5,246,430). The need however exists to improve the balance between flexibility and stiffness. Thus it would be advantageous to provide a catheter with sufficient flexibility to accommodate anatomical curves of the patient while still having sufficient stiffness to enable guiding the flexible catheter tubing atraumatically through the length of the vessels.

In navigating vessels to access the target site, such as the right atrium, it is desirable to provide the smallest catheter profile, i.e. the smallest outer diameter catheter body. This profile facilitates insertion through smaller vessels as it reduces the likelihood of the catheter engaging the wall of the vessel and reduces trauma to the vessel by minimizing frictional contact with the vessel wall. However, the desire for smaller diameter catheters must be balanced against the need for providing sufficient sized lumens to enable proper blood flow. If the lumens are too small, sufficient blood flow may not be able to be maintained and the blood can be damaged during transport. Also, a sufficient relationship must be maintained between the size of the lumens and the overall diameter of the catheter to maintain the structural integrity of the catheter.

Numerous attempts have been made in the prior art to optimize the multi-lumen configuration. In some approaches, such as disclosed in U.S. Pat. Nos. 4,568,329 and 5,053,023, inflow and outflow lumen are provided side by side in D-shaped form. In other approaches, such as those disclosed in U.S. Pat. Nos. 4,493,696, 5,167,623 and 5,380,276 the inflow and outflow tubes are placed in concentric relation. Other examples of different lumen configurations are disclosed in U.S. Pat. Nos. 5,221,256, 5,364,344, and 5,451,206. The lumen configuration must accommodate two competing factors: keeping the catheter as small as possible to facilitate insertion while keeping the lumens as large as possible for blood flow. This balance must be achieved while maintaining the structural integrity of the catheter. It would therefore be advantageous to provide a catheter which reaches an optimum compromise between these two competing factors.

Another important feature of dialysis catheters is the suction openings to withdraw blood. Keeping the suction openings clear of thrombolytic material and away from the vessel wall is clearly essential to dialysis function since an adequate supply of blood must be removed from the patient to be dialyzed. However, a problem with prior dialysis catheters is that during blood withdrawal, as suction is being applied through the catheter openings and lumen, the suction can cause the catheter to be forced against the side wall of the vessel, known as "side port occlusion", which can block the opening and adversely affect the function of the catheter by enabling only intermittent suction. In fact, the opening can become completely blocked, thereby preventing necessary intake of blood, i.e. venous flow. Fibrin sheath growth around the outside of the catheter can occur since dialysis catheters are oftentimes implanted for several months or even years. This fibrin growth, caused by the body's attempt to reject the catheter as a foreign body, could result in blocking of the suction holes.

The need therefore exists for an improved dialysis catheter which facilitates the surgical dialysis procedure. Such catheter would advantageously reduce the catheter insertion time, simplify the catheter insertion process, eliminate the need for a peel-away introducer sheath, decrease the chances of infection, reduce unwanted kinking of the catheter during insertion, strike an optimal balance between overall catheter and lumen size, and improve the suction capability to avoid hampering of blood flow.

Co-pending, commonly assigned prior patent application Ser. No. 11/487,750, filed Jul. 17, 2006, incorporated herein in by reference in its entirety, overcomes the disadvantages and deficiencies of the prior art. The dialysis catheter disclosed herein is a modification to the catheter of the '750 patent and provides similar advantages over the prior art.

SUMMARY

The present invention provides a dialysis catheter comprising a first portion having a first diameter, an elongated distal portion having a second diameter smaller than the first diameter, and a transition region between the first portion and distal portion. A first longitudinally extending central lumen configured to deliver blood terminates in an opening in the distal portion. At least two independent longitudinally extending lumens are positioned radially of the first lumen, configured to withdraw blood from a patient, and terminate in a longitudinally directed opening in the transition region.

Preferably the transition region tapers toward the distal portion and preferably at least a portion of the wall thickness of the catheter in the distal portion tapers toward a distalmost end with the central lumen cross-sectional area remaining substantially constant throughout its length in the distal portion.

The catheter may further comprise a stiffening member removably positionable within the catheter to temporarily increase the stiffness of the catheter to facilitate insertion.

The present invention also provides a medical catheter comprising a first return lumen, a plurality of withdrawal lumens, a first clamping member and a plurality of intake extension tubes. Each intake extension tube communicates with an intake lumen of the catheter to provide fluid communication with the respective intake lumens. The intake extension tubes are positioned in a stacked arrangement, and the clamping member has a plurality of posts to receive the stacked tubes to limit lateral movement thereof.

The catheter preferably further comprises an independent venous extension tube communicating with the return lumen of the catheter.

In one embodiment, the catheter includes a first tag connected to the first clamping member and a second tag connected to the second clamping member to provide information to the user. In one embodiment, the first tag includes first and second side walls and a bridge extending between the first and second side walls and the second tag includes first and second sidewalls and a bridge extending between the first and second sidewalls.

The present invention also provides in combination a clamping member and a plurality of extension tubes of a medical catheter for delivering and withdrawing blood from a patient's body. The plurality of intake extension tubes each communicate with an intake lumen of the catheter to provide fluid communication with the respective intake lumens. The intake extension tubes are positioned in a stacked arrangement. The clamping member has a plurality of posts to receive the stacked tubes to limit lateral movement thereof.

In one embodiment, the combination further includes a luer and an adapter interposed between the plurality of intake extension tubes and the luer. In a preferred embodiment, the adapter has three openings arranged in a triangular arrangement to receive and reorient the extension tubes.

In a preferred embodiment a first tag is connected to the clamping member to provide information to the user. The tag in one embodiment comprises a first and second side wall and a bridge extending between the first and second side walls.

The first clamping member in one embodiment has a pair of proximal posts and a pair of distal posts spaced axially from the proximal posts.

The combination may also include an independent venous extension tube communicating with a return lumen of the catheter, a second clamping member for clamping the venous extension tube and a second tag connected to the second clamping member. The second tag in one embodiment includes first and second sidewalls and a bridge extending between the first and second sidewalls.

BRIEF DESCRIPTION OF THE DRAWINGS

Preferred embodiment(s) of the present disclosure are described herein with reference to the drawings wherein:

FIG. 2 is a plan view illustrating the multi-lumen catheter of FIG. 1 being inserted through the left internal jugular vein and superior vena cava into the right atrium;

FIG. 3 is an isometric view of the first embodiment of the multi-lumen catheter of the present invention and showing the direction of insertion of the stiffening rod;

FIG. 4A is a side view of a first embodiment of a stiffening rod of the present invention insertable through the catheter of FIG. 3 to facilitate catheter insertion;

FIG. 4B is a side view of an alternate embodiment of the stiffening rod of the present invention having a series of mounting threads at its distal end;

FIG. 5 is perspective view of the distal portion of the multi-lumen catheter of FIG. 3 and showing a guidewire extending through the central lumen;

FIG. 6A is a longitudinal cross-sectional view taken along lines 6A-6A of FIG. 5;

FIG. 6B is a longitudinal cross-sectional view similar to FIG. 6A except showing an alternate embodiment of the catheter having internal threads for securing the stiffening rod of FIG. 4B;

FIG. 7 is a transverse cross sectional view taken along lines 7-7 of FIG. 6A;

FIG. 8 is a transverse cross sectional view taken along lines 8-8 of FIG. 6A:

FIG. 9A is a transverse cross-sectional view similar to FIG. 8 except showing a second alternate embodiment of the lumen configuration of the catheter of the present invention;

FIG. 9B is a transverse cross-sectional view similar to FIG. 8 except showing a third embodiment of the lumen configuration of the catheter of the present invention;

FIG. 9C is a transverse cross-sectional view similar to FIG. 8 except showing a fourth embodiment of the lumen configuration of the catheter of the present invention;

FIG. 10 is a transverse cross-sectional view similar to FIG. 8 except showing a fifth embodiment of the lumen configuration of the catheter of the present invention;

FIG. 11 is a longitudinal cross sectional view of the distal end portion of the catheter of FIG. 3 illustrating the stiffening rod of FIG. 4A being inserted through the central lumen of the catheter;

FIG. 12 is a longitudinal cross sectional view similar to FIG. 11 except showing the stiffening rod fully positioned within the central lumen, in abutment with the stop in the distal tip;

FIGS. 13-15 illustrate an alternate embodiment of the distal tip of the catheter of the present invention and the method steps for forming the tip wherein:

FIGS. 13A and 13B are perspective and cross-sectional views, respectively, of the tip before formation shown receiving a stiffening insert;

FIGS. 14A and 14B are perspective and cross-sectional views, respectively, of the tip once the stiffening inserted has been placed therein;

FIGS. 15A and 15B are perspective and cross-sectional views, respectively, of the distal tip formed into a bullet nose configuration and showing side holes formed therein;

FIG. 16A is a perspective view of a distal portion of another alternate embodiment of the multi-lumen catheter of the present invention having a series of spacer wires and showing a guidewire extending therethrough;

FIG. 16B is a longitudinal cross-sectional view of the distal portion catheter of FIG. 16A showing the spacer wires in the extended position;

FIG. 16C is a longitudinal cross-sectional view similar to FIG. 16A except showing the profile of the spacing wires and catheter body reduced as the stiffening rod of FIG. 4A is inserted into the central lumen over the guidewire to stretch the catheter during insertion;

FIG. 17A is a perspective view of a distal portion of yet another alternate embodiment of the catheter having a series of integral spacer ribs;

FIG. 17B is a longitudinal cross-sectional view of the distal portion of catheter of FIG. 17 showing the spacer ribs in the extended position;

FIG. 17C is a longitudinal cross-sectional view similar to FIG. 17A except showing the profile of the spacer ribs and catheter body reduced as the stiffening rod of FIG. 4A is inserted into the central lumen to stretch the catheter during insertion;

FIG. 18 is a perspective view of a distal portion of another alternate embodiment of the multi-lumen catheter of the present invention having a tapered tip;

FIG. 19 is a longitudinal cross-sectional view of the distal portion of the catheter of FIG. 18 showing the stiffening rod positioned through the central lumen of the catheter over the guidewire;

FIG. 20 is a perspective view of a distal portion of yet another alternate embodiment of multi-lumen catheter of the present invention;

FIG. 21A is a perspective view of a first embodiment of a trocar of the present invention having a barbed proximal end for attachment to the catheter for creating a subcutaneous tissue tunnel and for pulling the catheter through the tissue tunnel;

FIG. 21B is a perspective exploded view of an alternate embodiment of the trocar of FIG. 21A having a removable handle;

FIG. 21C is a close up view of the connecting structure of the trocar of FIG. 21B;

FIG. 21D is a close up view of an alternate embodiment of the trocar having a threaded connecting structure;

FIG. 21E is a perspective view of the trocar of FIG. 21B being inserted through a subcutaneous tissue tunnel;

FIG. 21F is a transverse cross-sectional view taken along lines 4-4 of FIG. 21E showing the latch for releasably connecting the trocar of FIG. 21B to the handle;

FIG. 21G is a cross-sectional view showing the threaded connection of the trocar of FIG. 21D to the handle;

FIG. 21H is a perspective view of another alternate embodiment of the trocar having a series of threads distal of the barbed fitting;

FIG. 21J is a perspective view of an alternate embodiment of a trocar with a proximal end configured for insertion into a distal end of the catheter;

FIG. 21K is an enlarged side view of the proximal end of the trocar of FIG. 21J;

FIG. 21L is a perspective view showing insertion of the trocar of FIG. 21J into the distal end of the catheter;

FIG. 21M is a perspective view showing the trocar of FIG. 21J attached to the catheter.

FIG. 22 illustrates an alternate embodiment of the trocar of the present invention having a lumen for receiving a guidewire;

FIG. 23 illustrates the trocar of FIG. 22 being withdrawn after a subcutaneous tissue tunnel has been created;

FIG. 24A is a bottom view of another alternate embodiment of the trocar of the present invention having a lumen for receiving a guidewire;

FIG. 24B is a longitudinal cross-sectional view of the distal end portion of the trocar of FIG. 24A;

FIGS. 25-28 illustrate the surgical method steps for inserting the multi-lumen catheter of FIG. 3 through the right internal jugular vein and superior vena cava into the right atrium wherein:

FIG. 25 shows the introducer needle being inserted through the right jugular vein and the guidewire being inserted through the right jugular vein, through the superior vena cava and into the right atrium;

FIG. 26 illustrates the needle introducer removed leaving the guidewire in place in the right internal jugular vein, superior vena cava and right atrium;

FIG. 27 illustrates the trocar of FIG. 22 being inserted through a first incision site and exiting a second incision site to create a subcutaneous tissue tunnel adjacent the incision site for the introducer needle;

FIG. 28C illustrates the multi-lumen catheter of FIG. 3 inserted over the guidewire through the tissue tunnel, and curved down into the right internal jugular vein, superior vena cava and right atrium;

FIGS. 29A-29G illustrate the steps for an alternate method of inserting the multi-lumen catheter of FIG. 3 through the right internal jugular vein and superior vena cava into the right atrium wherein the trocar creates a tissue tunnel with an exit opening at the incision cite where the needle and guidewire are introduced, wherein:

FIG. 29A illustrates the trocar of FIG. 22 inserted over the guidewire through a first incision site, creating a subcutaneous tissue tunnel, and exiting the incision site created for insertion of the introducer needle and guidewire;

FIG. 29B illustrates the trocar being removed, leaving the guidewire in place extending through the tissue tunnel and forming a loop adjacent the needle incision site; and FIG. 29C illustrates the multi-lumen catheter of FIG. 3 being inserted over the guidewire for passage through the tissue tunnel;

FIG. 29D illustrates the catheter inserted through the subcutaneous tissue tunnel and forming a loop corresponding to the loop formed in the guidewire;

FIG. 29E illustrates the catheter extending through the subcutaneous tissue tunnel and being inserted further along the guidewire down into the right internal jugular vein;

FIG. 29F is a view similar to FIG. 29E except showing the guidewire being removed; and FIG. 29G illustrates the catheter in place extending through the subcutaneous tissue tunnel and advanced into the right internal jugular vein, superior vena cava and right atrium;

FIG. 30 illustrates an alternate method of retracting the guidewire through the subcutaneous tissue tunnel formed by the trocar;

FIGS. 31-37 illustrate a method for manufacturing a first embodiment of the hub of the multi-lumen catheter of FIG. 3 wherein:

FIG. 31 illustrates a slit formed in the outer wall of the catheter;

FIG. 32 is a view similar to FIG. 31 except showing in phantom the central arterial lumen of the catheter;

FIG. 33 is a transverse cross-sectional view taken along lines 33-33 of FIG. 32;

FIG. 34 illustrates a pin inserted through the slit in the outer wall of the catheter;

FIG. 35 illustrates the tubing inserted over the pin;

FIG. 36 illustrates the injection of soft material over the pin and catheter tube to form the catheter hub which retains the lumen connector tubes in position;

FIG. 37 illustrates the hub resulting from the injection molding process enabling one connector to communicate with the inflow (arterial) lumen and the other connector to communicate with the multiple outflow (venous) lumens;

FIGS. 38-40 illustrate an alternate embodiment of the hub of the multi-lumen catheter of FIG. 3 wherein;

FIG. 38 illustrates a perspective view of the proximal end of the catheter body split into five segments to accommodate the separate connector tubes;

FIG. 39 is a perspective view illustrating the connector tubes inserted into the respective lumens of the catheter body; and FIG. 40 is a transverse cross-sectional view illustrating the cuts made in the catheter wall to form the separate segments.

FIG. 41 is a perspective view of another alternate embodiment of the hub of the catheter of the present invention having the lumen configuration of FIG. 9C;

FIG. 42 is an exploded view of the hub and tube structure of FIG. 41;

FIG. 43 is an enlarged perspective view showing the transition of the venous holes from a substantially oval to a substantially round configuration at the flared proximal portion of the catheter; and FIG. 44 is an enlarged perspective view showing the multi-lumen extension tube tapering proximally and transitioning from substantially circular venous holes to substantially triangular holes;

FIGS. 45-54 illustrate an alternate preferred embodiment of the dialysis catheter of the present invention, wherein FIG. 45 is a perspective view of the catheter;

FIG. 46 is a perspective view similar to FIG. 45 except showing the stiffener rod positioned therein;

FIG. 47 is an enlarged perspective view of the catheter tip showing the return and intake lumen openings;

FIG. 48 is a side view of the catheter tip;

FIGS. 48A, 48B and 48C are transverse cross-sectional views taken along lines A-A, B-B and C-C, respectively, of FIG. 48;

FIG. 49A is a longitudinal cross-sectional view of a distal portion of the catheter showing the stiffener rod extending through the catheter;

FIG. 49B is a side view of the stiffener rod of FIG. 49A;

FIG. 50 is a perspective view showing the arterial extension tubes extending from the proximal flared portion of the catheter, the venous extension tube is removed for clarity;

FIG. 51 is a side view of the proximal end of the catheter, with one of the hub halves removed, showing the extension tubing connections to the catheter lumens;

FIG. 52 is a perspective view of a proximal portion of the arterial extension tubing illustrating the funneled surfaces for wire insertion;

FIG. 53 is a transverse cross-sectional view taken along lines D-D of FIG. 46 showing the lead in for the cleaning wire insertion; and FIG. 54 is a transverse cross-sectional view taken along lines E-E of FIG. 50 showing the arterial extension tubes within the sheath.

FIG. 55 is a perspective view of the proximal end portion of an alternate embodiment of the catheter of the present invention showing the extension tubing and clamps;

FIG. 56 is an exploded view of the catheter of FIG. 55;

FIG. 57A is a perspective view of a distal end portion of the catheter; and

FIG. 57B is a transverse cross-sectional view illustrating the lumen configuration of one embodiment of the catheter;

FIG. 57C is a transverse cross-sectional view illustrating the lumen configuration of an alternate embodiment of the catheter;

FIGS. 58A and 58B are side and perspective views, respectively, of the arterial clamp shown in the open position;

FIGS. 59A and 59B are perspective and top views, respectively, of the arterial tag;

FIG. 60 is a perspective view of the adapter;

FIG. 61A is a perspective view of the venous clamp in the neutral position;

FIGS. 62A and 62B are perspective and top views, respectively, of the venous tag;

FIG. 63 is an enlarged view of the arterial clamp shown in the open position and further showing a portion of the venous clamp, a portion of the arterial and venous tags removed for clarity; and FIG. 64 is an enlarged view of the venous clamp shown in the neutral position and further showing a portion of the arterial clamp.

DETAILED DESCRIPTION OF PREFERRED EMBODIMENTS

Figure 1:
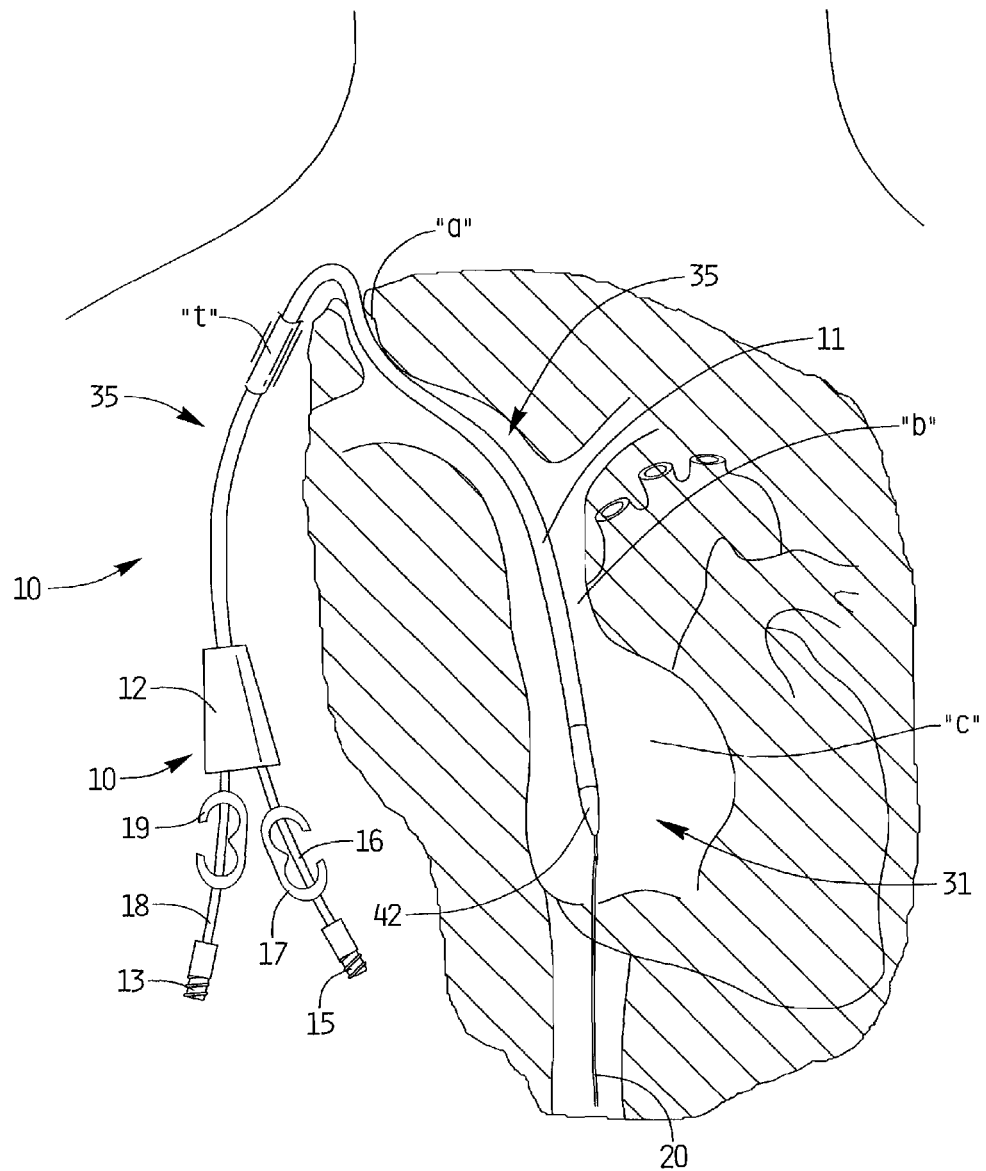
FIG. 1 is a plan view of a first embodiment of the multi-lumen catheter of the present invention being inserted through the right internal jugular vein and superior vena cava into the right atrium of a patient's body.

Referring now in detail to the drawings where like reference numerals identify similar or like components throughout the several views, the first embodiment of the catheter of the present invention is designated generally by reference numeral 10. The catheter 10 is typically inserted into an area of high velocity blood flow to ensure sufficient blood can be transported from the body for dialysis. FIG. 1 illustrates the catheter 10 inserted through the right internal jugular vein "a", into the superior vena cava "b", and into the right atrium "c"; FIG. 2 illustrates the catheter 10 inserted into the left internal jugular vein "d", into the superior vena cava "b" and into the right atrium "c". Insertion into the right atrium, from either the right or left side provides the necessary high blood flow to the dialysis machine. Note that the catheter body (catheter tube) 11 is sufficiently flexible to enable it to bend to accommodate the anatomical curves as shown.

Catheter 10 has a catheter body or catheter tube 11 having a distal end portion 31, a proximal end portion 33, and an intermediate portion 35. Distal portion 31 terminates in nose 32 which is illustratively substantially conical in shape. Proximal end portion 33 includes hub 12, where the lumens formed within catheter tube 11 are connected, i.e. transition, to the respective inflow and outflow tubes, 16, 18, respectively, to enable return and withdrawal of blood for dialysis. Conventional tube clamps 17 and 19 cut off blood flow through inflow and outflow tubes 16, 18 as desired. As used herein, the terms "inflow" and "outflow" refer to the direction of blood flow with respect to the catheter such that "return", "delivery" or "venous flow" refers to flow from the dialysis machine and delivered to the body while "intake", "withdrawal" or "arterial flow" refers to flow withdrawn from the body and transported to the dialysis machine.

As shown, intermediate portion of catheter 10 extends through subcutaneous tissue tunnel "t", and curves downwardly toward the target site, e.g. the right atrium. This tunnel "t" secures the catheter in place for dialysis for a period of weeks, or even months, with fibrous cuff 36 (FIG. 3) enabling tissue ingrowth. The formation of the tunnel "t" and the insertion of the catheter 10 therethrough will be discussed below in conjunction with the discussion of the catheter insertion method.

It should be appreciated that although the catheter is shown emerging from the tissue tunnel "t" at a second incision site, preferably, the tissue tunnel would not have an exit opening at a second site but instead would exit through the same incision through which initial access is made by the needle and dilator into the internal jugular vein "a". This is described in more detail below.

A series of lumens are formed in catheter tube 11 for transporting blood to and from a dialysis machine. As is well known in the art, a dialysis machine essentially functions as a kidney for patients suffering from kidney failure. Blood is removed from the patient and transported to the dialysis machine where toxins are removed by diffusion through a semi-permeable membrane into a dialysis fluid. The filtered blood is then returned through the catheter body to the patient.

More specifically, and with reference to FIGS. 5, 6A, 7 and 8, details of the catheter lumens will now be described. Central longitudinal lumen 40 is formed within catheter tube 11, extends the entire length and is designed to transport filtered blood to the patient. Lumen 40 is also configured to receive a guidewire 20 to direct the catheter to the desired position. Lumen 40 extends to nose 42, and terminates in region 37 where it aligns with central longitudinal lumen 41 of nose 42.

Central lumen 41 of nose 42 communicates with narrowed lumen 45, terminating in distal opening 47 to communicate with the patient's body so blood can be delivered through distal opening 47. Lumens 41 and 45 also receive guidewire 20. Thus, lumen 40, lumen 41 and narrowed lumen 45 together form a central lumen enabling blood to be delivered from the dialysis machine to the patient. The transition from lumen 41 into narrowed lumen 45, forms a stop or shoulder 43, the function of which will be described below.

Nose 42 also includes side venous (delivery) openings 46 formed through the outer wall 44 wall in fluid communication with lumen 41, also functioning to return blood to the patient's body. Side openings or ports 46 are preferably angled outwardly as shown to facilitate delivery of blood in the direction of blood flow and lessen mechanical hemolysis. These additional openings help maintain the desired flow volume by distributing the blood through multiple holes. Although only four openings are shown, it is contemplated that additional or fewer openings can be provided and the openings can be axially displaced with respect to each other. Additional set(s) of openings can also be provided spaced proximally or distally from side openings 46.

In this embodiment, nose 42 forms the distal tip portion and is composed of a different material than the other portions of the catheter body 11 and is welded or attached by other means to the catheter body 11. The tip (nose) in this embodiment is composed of a stiffer material to facilitate tunneling and blunt dissection through tissue. The nose could alternatively be composed of a softer material, thereby being less traumatic upon contact with the vessel wall. However, in a preferred embodiment, the nose is composed of the same material as the catheter body, having a small stiffener member embedded therein. This configuration is described in detail below in conjunction with FIGS. 13-15.

Catheter 10 also has a series of arterial (withdrawal) lumens 34a-34e, extending longitudinally along the length of the catheter body 11, each terminating at surface 48 of nose 42. In the preferred embodiment, shown in the cross-sectional view of FIG. 8, the lumens 34 are oval-like in configuration, with opposite curved walls 37a, 37b and opposite substantially flat walls 39a, 39b. These spaced apart lumens have solid material between them therefore increasing the structural integrity of the catheter body 11. The lumens 34a-e are independent from one another through the distal, intermediate and proximal portions 33, 35, 31 of the catheter body 11, until the hub 12 where the lumens 34a-34e connect to a common connector tube. This is described in more detail below. Lumens 34a-34e, as shown, are symmetrically positioned and radially displaced from the central return lumen 40.

With continued reference to FIGS. 5 and 6A, a series of side openings or ports 50 are provided in the outer wall 14 of catheter body 10. These openings 50a, 50b, 50c, 50d, and 50e are each in fluid communication with a respective intake lumen 34a-34e and are designed and configured to withdraw blood from the patient's body for delivery to the dialysis machine. A second set of openings 52a-52e, spaced proximally from openings 50a-50e, is also in communication with a respective lumen 34a-34e. Only three of the side openings 50, 52 are shown in FIG. 5, it being understood that the other three openings are positioned on the other side of the catheter, preferably symmetrically placed to accommodate the circumferential arrangement of the intake lumens 34a-34e.

Although lumens 34a-34e are isolated along a substantial length of the catheter, they preferably have a common flow source at the proximal portion 33 of the catheter 10. This is described in more detail below.

In the embodiment of FIG. 8, the venous (return) lumen size preferably ranges from about 0.006 inches to about 0.008 inches$^2$ in cross-sectional area, and is more preferably 0.007 inches$^2$. The cross-sectional area of each of the arterial (intake) lumens 34 preferably ranges from about 0.002 inches to about 0.004 inches$^2$, and more preferably about 0.003 inches$^2$, bringing the total cross-sectional area of the intake lumens to about 0.01 inches to about 0.02 inches$^2$, and more preferably about 0.015 inches$^2$. This means that the ratio of total cross sectional area of the return lumen to the intake lumens is about 1 to about 2.1. Other dimensions are also contemplated.

It should be appreciated that although five separate lumens 34 are shown, a fewer or greater number can be provided. Also, although two sets of side openings are shown (set 50 and set 52), a fewer or greater number of sets can be provided, and a fewer or greater number of openings in each set could be provided.

Alternative lumen configurations spaced circumferentially are illustrated in FIGS. 9A, 9B, 9C and 10. In FIG. 9B, three arc-shaped lumens 60a, 60b, 60c are positioned around the arterial central lumen 40'. These larger sized lumens provide for additional arterial (intake) flow but result in the reduction of the strength of the catheter wall due to the less wall material as compared to the lumen configuration of FIG. 8. In FIG. 9A, five lumens 66a, 66b and 66c are provided. These lumens have more of a rectangular (or trapezoidal) shape with one pair of opposing walls having a straighter configuration than the lumen configuration of FIG. 8. As shown, the other pair of opposing walls has a slight curvature. In FIG. 9C, four oval-like intake lumens 76a, 76b, 76c and 76d are positioned around a substantially square central lumen 78. This lumen configuration provides for a substantially sized central lumen and sufficient room between the central lumen 78 and each of the intake lumens 76a-76d for the catheter walls to flex. In FIG. 10, five lumens 70a-70e of circular cross-section are provided around the central lumen 40", adding to the stability of the catheter by increasing the wall material, but reducing the overall venous lumen size as compared to the embodiment of FIG. 8. Preferably, the intake (arterial) lumens in each of these embodiments are independent from one another along the substantial length of the catheter.

Fewer or greater number of lumens could be provided and lumens of other configurations are also contemplated. This positioning of the intake lumens in a circle-like array around the catheter, i.e. radially displaced from the center of the catheter, more evenly distributes the vacuum, as compared to a side by side venous/arterial lumen configuration, and ensures constant return flow since if one of the lumens becomes stuck against the vessel wall or otherwise clogged, the remaining lumens will maintain adequate flow. The openings in the sidewalls communicating with the lumens can also be elongated instead of circular, creating a series of longitudinally extending openings for entry of suctioned blood. This version of elongated openings is shown for example in FIGS. 18 and 20 described in detail below.

Figure 49:
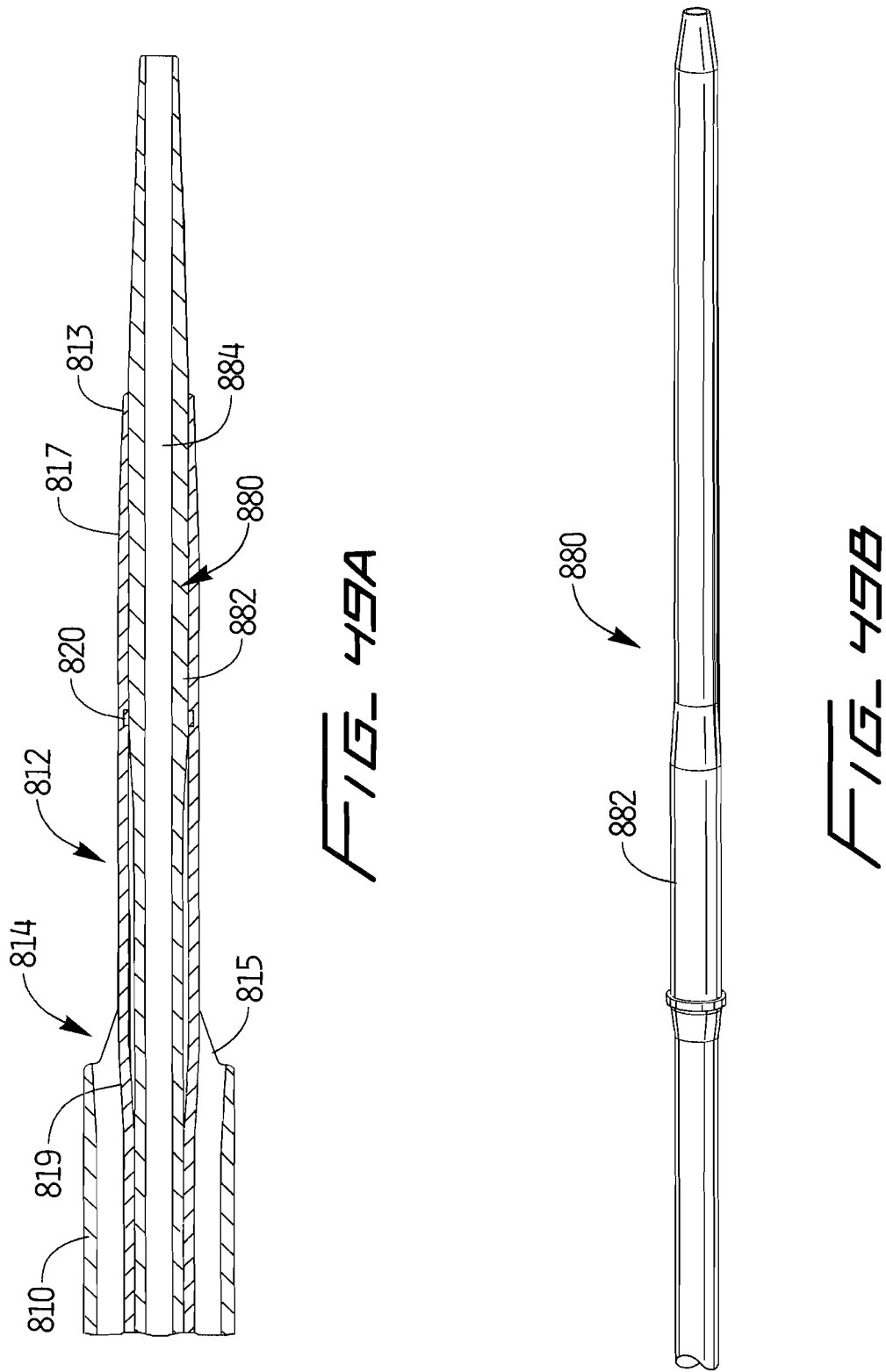

To facilitate insertion, the catheter is configured to receive a stiffening member in the form of a stiffening rod which stretches the catheter to reduce its profile to aid in over the wire insertion and better navigate through small vessels. That is, the stiffening rod is inserted into central lumen 40 of catheter 10 and torqued to stiffen the flexible catheter for ease in over the wire insertion and navigation through the small vessels, and to reduce the outer diameter of the catheter body by stretching it during insertion. After placement of the catheter 10, the stiffening rod is removed, allowing the catheter to return to its higher profile position with the lumens of the necessary size for blood transport to and from the body. Two embodiments of the stiffening rods are illustrated in FIGS. 4A and 4B and are shown prior to insertion into the catheter 10 in FIG. 3. A third embodiment of the stiffening rod is illustrated in FIG. 49.

Turning to the first embodiment of the stiffening rod illustrated in FIG. 4A, the stiffening rod is designated generally by reference numeral 80. Stiffening rod 80 has a distal tip 82, a proximal end portion 85 and an internal lumen 87 extending therethrough (see FIG. 11). Stiffening rod 80 is inserted through the proximal end of inflow tube 16, in the direction of the arrow of FIG. 11, over the guidewire 20 (which extends through lumen 87 and through central lumen 40) until distal tip 82 abuts shoulder or stop 43 as shown in FIG. 12. The proximal end portion 85 of stiffening rod 80 has a threaded portion 81 which is screwed onto screw thread 15 of inflow tube 16. This temporarily secures the stiffening rod 80 within the catheter 10 during insertion. This threaded mounting requires the stiffening rod 80 to be manually twisted, thereby torquing rod 80 as it presses forwardly and applies a force against shoulder (abutment surface) 43 to stretch the catheter body 11 to reduce its outer diameter. It is contemplated in one embodiment, for example, that the catheter body 11 can be reduced in diameter from about 0.215 millimeters to about 0.207 millimeters by the stiffening rod 80. (Other size reductions are also contemplated). This reduction in catheter body diameter or profile is represented by the arrows D1 and D2 in FIGS. 11 and 12, respectively, which show the change in dimension effectuated by the stiffener rod 80.

After the catheter 10 is positioned at the desired site, the stiffening rod 80 is unthreaded from the proximal thread 15 of venous (return) tube 16 and removed from the central lumen 40 of the catheter 10 and from the venous (return) tube 16, thereby allowing the catheter to return to its normal profile of FIG. 11.

It should be appreciated that stiffening rod 80 can alternatively be temporarily attached at its proximal end to the tube 16 by other means such as a bayonet lock, snap fit, etc. The rod could first be manually twisted and then mounted by these various means for retention in its torqued position.

An alternate embodiment of the stiffening rod is illustrated in FIG. 4B and designated generally by reference numeral 90. Stiffening rod 90 has a threaded distal end 92 which is threaded onto internal threads 251 of catheter 200 shown in FIG. 6B. A series of proximal threads 91 are screwed onto the threads 15 of the inflow tube 16 in the same manner as described above for stiffener rod 80. The stiffening rod 90 functions in the same manner as stiffening rod 80, i.e. to stretch the catheter during insertion to reduce its profile and to stiffen it to facilitate insertion, the only difference being the mechanical threaded attachment of the distal end of the stiffening rod 90 to the catheter 200 instead of the abutting relation of stiffening rod 80 with shoulder 43 of catheter 10. Preferably, the distal threads 92 are first threaded onto internal thread 251, followed by attachment of the proximal threads 91 as the stiffening rod 90 is torqued. Stiffening rod 90, like stiffening rod 80, is preferably circular in cross-section, although other configurations are also contemplated.

Catheter 200 of FIG. 6B is identical to catheter 200 in all respects except for the threads 251 instead of shoulder 43 and lumen 241 which is uniform in diameter. Similar to catheter 10, catheter 200 has distal return opening 247 and side openings 246 in outer wall 244 communicating with lumen 241 in distal tip portion 242, which communicates with central lumen 40. Arterial intake lumens 234a-234e terminate at wall 248 and have respective side openings 252a-252e and 250s-250e formed in the outer wall 214. Only one of the side openings 250a, 252a are shown in the longitudinal cross-sectional view of FIG. 6B.

As noted above, distal tip (nose) can be composed of a different stiffer material than the catheter body 11 or can be composed of a material having a higher durometer than the catheter body. This stiffer material will facilitate both tunneling through and dilating tissue. In an alternate preferred embodiment, however, the distal tip is composed of the same material as the catheter body but has a stiffening insert.

More specifically, the alternative nose (tip) configuration is illustrated in FIG. 15, with the method of manufacturing the tip shown in FIGS. 13 and 14. This nose or distal tip 104, is composed of the same material as the catheter body 108 and has a stiffening insert 110 inserted through central lumen 106 of nose 104. Central lumen 106 extends through the catheter body. The stiffening insert 110 is preferably composed of the same material as the catheter body 11 and nose 104, except it is made of a harder durometer material such as 72 shoreD vs. 85 shoreA for the catheter body 11. The material utilized can be, by way of example, urethane. For convenience, only the distal tip is shown, the remaining portions of the catheter 100 being identical to catheter 10.

The stiffening insert 110, preferably cylindrical as shown, has a hole 112 for receipt of the guidewire and for communication with central lumen 106. Insert 110 engages the inner wall surface 114 of central lumen 106. Lumen 106, proximal of side openings 119, will include either a stepped portion to provide an abutment surface (shoulder) for stiffening rod 80 or internal threads to mount stiffening rod 90 as described above.

The method of manufacturing this bullet shaped nose 104 will now be described in conjunction with FIGS. 13-15. Once cylindrical tube is formed, preferably by injection molding techniques, with central return lumen 106 and intake lumens 109a-109e, stiffening insert 110 is placed within central lumen 106 at the distalmost end and substantially flush with the distalmost edge 102 of the cylindrical tube.

Once the stiffening insert or slug 110 is placed within central lumen 106, the tube is formed into the bullet nose shape of FIGS. 15A and 15B, by a conventional radiofrequency or other heating process which allows the tip material to flow and form around the harder insert 110. After heating of the die and formation into this configuration, the material is cooled and thereby hardens to the configuration of FIG. 15 as the material fuses to the insert 110. A conventional core pin (not shown) can be used, inserted through the hole 112 and central lumen 106 during the forming process. When the material hardens, the pin is withdrawn to maintain these openings. After the forming process, side holes 114 are either cut or drilled through the wall 108 of catheter 100 to communicate with lumen 106 in the same manner as side holes 46 communicate with central lumen 40 of FIGS. 1-6.

FIGS. 16A-17C illustrate two alternate embodiments of the catheter of the present invention having spacers to minimize contact of the catheter body with the vessel wall. Provision of these spacers is optional. In the embodiment of FIGS. 16A-16C, catheter 150, similar to catheter 10, has a distal portion having a nose 154, a central return lumen 156 which also receives a guidewire 20, and a series (e.g. 5) of intake lumens 160-160. Venous return lumen 156 communicates with lumen 151 and narrowed lumen 153 of the nose 154, terminating in open distal end 158. A plurality of side openings 159 communicate with lumen 151 and function in the same manner as side openings 46 of catheter 10. Arterial intake lumens 160 each terminate at side openings 161, similar to side openings 52 of intake lumens 34 of catheter 10.

Although only one series of side openings 161 are shown, clearly additional arrays of side openings, positioned distally or proximally of side openings 161 could be provided. The arterial lumen configuration can also vary in a similar manner as described above with respect to catheter 10. Thus, except for the spacers, catheter 150 is identical to catheter 10.

A plurality of spacer wires 164 are embedded in the wall 169 of the catheter 150 and are secured at region 158 by adhesive or other suitable means. In the normal configuration, spacer wires 164 bow slightly outwardly with respect to the outer wall 169 of the catheter 150 to reduce the likelihood of contact with the vessel wall. When the stiffening rod 80 is inserted over guidewire 20 and through central lumen 156, as shown in FIG. 16C, and edge 170 is forced against the abutment surface or stop 159, the catheter body is stretched and the spacer wires 164 stretch to a straightened position, substantially flush with the outer surface of wall 169. This reduces the profile of the catheter and ensures the spacer wires do not interfere with catheter insertion. When the stiffener rod 80 is withdrawn, the catheter returns to its normal position, and the spacer wires 164 bow outwardly as in FIGS. 16A and 16B. It should be appreciated that stiffening rod 90 can also be used with catheter 150 and would function to reduce the profile in the same manner as rod 80. Catheter 150 would then be provided with internal threads for mounting stiffening rod 90 as described above.

An alternative to spacer wires is illustrated in FIGS. 17A-17C. Catheter 180 is identical to catheter 150, except it is provided with integral ribs 194 proximal of nose 184. That is, similar to catheter 150, catheter 180 has a central return lumen 186 configured to receive guidewire 20 and stiffening rod 80 or 90. Lumen 186 communicates with lumen 181 and narrowed lumen 183 of the nose 184 which terminates in open distal end 188. Side openings 189 of nose 184 communicate with lumen 181. A series of independent intake lumens 190 are provided, terminating in side openings 192, similar to side openings 161 of catheter 150. Although only one series of side openings 192 are shown, clearly additional arrays, positioned proximally or distally of side openings 192 could be provided.

Spacer ribs 194 are formed by cutout portions in the wall 193 of the catheter 150. FIG. 17B illustrates the spacer ribs 194 in their normal position, outwardly bowed from the outer surface of the wall 193 of the catheter body. FIG. 17C illustrates the straightened or retracted position of the spacer ribs 194, where the ribs 194 are substantially flush with the outer surface of wall 193, after stiffener rod 80 of FIG. 4A (or rod 90 of FIG. 4B) is inserted through central lumen 186 to stretch the catheter 150 for insertion in the manner described above.

FIGS. 18 and 19 illustrate another alternative embodiment of the catheter of the present invention. Catheter 500 has a distal tip 502 with a tapered region 510 transitioning to a reduced diameter region 504. The central lumen terminates in distal opening 506 for fluid delivery. Unlike the previously described embodiments, the distal opening 506 is the sole fluid delivery passageway into the body. However, it is also contemplated that additional side holes could be provided in the tip to provide additional venous ports for blood delivery to the patient.

A series of intake (arterial) openings 508 (only two are shown in the view of FIG. 18) are provided in the transition or tapered region 510 of the tip 502. These openings are elongated to provide additional area for suctioning. Each of the openings 508 communicates with a respective arterial lumen 510 formed in the catheter. The venous lumen configuration (and arterial lumen configuration) can be in the form of those illustrated in FIGS. 7-10, or other variations, as described above.

Stiffening rod 520 is shown positioned in the central lumen of the catheter 500. Rod 520 is similar to the rods 80 and 90 described above except it extends distally of the distal tip 502 of catheter 500, has a tapered distal end 524 to facilitate tunneling and dilating tissue, and has a stepped portion to abut the internal structure of the catheter 500. More specifically, guidewire 20 is shown extending through the central lumen of stiffening rod 520. The stiffening rod 520 is inserted through the central lumen of catheter 500 and the stiffening rod 520 and catheter 500 are inserted over the guidewire 20, with the tapered tip 524 facilitating passage of the catheter as it dilates tissue.

Catheter 500 has a cylindrical insert 514 positioned in the distal tip, similar to insert 110 of FIG. 13A. The insert 514 is composed of a stiffer material to stiffen the tip of the catheter 500 to facilitate insertion. Insert 510 has an opening to receive stiffening rod 520 as shown. Shoulder 526 formed by stepped portion 524 abuts the insert 514, thereby functioning as a stop in a similar manner that shoulder 43 acts as a stop for stiffening rod 80 shown in FIG. 11, the difference being the shoulder is formed in the internal wall of the catheter rather than on the stiffening rod. Stiffening rod 520 thus acts in the manner as the aforedescribed rods 80, 90, i.e. pressing against the catheter tip portion to stretch the catheter for insertion, in addition to providing a tissue tunneling and dilation function.

FIG. 20 illustrates an alternative tip design of the catheter of the present invention. Catheter tip 602 has a bullet nose configuration, somewhat similar to the nose of FIG. 15, except having more of a progressive taper. Catheter tip 602 also has a series of elongated intake holes 608 (only two are shown in the view of FIG. 20). In all other respects, e.g. stiffening insert, stiffening rod, distal blood delivery opening 606, etc, catheter 600 is identical to catheter 500 of FIG. 18.

FIGS. 45-54 illustrate another alternate embodiment of the catheter of the present invention, designated generally by reference numeral 800. Catheter 800 has a catheter body or catheter tube 810 having a distal portion 812 and a transition portion 814 between the distal portion 812 and an intermediate portion 816 of the catheter. The proximal portion 818 of catheter body 810 has a flared region as will be described below.

Figure 45:
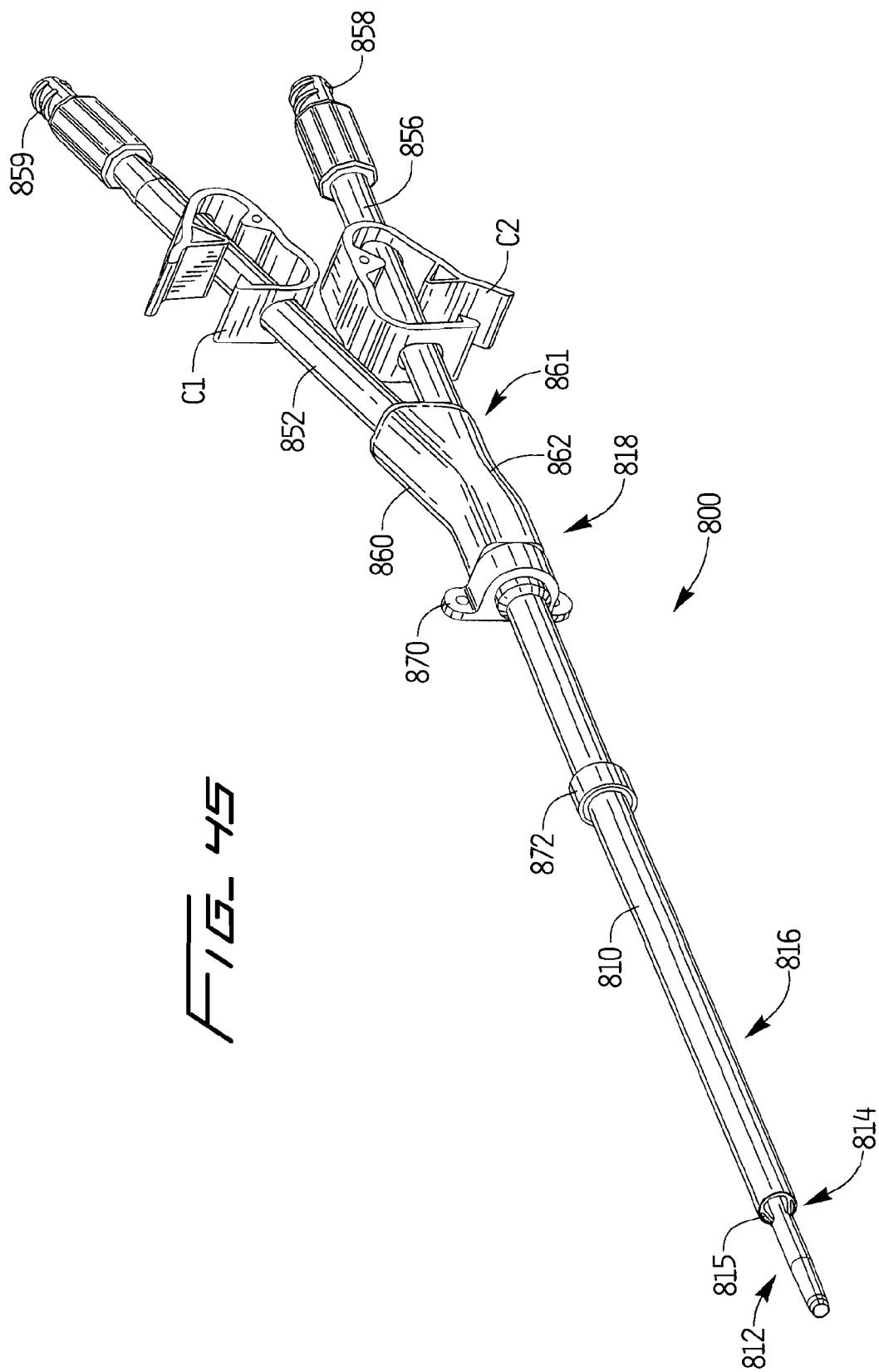
Figure 46:
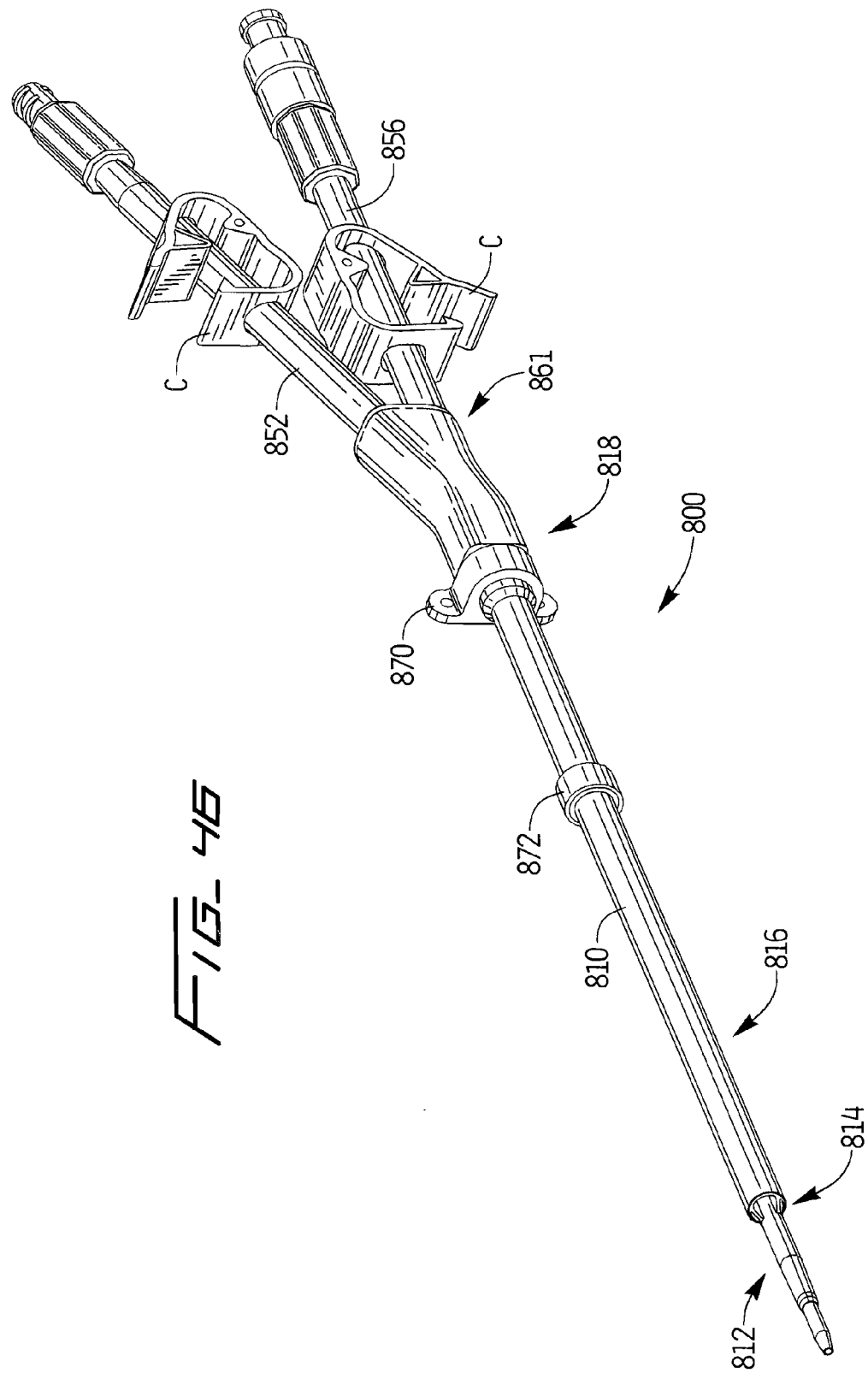
Figure 47:
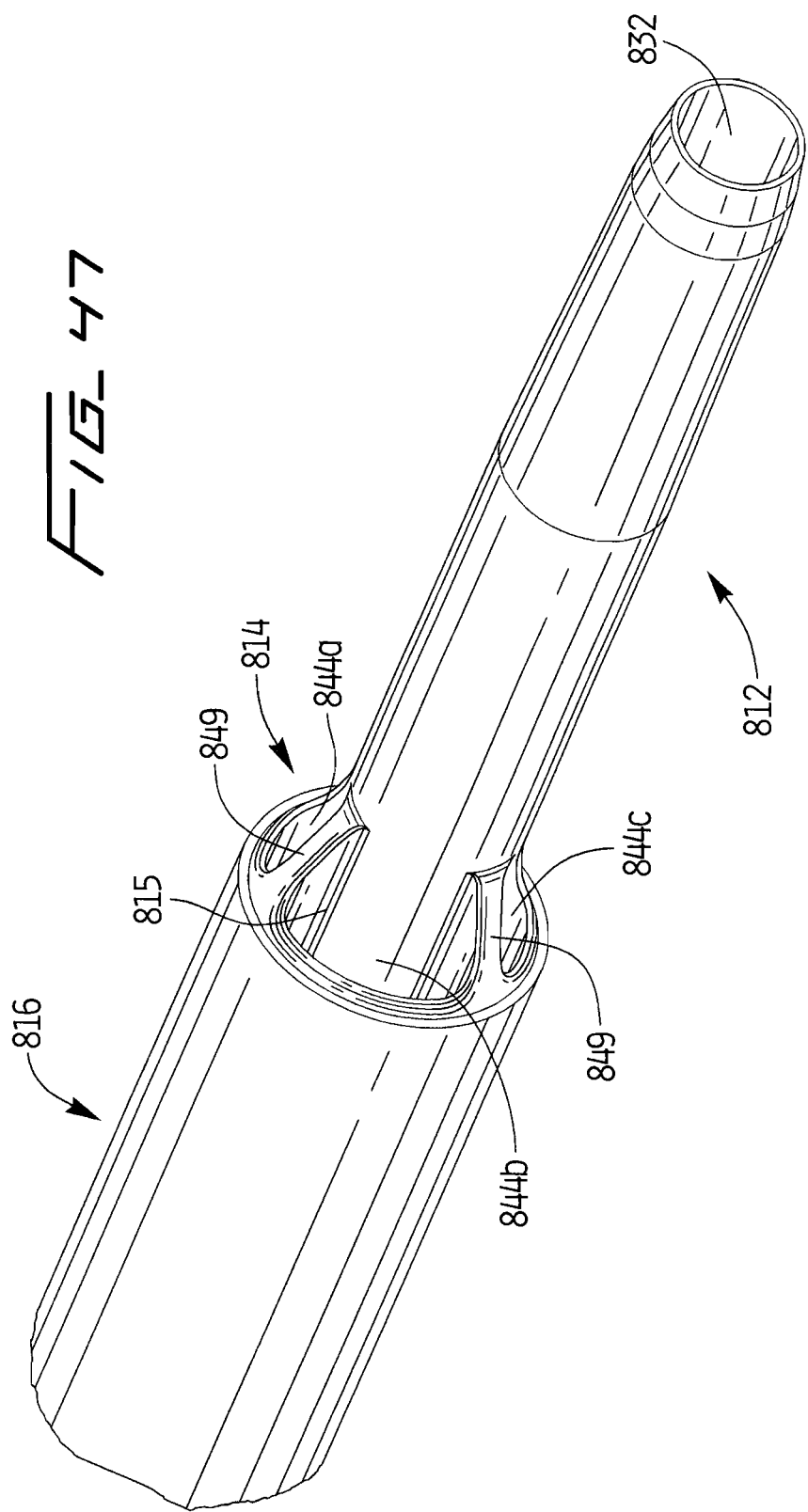

With reference to FIGS. 45 and 47, the distal portion 812 of catheter 800 is elongated and has a diameter less than the diameter of the intermediate portion 816. By way of example, in one embodiment, the diameter of the distal portion 812 can be about 0.118 inches and the diameter of the intermediate portion 816 can be about 0.218 inches. Clearly other dimensions are contemplated.

The transition portion 814 provides a smooth transition between the intermediate portion 816 and the distal portion 812 as it tapers in a distal direction. Formed in the transition portion 814 are four widened somewhat trapezoidal open areas, separated by ribs 849, each extending longitudinally to communicate with the intake openings. Thus, the intake openings terminate in longitudinally aligned openings at the transition portion 814.

The distal portion 812 has a non-uniform wall thickness with two tapered regions, best shown in FIG. 49. The wall thickness remains substantially constant until slightly proximal of the transition region 814 where it increases in thickness over a portion of the length, beginning at portion 819. The wall thickness of distal portion 812 then decreases towards the distal end at region 817 forming a first taper. A second taper 813 is formed at the distalmost end. In one embodiment the first taper at region 817 is about 2 degrees and the distalmost end taper at region 813 is about 5 degrees, although clearly other tapers are contemplated. These tapered regions provide for easier insertion of the catheter 800. Since the tapers are created by a change in wall thickness, the cross-sectional area of the central return lumen remains constant and the venous pressure is unaffected.

Embedded in the distal portion 812 is a stiffening insert 820 similar to the cylindrical stiffening insert 110 described in conjunction with FIGS. 13A-15B, except it is located proximal of the distalmost tip. The stiffening insert 820 is placed during formation of the catheter tube by melting the catheter material around the insert during formation in a similar fashion as insert 110.

Figure 48:
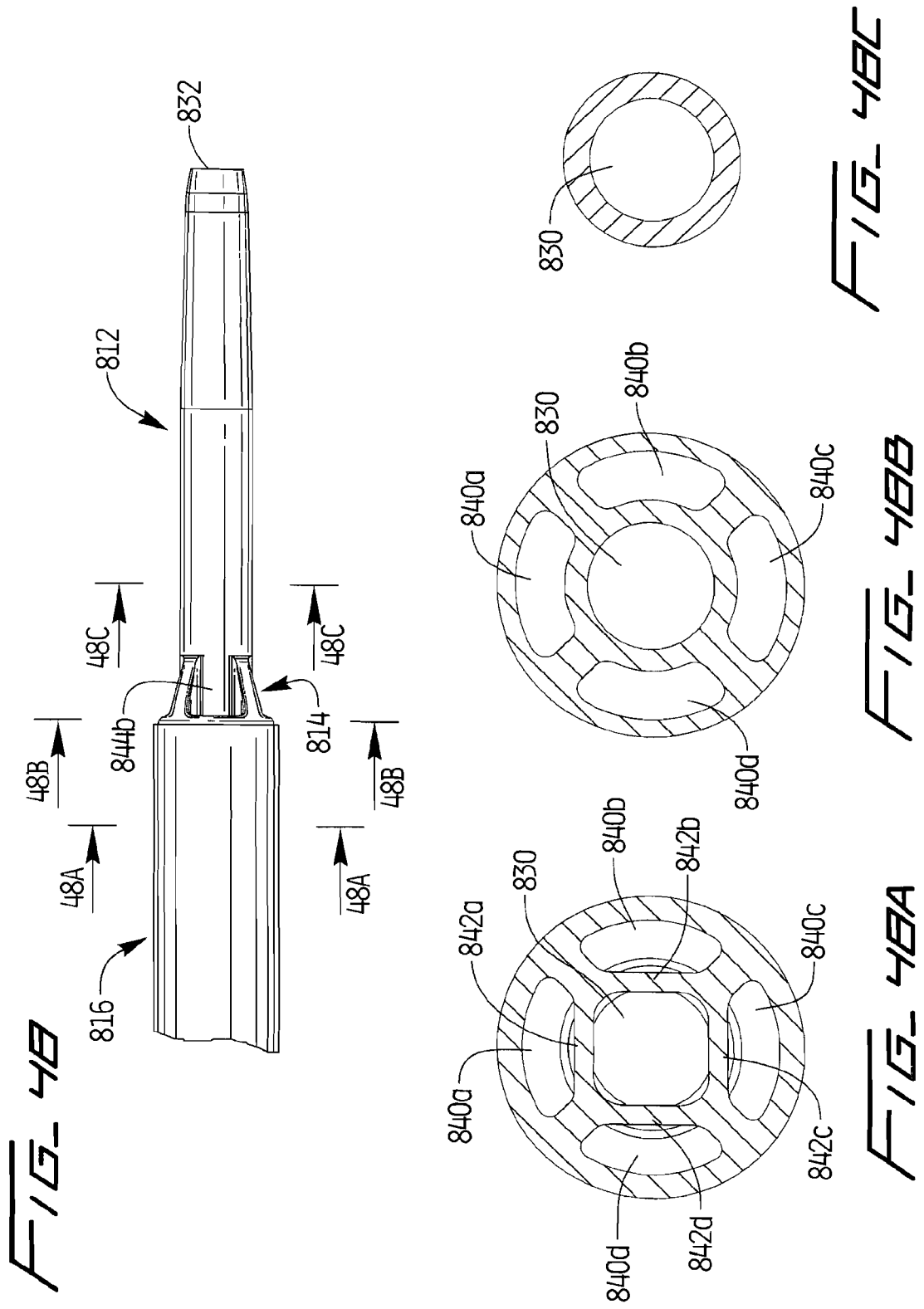

FIG. 48 illustrates the lumen configuration of the catheter 800 which is similar to the lumen configurations of FIG. 9C. A central return (venous) lumen 830 is encircled by a series of intake lumens 840*a*-840*d* in a spoke-like fashion. The central return lumen 830 is substantially square in cross-section with rounded corners as shown in FIG. 48A. The four intake lumens 840*a*-840*d* are oval-like in cross section with a substantially planar edge 842*a*-842*d* and opposing inwardly angled side walls. The central lumen 830 terminates in opening 832 at the distalmost end of the catheter tube 810. The intake lumens are independent and each terminates in an open area 844*a*-844*d* in the transition region 814 as described above.

In a preferred embodiment, the central return lumen 830 is of substantially constant cross-sectional area throughout its length. At the distal portion 812 the lumen 830 transitions to a more circular shape (FIG. 48B), but the cross-sectional area preferably remains the same. In a preferred embodiment, the cross-sectional area of the central lumen is about 0.007 inches$^2$, although other dimensions are contemplated. At the flared portion 821 (FIG. 50) the return lumen 830 transitions to a more circular configuration.

In the preferred embodiment, the intake lumens 840*a*-840*d* remain constant throughout their length until the proximal flared portion 821 where they are substantially circular (FIG. 50) and of greater cross-sectional area to receive the arterial extension tubes described below. The intake lumens 840*a*-840*d* transition to a more arcuate shape, as shown in FIG. 48B, just proximal of the transition region 814, but the cross-sectional area preferably remains the same. (This lumen configuration is similar to that of FIG. 9A in that it is more of a trapezoidal than oval shape with curved walls and inwardly angled substantially straight side walls). The cross-sectional area of each intake lumen 840 is preferably about 0.003 inches$^2$ so that the total intake cross-sectional area is preferably about 0.012 inches$^2$, but other dimensions for the intake lumens are contemplated.

Figure 50:
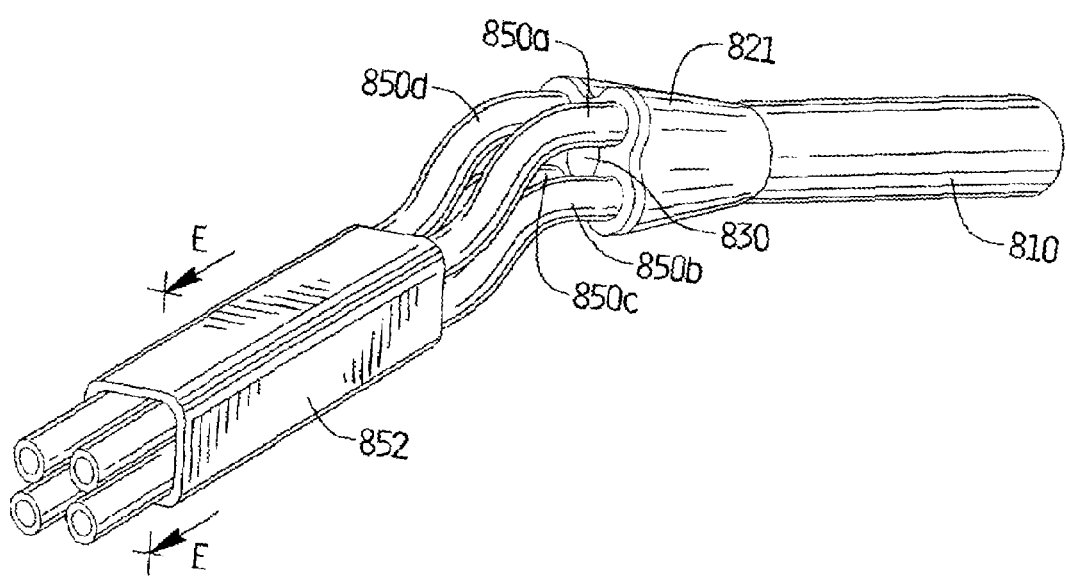

Turning now to the hub and tubing design for connecting the catheter 810 to the dialysis machine tubing, and with reference to FIGS. 50 and 51, four arterial extensions tubes 850*a*-850*d* are each placed in a respective intake lumen 840*a*-840*d* at the flared portion 821 to provide fluid communication. A sleeve 852 is attached during a thermal forming process to blend with the individual tubes 850*a*-850*d* to retain the four arterial extension tubes 850*a*-850*d* together. A connector tube or insert 854, preferably of stainless steel, is inserted into the central lumen 830 and a tapered venous extension tube 856 is placed over the tube 854 to provide fluid communication between extension tube 856 and central lumen 830. The two hub halves 860, 862 of hub 861 are snapped fitted over the region containing flared portion 821, connector tube 854, and a portion of extension tubes 850*a*-850*d*, 856 and sleeve 852 as shown in FIG. 51. Conventional arterial and venous clamps C1, C2, respectively, are illustrated in FIG. 45. In the preferred embodiment, a single arterial clamp C1 would clamp on the sleeve 852 to cut off flow simultaneously through all the arterial extension tubes 850*a*-850*d*. Thus separate arterial clamps would not be required. A luer lock 858 on venous extension tube 856 is for mounting the stiffener rod, and subsequent to insertion and after removal of the stiffener rod, for mounting tubing for connection to the dialysis machine. The luer lock for the arterial tubing mounts dialysis machine tubing.

A conventional suture ring 870 (FIG. 45), having suture holes for attaching the catheter, is fitted in an annular groove in the hub 861. A conventional fibrous cuff 872 for tissue ingrowth is shown at an intermediate section of the catheter 810 for tissue ingrowth as described above.

As described above, the catheters of the present invention are preferably inserted with the aid of a stiffening rod. FIG. 49 illustrates an embodiment of a stiffening rod for use with catheter 800 to temporarily increase the stiffness of the catheter to facilitate pushability (insertion) of the catheter. Stiffening rod 880 has a thickened wall portion 882 which engages an internal wall in the region of the catheter adjacent the region which contains the stiffening insert 820. Since this catheter region is not as flexible, it is not stretched at this region by the stiffener rod 880, thus providing resistance to distal movement of the stiffening rod 880, thereby holding it in place during insertion.

The proximal end of the stiffener is threaded onto venous luer 858 (FIG. 45). The increased wall thickness of stiffener rod 880 cooperates with the distalmost tip of the catheter 800 to prevent coring of tissue during insertion. The stiffener 880 protrudes past the distalmost tip of the catheter body 810 as shown, serving to help dilate tissue during insertion. Lumen 884 is dimensioned to receive a guidewire.

The arterial extension tubing includes a funneled lead in to facilitate insertion of standard guidewires to clear obstructions, e.g. clots and thrombus, in the catheter arterial lumens which may form over time. With reference to FIGS. 52-54, each of the quadrants within the sleeve has an inwardly directed curved inner wall 892*a-d* to create a funnel for the tubing entry region.

The method of insertion of the catheter of the present invention provides an entire over the wire system. This is achieved by the provision of trocar 300 illustrated in FIGS. 22 and 23. Trocar 300 has a lumen 304 formed therethrough (shown in phantom in FIG. 22) dimensioned for reception of guidewire 20. The lumen 304 extends the entire length of trocar 300, from a proximal opening 306 in handle 308 to a distal opening 310 (shown in phantom in FIG. 22) on the underside of the trocar 300 as viewed in FIG. 22. Distal opening 310 is adjacent the distal tip 302, at the region where it bends slightly upwardly. Note the lumen 304 of trocar 300 can be smaller than the outer diameter of the dialysis catheter, e.g. catheter 10, since it only needs to have an internal diameter of about 0.040 inches to about 0.045 inches to receive the guidewire. The diameter of the catheter is typically between about 0.170 inches and about 0.220 inches. The blunt distal tip 302 of trocar 300 bluntly dissects tissue to create a subcutaneous tissue tunnel for subsequent securement of the catheter.

FIGS. 24A and 24B illustrate an alternate embodiment of the trocar. Trocar 380 is similar to trocar 300 except for an elongated oval entrance opening 382 to lumen 383 for the guidewire and a beveled tip 384 to facilitate tunneling through tissue. The handle configuration 386 is also slightly different.

One method of use of the catheter will now be described in conjunction with FIGS. 25 to 28. The method will be described for inserting catheter 10, however it should be appreciated that any of the aforedescribed catheters can be inserted in the same manner.

Figure 28A:
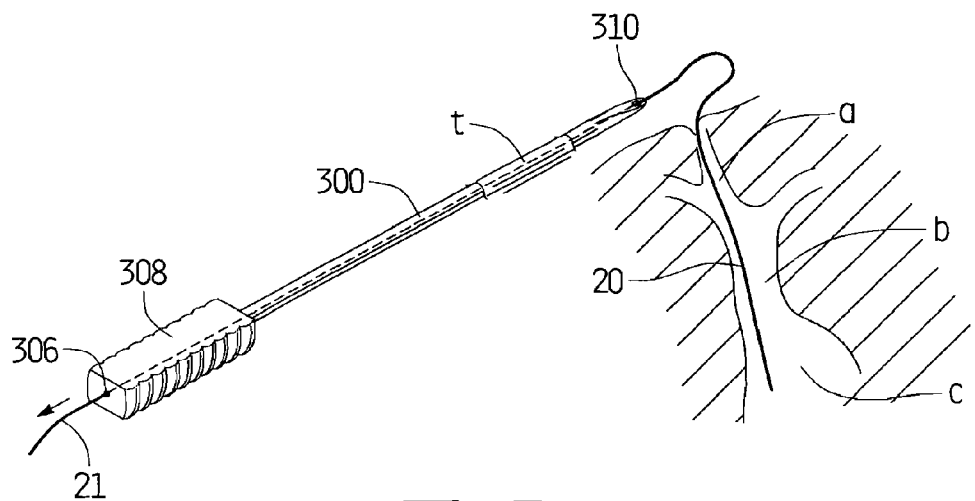
FIG. 28A illustrates the guidewire being threaded through the lumen of the trocar of FIG. 22.
Figure 28B:
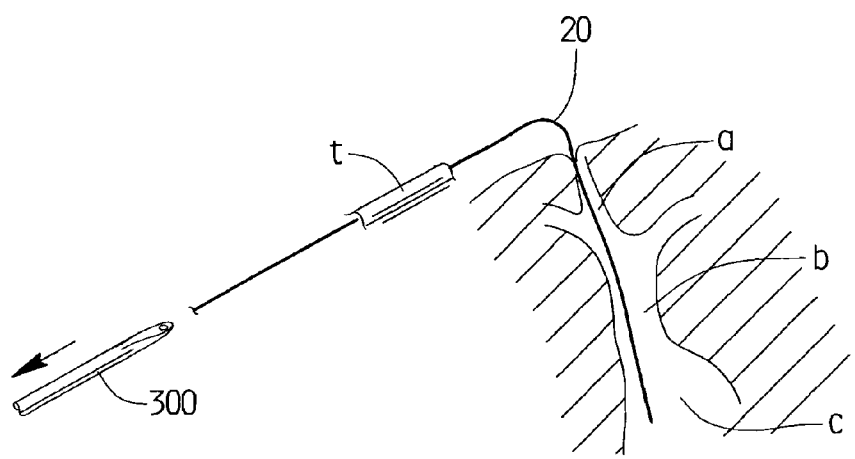
FIG. 28B illustrates the trocar being removed, leaving the guidewire in place extending through the tissue tunnel.

First, needle "N" is inserted into the internal jugular vein to properly locate the vessel and a guidewire 20 is inserted through the needle into the right internal jugular vein "a" and into the superior vena cava "b" as shown in FIG. 25. The guidewire 20 is further advanced into the right atrium "c", and preferably into the inferior vena cava. The needle "N" is then withdrawn, leaving the guidewire 20 in place, extending out of the patient's body at the proximal portion 21. Next, trocar 300 is inserted through a first incision "s" in the patient, bluntly dissecting and tunneling under the skin, and forced out of the tissue at a second incision or site "u", creating a subcutaneous tunnel "t" under the tissue as shown in FIG. 27. This provides a way to secure the catheter as described below. Guidewire 20 is then threaded through lumen 304 of the trocar, with proximal portion 21 first inserted through trocar distal opening 310 so it emerges out of proximal opening 306 as shown in FIG. 28A. Trocar 300 is then withdrawn from the body in the direction of the arrow of FIG. 28B, leaving the guidewire 20 in place as shown. Thus, guidewire 20 extends from the right atrium and superior vena cava, out through the right internal jugular vein and through the tissue tunnel "t".

Catheter 10 is then threaded over the guidewire with the proximal portion 21 of the guidewire inserted through the distal tip lumen of the catheter, through the length of the central lumen, and through the hub 12 into the inflow tube 116 and out through fitting 15. The catheter 10 is thus threaded over the wire, through the tissue tunnel "t" where cuff 36 (not shown in FIG. 28C) is positioned in the tissue tunnel "t" to aid in securement of the catheter by enabling tissue ingrowth over a period of time. The catheter is further advanced over guidewire 20 down into the right internal jugular vein, into the superior vena cava, and into the right atrium. The guidewire 20 is withdrawn in the direction of the arrow, leaving the catheter 10 in place for use as shown in FIG. 28C. Note the stiffening member 80 or 90 (not shown in FIG. 28C for clarity) is preferably utilized, i.e. inserted over the guidewire 20 through the fitting 15, inflow tube 16, hub 12, and central lumen 40 to help guide the catheter 10 as described above. Thus, the guidewire 20 would extend through the central lumen of catheter by extending through the central lumen of the stiffening member which is positioned within the central lumen of the catheter.

As can be appreciated, the catheter will be inserted in a similar fashion through the left internal jugular vein to be positioned as depicted in FIG. 2. In this method, the subcutaneous tissue tunnel will be formed on the left side as shown in FIG. 2, by the trocar 300, and the catheter inserted over the guidewire through the tissue tunnel and through the left internal jugular vein or subclavian vein and into the superior vena cava and right atrium in the same way as described for right side insertion. It should be understood that any of the aforedescribed catheters of the present invention can be inserted in this fashion.

An alternative method of insertion is illustrated in FIGS. 29A-29G. In this method instead of forming a second incision site adjacent the incision site through which the needle and guidewire are introduced into the internal jugular vein as in FIG. 27, the trocar 300 emerges from the needle/guidewire insertion site. Although catheter 10 is shown, any of the foregoing catheters can be inserted in the same manner.

In this method, the needle and guidewire are inserted in an identical manner as illustrated in FIGS. 25 and 26. After removal of the needle, the guidewire 20 is left in place extending outwardly from the incision site, designated by "w". Next, as shown in FIG. 29A, trocar 300 is inserted through a first incision (as in FIG. 27) to create a subcutaneous tissue tunnel; however, unlike FIG. 27, trocar 300 does not emerge at a second incision site "u". Instead, trocar 300 is advanced subcutaneously to the needle incision site "w", and emerges through the site "w" as shown. Thus, as shown in FIG. 29A, the distal end of trocar 300' exits incision site "w" alongside the guidewire 20.

Guidewire 20 is then inserted (threaded) through the opening in trocar 300 as described above and then the trocar is withdrawn through the tissue tunnel "t" and out through the first incision "s", pulling the guidewire 20 through the tunnel. After the guidewire 21 is pulled through the tunnel "t" and out through incision "s", the trocar 300 is removed as shown in FIG. 29B, leaving the guidewire 20 in place. Note the guidewire 20 is positioned to form a guidewire loop 22 to facilitate insertion of the catheter as will be described below.

The catheter 10 is then advanced over the guidewire 20 (FIG. 29C), through the tissue tunnel, and exiting incision site "w" into the internal jugular vein "a" (FIG. 29D). The catheter 10, as shown, is formed into a loop 13, tracking the loop 22 of guidewire 20, and then advanced downwardly through the internal jugular vein, the superior vena cava and into the right atrium (FIG. 29E). The guidewire 20 is then withdrawn as shown in FIG. 29F, and the catheter is pushed downwardly and/or pulled back to straighten the loop to position the catheter as shown in FIG. 29G. If the catheter is inserted with a stiffening member, the guidewire would extend through the lumen of the stiffening member.

It should be appreciated that formation of the loop in the guidewire and the catheter is optional and the procedure can be performed without the loop.

FIG. 30 shows an alternate embodiment of a trocar utilized to retrieve the suture and retract it through the subcutaneous tissue tunnel. Trocar 300' is similar to trocar 300 of FIG. 29 except for the provision of eyelet 312. The suture is threaded through the eyelet (shown as two small opposing holes in the wall at the distal end of the trocar 300') and the trocar is pulled proximally through the tissue tunnel to pull the suture out through incision "s". As shown, the trocar extends through incision "w", the same incision created for insertion of the needle and guidewire.

Instead of an eyelet, a hook or other means can be provided on the trocar for holding the guidewire to enable pulling the guidewire through the tissue tunnel. That is, in these versions, the guidewire is not threaded through the trocar lumen, but rather the trocar is utilized to pull (retract) the guidewire through the tissue tunnel.

FIG. 21A illustrates an alternative trocar used for a different approach to catheter insertion. This trocar, designated by reference numeral 350, does not provide for an entire over the wire system, however it is used with an approach providing a partial over the wire system which eliminates the need for a tear way introducer sheath. As discussed in the Background Section of this application, tear away introducer sheaths are currently being utilized to guide the dialysis catheter through the vessels into the right atrium. To avoid the problems associated with the tear away sheath, the catheter in this alternate method can be advanced over a guidewire which can be placed in the manner illustrated in FIGS. 25 and 26.

In this method, trocar 350 is attached to the distal end of the catheter by insertion of barbed end 352 into a mating fitting. Other means for temporarily attaching the trocar are also contemplated. Trocar 350 has a blunt distal tip 354 and is advanced through a first tissue incision and out through a second tissue incision, bluntly dissecting tissue and forming a subcutaneous tissue tunnel in a similar manner as described above, except without the guidewire. Since trocar 350 is attached to the catheter, it pulls the catheter through the tissue tunnel, so it emerges out through the second incision. The trocar 350 is then detached from the catheter. The catheter is then bent as necessary and threaded over the guidewire into jugular vein, superior vena cava, and right atrium.

FIGS. 21J-21M illustrate an alternate embodiment of the trocar used for a partial over the wire system. Trocar 390 has a proximal end portion 392 and a distal end portion 394. The distal end portion has a dilating tip 395 to facilitate insertion through a subcutaneous tissue tunnel. The proximal portion 392 progressively reduces in diameter toward the proximal end and has a radiused surface throughout its length to provide an interference fit with the catheter. As shown, the proximal portion 392 is inserted in the distal end of the catheter, until enlarged region 393, which has a larger diameter than the diameter of the proximal end portion, abuts the catheter to limit insertion. As shown, the radiused region decreases in diameter (or transverse cross section toward the proximalmost end). The frictional engagement maintains the attachment as the trocar 390, with its blunt tip, dissects tissue through the tunnel to advance the catheter through the tunnel. Once advanced through the tunnel, the guidewire can be threaded through the distal end and the catheter inserted over the wire into the right atrium in the same manner as described above with respect to trocar 350.

FIGS. 21B-21H illustrate alternate embodiments of a trocar adapted to create a subcutaneous tissue tunnel and to subsequently be attached to a catheter. Trocar 900 and 920 each has a removable handle which is grasped by the user and then inserted into the body to create the subcutaneous tissue tunnel. The handle provides additional leverage for facilitating trocar insertion/passage. Once inserted through the tunnel, the handle is detached and the trocar is attached to the dialysis catheter as described above, for example, with reference to trocar 350 of FIG. 21A. The distal end has a dilating distal tip as described above.

More specifically, in FIGS. 21B, 21C, 21E and 21F, trocar 900 has a connecting structure 902 on a proximal end of the elongated body 903. The connecting structure 902 has a circumferential groove 904. Contained within the handle 906 is a latch 910 having an opening 912 dimensioned to receive tip 905 of connecting structure 902. The latch 910 is spring biased upwardly by spring 914 so that surface 916 is seated within a groove 904 to lock the elongated body 903 within handle 906. To release the handle 906, protruding region 918 of latch 910 is depressed, thereby forcing surface 916 out of groove 904 and placing tip 905 in alignment with opening 912 of latch 910 (shown in phantom in FIG. 21F). This enables the elongated body 903 of trocar 900 to be separated from the handle 906. After such separation, which procedurally would occur after the trocar is inserted in the body to create a tissue tunnel t as in FIG. 21D, the connecting structure can be connected to a dialysis catheter to pull the catheter through the tissue tunnel. It should be appreciated that the latch can alternatively engage the recess in the barbed fitting 352 of trocar 350 of FIG. 21A.

In the embodiment of FIGS. 21D and 21G, the connecting structure 952 extending from elongated body of trocar 950 comprises series of threads 954. Handle 960 includes a bore with an internal thread for threaded connection to thread 954. Thus, the elongated body 953 of trocar 950 can be unthreaded and removed from handle 960 after creation of the tissue tunnel and then threadedly connected to the dialysis catheter.

It should also be appreciated that the threaded connection can be used with the trocar of FIG. 21A having a barbed fitting. This is shown in FIG. 21H. The threads 351 are positioned distally of the barbed fitting 352' with the trocar handle (not shown) having a bore with a first region dimensioned to receive the barb and having threads in a second region to engage the threads of the trocar. Similarly, if desired, the circumferential groove of the embodiment of FIG. 21B can be placed distal of the barbed fitting of the trocar of FIG. 21A. The bore of the trocar handle would accommodate the barbed fitting plus include a latch to align with the region of the bore which receives the circumferential groove. In this manner, the barbed fitting would provide the connecting structure for the dialysis catheter and the latch or threads would provide the connecting structure for the trocar handle.

Turning now to one method of manufacturing the hub of the catheter, and with particular reference to FIGS. 31-37, a method is disclosed which enables connection of the central venous return (delivery) lumen of the catheter with an inflow tube and fluid connection of the five independent arterial intake (withdrawal) lumens with a single outflow tube to provide fluid connection through the connectors.

Turning first to FIG. 31, a longitudinal slit 201 is formed at a proximal portion of catheter tube 203. FIG. 32 shows the relationship of the slit 201 and the central venous lumen 205 as the slit is formed to communicate with the central lumen 205. As can be appreciated from the cross-sectional view of FIG. 33, the slit 201 is formed in the wall 206 of the catheter tube 203 between adjacent arterial lumens 209a-209e. Next, a metal pin 207 is inserted through the slit 201 for the molding process. Outer plastic venous tubing 210 is placed over the metal pin 207 as shown in FIG. 35 to ultimately communicate with the central lumen 205. Outer plastic arterial tubing 211 is also shown positioned over the catheter tube 203 which will communicate with the arterial lumens 209.

Next, conventional injection molding techniques are utilized so the soft plastic material flows around the catheter tube 203 and the metal pin 207 as shown in FIG. 36. Then, the material is cooled to harden, forming a hub 208, with the metal pin 207 removed to form lumen 204. Lumen 204 has a narrowed region 202. As shown in FIG. 37, lumen 204 fluidly connects lumen 207 of venous tube 210 with the central lumen 205 of the catheter. Lumen 212 of arterial tubing 211 communicates with the five independent arterial lumens 209.

FIGS. 38-39 illustrate another method for manufacturing the catheter connections. In this method, catheter body 402 of catheter 400 is separated into five segments 401a-401e at its proximalmost end, corresponding to each of the arterial (intake) lumens 403a-403e. FIG. 40 illustrates the five cuts 408 made in the catheter wall 407 between the adjacent arterial lumens 403 to form the five segments 401.

A separate arterial connector tube 412a-412e is positioned within a respective arterial lumen 403a-403e and is connected to a respective segment 401a-401e by solvent bonding or pressure fit. The proximal end of each connector tube 412 is positioned within arterial tube 414 which transports blood to the dialysis machine. Thus, blood flows through the arterial lumens 403, through each arterial connector tube 401 and into a single arterial (intake) tube 414. It should be understood, that if fewer or larger number of arterial lumens are provided, then an equal amount of arterial tubes would be utilized as the arterial lumens would be cut into the corresponding number of segments.

Venous (return) tubing 416 is connected to central venous lumen by venous connector tube 410 which is attached inside the venous lumen by solvent bonding, glue application or compression fit. Note that venous connector tube 410 is positioned between the segments 401. FIGS. 41-43 illustrate another alternate method for manufacturing the hub of the catheter of the present invention. This hub and associated tubing is illustrated for use with a catheter having the lumen configuration of FIG. 9C, although it can be utilized with other lumen configurations as well.

A central lumen connector (intermediate) tube 702 is joined with central lumen 78 of catheter 700. Four arterial connecting (intermediate) tubes 704 are connected to a respective arterial lumen 76a. These tubes each have a lumen that is substantially circular in cross-section along its length. The substantially circular lumens corresponds to the cross-sectional shape of the arterial lumens within catheter 10 which transition from a substantially oval cross-sectional configuration to a substantially circular cross-sectional configuration at the flared proximal portion shown in FIG. 43. Note that venous lumen 78 also transitions to a substantially circular cross-sectional configuration.

Each of the connector tubes 704 is connected to multilumen extension (arterial) tube 708 which provides flow of blood to the dialysis machine. Extension tube 708 has a flared distal portion 711 with four lumens 710, each configured for communicating with one of the connector tubes 704. As shown, each of the lumens 710 has a substantially circular cross-sectional configuration that transitions to a substantially triangular cross-sectional configuration towards the proximal portion.

Single lumen extension (venous) tube 712, which provides return of blood to the patient, connects to connector tube 702. Tube 712 has a tapered distal end 718 and its lumen 719 transitions from a substantially circular cross-sectional configuration to a substantially square configuration toward the proximal end. Molding of housing 716 with the foregoing tubes forms the catheter hub. Conventional tube clamps, such as clamps 17, 19 of FIG. 1, are placed around extension tubes 708, 712 for cutting off blood flow.

A rotatable suture ring 720 is placed around the catheter hub and preferably has a planar surface 722 to sit substantially flush with the patient's skin. Suture holes 724 are configured to receive sutures for attaching the ring (and thus the catheter) to the patient.

An alternate embodiment of the proximal end portion of the catheter is illustrated in FIGS. 55-64. With particular reference to FIGS. 55 and 56, catheter 1010 has a tube 1012 extending from hub 1020. (The intermediate and distal end of tube 1012 is not shown) A venous extension tube 1030 and three arterial extension tubes 1040a-c extend through the hub 1020 to communicate with the lumens of the catheter tube 1012. A venous clamp 1032 is shown positioned over the venous tube 1030 and an arterial clamp 1042 is shown positioned over the three arterial tubes 1040a-c. An arterial tag 1044 and venous tag 1034, to provide indication of priming volume or other information, are shown attached to the respective arterial and venous clamps. Cap 1035 is attached to the proximal end of the venous tube and is mounted within venous luer 1038. A cap 1045 is attached to the proximal end of the arterial tubes 1040a-c and is received within the arterial luer 1048. Cap 1045 includes three aligned openings to receive the stacked tubes 1040a, 1040b and 1040c. An adapter 1043 is disposed within the luer 1048 and has three openings 1046a arranged in a triangular fashion. (FIG. 60) This triangular arrangement maintains the arterial tubes in a radial fashion to better ensure injection of heparinized saline, contrast or other fluids is evenly distributed among the three tubes. That is, the tubes 1040a, 1040b, 1040c are positioned adjacent each other and in substantially the same plane, e.g. vertically in the orientation of FIG. 56.

As shown, the arterial tubes 1040a-c emerge from the adapter 1043 in a triangular/radial arrangement and then transition to the stacked arrangement through cap 1045, and enter hub 1020 in this vertical arrangement.

With reference to FIGS. 58, 59, and 63, the arterial clamp 1042 and tag 1044 are shown in detail. Arterial clamp 1042 has a first arm 1042a integral with the second arm 1042b and hingedly connected thereto for movement between an opened unclamped position and a closed clamped position where latch 1047a is engaged by edge 1047b. The second arm 1042b includes two pairs of posts 1053 which limit lateral movement of the stacked arterial extension tubes 1040a-c. FIGS. 63 and 64 illustrate the tubes 1040a, 1040b, and 1040c stacked (vertically arranged in the orientation shown) in abutting relationship in the space 1051 between the posts 1053. Extension 1057 of arm 1042a engages the topmost tube 1040a to pinch the three tubes 1040a-c to close off flow therein.

During assembly, tag 1044 is attached to the clamp 1042. Tag 1044 has bridge 1048 extending between walls 1044a, 1044b and two short projections 1049a, 1049b extending from each of the respective walls. FIG. 63 illustrates the tag with a portion broken away to illustrate the bridge 1048 and the projection 1049a. That is, the wall 1044a has been removed for clarity to illustrate the connection of the tag 1044 to the clamp 1042.

The venous clamp and tag are illustrated in FIGS. 61 and 62. The clamp 1032 is shown in the neutral at rest position in FIG. 61A and FIG. 64, i.e. before latching of the arms 1033a, 1033b by latch 1031 engaged by the edge of arm 1033a. Tag 1034 has two bridges 1039a and 1039b extending between the walls 1037a and 1037b, and is placed on the clamp 1032 during assembly. FIG. 64 illustrates the tag 1034 with wall 1037b removed for clarity.

FIG. 57B illustrates a cross-sectional view of the catheter tube showing the circular venous lumen 1011 and radially disposed arterial lumen 1013a-c, somewhat kidney shaped. As shown, opposite walls 1014a, 1015a are curved, with adjoining walls 1116a, 1116b also radiused. The walls of the lumens 1013b and 1013c are likewise shaped and for clarity not labeled. Longitudinally extending reinforcing ribs or wall extensions 1024 (FIG. 57A), formed during the manufacturing step, are provided extending partially along the reduced diameter section 1021 of the catheter to increase rigidity of the catheter. As shown, these ribs 1024 terminate proximally of the venous lumen openings 1018 formed in the wall of the reduced diameter section 1017 of the catheter 1020. FIG. 57C illustrates an alternative embodiment of the lumens, having thicker walls between the lumens 2013a, 2013b and 2013c to increase the structural rigidity of the catheter and reduce kinking. For example, the thickness T1 of the wall W1 of FIG. 57C is greater than the thickness T2 of wall W2 of FIG. 57B and the thickness T3 of wall W3 is greater than the thickness of T4 of wall W4 of lumen configuration of FIG. 57B. As shown, opposite walls 2014a, 2015a of lumen 2013a are curved, with adjoining walls 2016a, 2016b have a large radius. The walls of the lumens 1013b and 1013c are likewise shaped and for clarity not labeled. The lumens can have various dimensions. In one embodiment of the lumen shape of FIG. 57C, each of the arterial lumens has the same dimension and is about 0.033 square inches in cross-section. The venous lumen in the illustrated embodiment is circular and in one embodiment has a cross-sectional area of about 0.005 square inches. Other dimensions are also contemplated.

The catheters described above can optionally include a surface treatment on the exterior and/or the interior. The surface treatments can include for example, a hydrophilic coating to increase lubricity and facilitate insertion, a drug coating such as heparin or containing IIb, IIIa inhibitors, inert coating substances such as Sorins carbon coating, and/or active coatings such as a silver ion coating.

It should be appreciated that although the catheter is described herein as a dialysis catheter for hemodialysis, the catheter disclosed herein could have other surgical applications, such as drug delivery or blood sampling. Moreover, features of the catheter, tip configurations and lumen configurations can be utilized on other catheters.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A dialysis catheter comprising a catheter body having first portion having a first diameter, an elongated distal portion having a second diameter smaller than the first diameter, and a transition region between the first portion and distal portion, a first longitudinally extending central delivery lumen configured to deliver blood terminating in an opening in the distal portion, and at least two independent longitudinally extending withdrawal lumens positioned radially of the first lumen, the at least two withdrawal lumens configured to withdraw blood from a patient and each terminating in a longitudinally directed opening in the transition region, and a plurality of longitudinally extending reinforcing ribs extending radially from an outer surface of the catheter and axially partially along the outer surface of the distal portion of the catheter along a length of the catheter to thereby increase a cross-sectional dimension of the distal portion of the catheter distal of the longitudinally extending withdrawal lumens, and the longitudinally extending ribs terminating proximal of the opening in the central lumen.

2. The dialysis catheter of claim 1, wherein the central lumen is circular in configuration.

3. The dialysis catheter of claim 2, wherein the withdrawal lumens are kidney shaped.

4. The dialysis catheter of claim 1, wherein the withdrawal lumens are kidney shaped.

5. The dialysis catheter of claim 1, wherein the each of withdrawal lumens has a cross-sectional configuration with first and second opposing walls and third and fourth walls joining the first and second walls on opposite sides, the first, second, third and fourth walls being curved.

6. The dialysis catheter of claim 1, wherein the catheter includes a plurality of side openings communicating with the central lumen and the reinforcing ribs terminate proximally of the side openings.

7. The dialysis catheter of claim 1, wherein the catheter includes a plurality of side openings communicating with the central lumen and the reinforcing ribs terminate proximally of the side openings.

8. A dialysis catheter comprising a body having first portion having a first diameter, an elongated distal portion having a second diameter smaller than the first diameter, and a transition region between the first portion and distal portion, a first longitudinally extending blood delivery lumen configured to deliver blood, the blood delivery lumen terminating in an opening at a distalmost tip of the catheter, and at least two independent longitudinally extending blood withdrawal lumens, the at least two withdrawal lumens configured to withdraw blood from a patient and each terminating in a longitudinally directed opening in the transition region spaced proximally from the opening in the blood delivery lumen, and a plurality of longitudinally extending reinforcing ribs extending radially from an outer surface of the catheter from the transition region and axially partially along the outer surface of the catheter to provide a raised surface and terminating proximal of the opening in the delivery lumen, wherein a length of the ribs exceeds a length of the longitudinally directed openings so as to extend beyond the transition region and over the distal portion of the catheter.

9. The dialysis catheter of claim 8, wherein the delivery lumen is circular in configuration.

10. The dialysis catheter of claim 9, wherein each of the withdrawal lumens has a cross-sectional configuration with first and second opposing walls and third and fourth walls joining the first and second walls on opposite sides, the first, second, third and fourth walls being curved.

11. The dialysis catheter of claim 8, wherein a wall at the longitudinally directed opening curves toward a proximal portion of the catheter.

12. The dialysis catheter of claim 8, wherein each of the withdrawal lumens has a cross-sectional configuration with first and second opposing walls and third and fourth walls joining the first and second walls on opposite sides, the first, second, third and fourth walls being curved.

13. The dialysis catheter of claim 12, wherein the catheter includes a side opening in a sidewall of the catheter communicating with the delivery lumen and the reinforcing ribs terminate proximally of the side opening.

14. The dialysis catheter of claim 8, wherein the catheter includes a side opening in a sidewall of the catheter communicating with the delivery lumen and the reinforcing ribs terminate proximally of the side opening.

15. A dialysis catheter comprising a first portion having a first diameter, an elongated distal portion having a second diameter smaller than the first diameter, and a transition region between the first portion and distal portion, a first longitudinally extending central delivery lumen configured to deliver blood terminating in an opening in the distal portion, and at least two independent longitudinally extending withdrawal lumens positioned radially of the first lumen, the at least two withdrawal lumens configured to withdraw blood from a patient and each terminating in a longitudinally directed opening in a transition region, and a plurality of longitudinally extending reinforcing ribs extending partially along an outer surface of the catheter and terminating proximal of the opening in the central lumen, the reinforcing ribs extending from the longitudinally directed openings, separating the withdrawal lumens such that adjacent withdrawal lumens share a common rib wherein a length of the ribs exceeds a length of the longitudinally directed openings so as to extend beyond the transition region and over the distal portion of the catheter.

16. The dialysis catheter of claim 15, wherein the longitudinally directed openings for the withdrawal lumens are axially aligned.

17. A dialysis catheter comprising a first portion having a first diameter, an elongated distal portion having a second diameter smaller than the first diameter, and a transition region between the first portion and distal portion, a first longitudinally extending blood delivery lumen configured to deliver blood, the delivery lumen terminating in an opening at a distalmost tip of the catheter, and at least two independent longitudinally extending blood withdrawal lumens, the at least two withdrawal lumens configured to withdraw blood from a patient and each terminating in a longitudinally directed opening in the transition region spaced proximally from the opening in the blood delivery lumen, and a plurality of longitudinally extending reinforcing ribs extending from the transition region and partially along an outer surface of the distal portion of the catheter forming a raised outer surface as they extend longitudinally along the outer surface to thereby increase a cross-sectional dimension of the distal portion of the catheter distal of the longitudinally extending withdrawal lumens and terminating proximal of the opening in the delivery lumen, the reinforcing ribs separating the withdrawal lumens such that the withdrawal lumens share a common rib.

18. The dialysis catheter of claim 17, wherein the delivery lumen is circular in configuration.

19. The dialysis catheter of claim 17, wherein each of the withdrawal lumens has a cross-sectional configuration with first and second opposing walls and third and fourth walls joining the first and second walls on opposite sides, the first, second, third and fourth walls being curved.

20. The dialysis catheter of claim 17, wherein the catheter includes a side opening in a sidewall of the catheter communicating with the delivery lumen and the reinforcing ribs terminate proximally of the side opening.

21. The dialysis catheter of claim 17, wherein the longitudinally directed openings for the withdrawal lumens are axially aligned.

\* \* \* \* \*